United States Patent
Do et al.

(10) Patent No.: US 10,227,577 B2
(45) Date of Patent: Mar. 12, 2019

(54) METHOD FOR SELECTION OF HIGH M6P RECOMBINANT PROTEINS

(71) Applicant: Amicus Therapeutics, Inc., Cranbury, NJ (US)

(72) Inventors: Hung V. Do, New Hope, PA (US); Russell Gotschall, Doylestown, PA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 15/473,994

(22) Filed: Mar. 30, 2017

(65) Prior Publication Data

US 2017/0335301 A1    Nov. 23, 2017

Related U.S. Application Data

(60) Provisional application No. 62/315,400, filed on Mar. 30, 2016, provisional application No. 62/457,584, filed on Feb. 10, 2017.

(51) Int. Cl.
  *C12N 9/26*  (2006.01)
  *A61K 38/00* (2006.01)

(52) U.S. Cl.
  CPC ...... *C12N 9/2408* (2013.01); *C12Y 302/0102* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 4,837,237 A | 6/1989 | Rohrschneider et al. | |
| 4,985,445 A | 1/1991 | Tsuruoka et al. | |
| 5,011,829 A | 4/1991 | Hirsch et al. | |
| 5,103,008 A | 4/1992 | Scudder et al. | |
| 5,236,838 A | 8/1993 | Rasmussen et al. | |
| 5,399,567 A | 3/1995 | Platt et al. | |
| 5,472,969 A | 12/1995 | Platt et al. | |
| 5,580,757 A | 12/1996 | Desnick et al. | |
| 5,786,369 A | 7/1998 | Platt et al. | |
| 5,801,185 A | 9/1998 | Platt et al. | |
| 5,879,680 A | 3/1999 | Ginns et al. | |
| 6,083,725 A | 7/2000 | Selden et al. | |
| 6,118,045 A | 9/2000 | Reuser et al. | |
| 6,210,666 B1 | 4/2001 | Miyamura | |
| 6,225,325 B1 | 5/2001 | Jacob | |
| 6,274,597 B1 | 8/2001 | Fan et al. | |
| 6,395,884 B1 | 5/2002 | Selden et al. | |
| 6,451,600 B1 | 9/2002 | Rasmussen et al. | |
| 6,458,574 B1 | 10/2002 | Selden et al. | |
| 6,461,609 B1 | 10/2002 | Calhoun et al. | |
| 6,465,488 B1 | 10/2002 | Butters et al. | |
| 6,534,300 B1 | 3/2003 | Canfield | |
| 6,537,785 B1 | 3/2003 | Canfield | |
| 6,545,021 B1 | 4/2003 | Mueller et al. | |
| 6,583,158 B1 | 6/2003 | Fan et al. | |
| 6,589,964 B2 | 7/2003 | Fan et al. | |
| 6,599,919 B2 | 7/2003 | Fan et al. | |
| 6,696,059 B2 | 2/2004 | Jacob et al. | |
| 6,916,829 B2 | 7/2005 | Fan et al. | |
| 7,141,582 B2 | 11/2006 | Fan et al. | |
| 7,351,410 B2 | 4/2008 | van Bree et al. | |
| 7,371,366 B2 | 5/2008 | Canfield | |
| 7,396,811 B2 | 7/2008 | LeBowitz et al. | |
| 7,560,424 B2 | 7/2009 | LeBowitz et al. | |
| 7,655,226 B2 | 2/2010 | Van Bree et al. | |
| 7,658,916 B2 | 2/2010 | Zhu et al. | |
| 7,785,856 B2 | 8/2010 | LeBowitz et al. | |
| 7,858,576 B2 | 12/2010 | LeBowitz et al. | |
| 7,910,545 B2 | 3/2011 | Meeker et al. | |
| 7,981,864 B2 | 7/2011 | LeBowitz | |
| 8,785,168 B2 | 7/2014 | LeBowitz et al. | |
| 8,900,552 B2 | 12/2014 | Chen | |
| 8,940,766 B2 | 1/2015 | Boyd et al. | |
| 9,056,101 B2 | 6/2015 | Lockhart et al. | |
| 9,181,184 B2 | 11/2015 | Mugrage et al. | |
| 9,186,420 B2 | 11/2015 | Koeberl | |
| 9,303,249 B2 | 6/2016 | Valenzano et al. | |
| 9,404,100 B2 | 8/2016 | Valenzano et al. | |

(Continued)

FOREIGN PATENT DOCUMENTS

| | | |
|---|---|---|
| EP | 1137762 B1 | 10/2008 |
| EP | 2020438 A1 | 2/2009 |

(Continued)

OTHER PUBLICATIONS

Chavez et al. Domain 5 of the Cation-Independent Mannose 6-Phosphate Receptor Preferentially Binds Phosphodiesters (Mannose 6-Phosphate N-Acetylglucosamine Ester)., Biochemistry (2007), 46: 12604-12617.*
Amalfitano et al., "Recombinant human acid α-glucosidase enzyme therapy for infantile glycogen storage disease type II: Results of a phase I/II clinical trial," Genetics in Medicine 3(2): 132-138 (2001).
Asano, N. et al. (1994) "Nitrogen-in-the-ring pyranoses and furanoses: structural basis of inhibition of mammalian glycosidases" *J Med Chem*, 37:3701-3706.
Banati, M. et al. (2011) "Enzyme replacement therapy induces T-cell responses in late-onset Pompe disease" *Muscle Nerve*, 44(5):720-726.

(Continued)

*Primary Examiner* — Iqbal H Chowdhury
(74) *Attorney, Agent, or Firm* — Finnegan, Henderson, Farabow, Garrett & Dunner, LLP

(57) ABSTRACT

Methods for the production, capturing and purification of recombinant human lysosomal proteins are described. Such recombinant human lysosomal proteins can have high content of mannose-6-phosphate residues. Also described are pharmaceutical compositions comprising such recombinant human lysosomal proteins, as well as methods of treatment and uses of such recombinant human lysosomal proteins.

10 Claims, 42 Drawing Sheets

Specification includes a Sequence Listing.

(56) References Cited

U.S. PATENT DOCUMENTS

| | | |
|---|---|---|
| 2002/0049233 A1 | 4/2002 | Kararli et al. |
| 2002/0095135 A1 | 7/2002 | Meeker et al. |
| 2002/0157123 A1* | 10/2002 | Reuser ............... A01K 67/0275 800/14 |
| 2004/0180419 A1 | 9/2004 | Fan |
| 2004/0204379 A1 | 10/2004 | Cheng et al. |
| 2005/0058634 A1 | 3/2005 | Zhu |
| 2005/0244400 A1 | 11/2005 | LeBowitz et al. |
| 2006/0121018 A1 | 6/2006 | LeBowitz |
| 2006/0264467 A1 | 11/2006 | Mugrage et al. |
| 2007/0178081 A1 | 8/2007 | Fan |
| 2009/0117091 A1 | 5/2009 | LeBowitz et al. |
| 2009/0203575 A1 | 8/2009 | LeBowitz et al. |
| 2010/0119502 A1 | 5/2010 | Do et al. |
| 2010/0260740 A1 | 10/2010 | Boyd et al. |
| 2010/0266571 A1 | 10/2010 | Lockhart et al. |
| 2011/0136151 A1 | 6/2011 | Wustman et al. |
| 2011/0189710 A1 | 8/2011 | Wustman et al. |
| 2011/0268721 A1 | 11/2011 | Do et al. |
| 2011/0300120 A1 | 12/2011 | Avila et al. |
| 2015/0086530 A1 | 3/2015 | Greene et al. |
| 2015/0147309 A1 | 5/2015 | Parenti et al. |
| 2015/0258081 A1 | 9/2015 | Lukas et al. |
| 2016/0184410 A1 | 6/2016 | Chen |
| 2016/0243203 A1 | 8/2016 | van Bree et al. |
| 2017/0056483 A1 | 3/2017 | Valenzano et al. |
| 2017/0298335 A1 | 10/2017 | Gotschall et al. |

FOREIGN PATENT DOCUMENTS

| | | |
|---|---|---|
| FR | 2861991 A1 | 5/2005 |
| JP | 2005-523882 A | 8/2005 |
| JP | 2008-525457 A | 7/2008 |
| JP | 2008-545657 A | 12/2008 |
| JP | 2010-525084 A | 7/2010 |
| JP | 2011-512876 A | 4/2011 |
| WO | WO 00/034451 A1 | 6/2000 |
| WO | WO 01/019955 A2 | 3/2001 |
| WO | WO 03/032907 A2 | 4/2003 |
| WO | WO 2004/069190 A2 | 8/2004 |
| WO | WO 2005/077093 A2 | 8/2005 |
| WO | WO 2006/071613 A2 | 7/2006 |
| WO | WO 2006/125141 A2 | 11/2006 |
| WO | WO 2008/112525 A2 | 9/2008 |
| WO | WO 2008/134628 A2 | 11/2008 |
| WO | WO 2009/066069 A1 | 5/2009 |
| WO | WO 2009/114679 A2 | 9/2009 |
| WO | WO 2010/015816 A2 | 2/2010 |
| WO | WO 2010/148253 A2 | 12/2010 |
| WO | WO 2011/109600 A1 | 9/2011 |
| WO | WO 2012/145644 A1 | 10/2012 |
| WO | WO 2013/013017 A2 | 1/2013 |
| WO | WO 2013/091897 | 6/2013 |
| WO | WO 2016/054231 A1 | 4/2016 |

OTHER PUBLICATIONS

Barton, N.W. et al. (1991) "Replacement Therapy for Inherited Enzyme Deficiency—Macrophage-Targeted Glucocerebrosidase for Gaucher's Disease" *N Eng J Med*, 324:1464-1470.

Beck, M. (Sep. 2009) "Alglucosidase alfa: Long term use in the treatment of patients with Pompe disease" *Therapeutics and Clinical Risk Management*, 5:767-772.

Butters, T.D. et al. (2005) "Imino Sugar Inhibitors for Treating the Lysosomal Glycosphingolipidoses" *Glycobiology*, 15(10):43E-52R.

Courageot, M-P. et al. (2000) "α-Glucosidase inhibitors reduce dengue virus production by affecting the initial steps of virion morphogenesis in the endoplasmic reticulum" *J Virol*, 74:564-572.

Cox, T. et al. (2000) "Novel oral treatment of Gaucher's disease with N-butyldeoxynojirimycin (OGT 918) to decrease substrate biosynthesis" *The Lancet*, 355:1481-1485.

Dale, M.P. et al. (1985) "Reversible inhibitors of β-glucosidase" *Biochemistry*, 24:3530-3539.

Database SCORE. SEQ ID No. 1 sequence in WO 2012145644 A1. Retrieved from: http://score.uspto.gov/ScoreAccessWeb/viewSeqIdResult.htm, pp. 1-3; accessed Jan. 22, 2018, 3 pages.

Do, H. (Feb. 13, 2014) "Chemical Conjugation of Targeting Peptide to ERTs Improve Receptor Binding and Substrate Clearance in Mouse Models of Disease" Amicus Technologies: Presentation from the 10th Lysosomal Disease Network WORLDSymposium, San Diego, CA, Feb. 10-13, 2014; 14 pages.

Do, H. et al. (Feb. 13, 2014) "Chemical Conjugation of Targeting Peptide to ERTs Improve Receptor Binding and Substrate Clearance in Mouse Models of Disease" Amicus Technologies: Poster from the 10th Annual Lysosomal Disease Network WORLDSymposium, San Diego, CA, Feb. 10-13, 2014, Abstract #277; 1 page.

Do, H. et al. (2017) "ATB200/AT2221 Cleared Accumulated Glycogen and Reversed Cellular Dysfunction to Increase Functional Muscle Strength in Mouse Model of Pompe Disease" Amicus Technologies: Poster from the 13th Annual Lysosomal Disease Network WORLDSymposium, San Diego, CA, Feb. 13-17, 2017; Poster #74, Abstract A-348, 1 page.

Duke University Medical Center (1997) "Duke Obtains FDA Designation for Pompe Disease Therapy" Press Release, dated Sep. 2, 1997, 2 pages.

European Application No. 15845664.0, filed Apr. 6, 2017, by Amicus Therapeutics, Inc.: Supplementary European Search Report, dated Feb. 12, 2018, 13 pages.

Fryar, C.D. et al. (Oct. 2012) "Anthropometric Reference Data for Children and Adults: United States 2007-2010" National Center for Health Statistics. *Vital Health Stat*, Series 11, No. 252, 48 pages.

Genzyme Corporation (2010) Myozyme®. Highlights of Prescribing Information. Cambridge, MA: Genzyme Corporation, Jun. 2010, 3 pages.

Gotschall, R. (2015) "Novel rhGAA with Optimal Glycosylation Is Significantly Better than Alglucosidase Alfa for Glycogen Clearance in Skeletal Muscles of Gaa KO Mice" Amicus Technologies: Presentation from the 11th Lysosomal Disease Network WorldSymposium, Feb. 9-13, 2015, Orlando, Florida; 12 pages.

Gotschall, R. (2015) "Novel rhGAA with Optimal Glycosylation Is Significantly Better than Alglucosidase Alfa for Glycogen Clearance in Skeletal Muscles of Gaa KO Mice" Amicus Technologies: Poster from the ACMG Annual Clinical Genetics Meeting, Mar. 25-27, 2015, Salt Lake City, Utah; Abstract #739, 1 page.

Gotschall, R. et al. (2015) "Novel rhGAA with Optimal Glycosylation Is Significantly Better than Alglucosidase Alfa for Glycogen Clearance in Skeletal Muscles of Gaa KO Mice" Amicus Technologies: Abstract from the 11th Lysosomal Disease Network WORLDSymposium, Feb. 9-13, 2015, Orlando, Florida. Abstract 94, 1 page.

Gotschall, R. et al. (2017) "ATB200/AT2221 Reverses Cellular Dysfunction and Increases Muscle Strength in a Pompe Disease Mouse Model" Amicus Therapeutics: Poster from the 4th International Glycogen Storage Disease (GSD) Conference, Jun. 15-17, 2017, University Medical Center, Groningen, The Netherlands; Abstract 48, 1 page.

Jeyakumar, M. et al. (1999) "Delayed symptom onset and increased life expectancy in Sandhoff disease mice treated with N-butyldeoxynojirimycin" *Proc Natl Acad Sci USA*, 96:6388-6393.

Johnson, F.K. et al. (2017) "First-in-Human Preliminary Pharmacokinetic and Safety Data on a Novel Recombinant Acid α-Glucosidase, ATB200, Co-administered With the Pharmacological Chaperone AT2221 in ERT-Experienced Patients With Pompe Disease" Amicus Technologies: Poster from the 13th Annual Lysosomal Disease Network WORLDSymposium, San Diego, CA, Feb. 13-17, 2017; Poster #LB-26, 1 page.

Khanna. R. et al. (2012) "The pharmacological chaperone AT2220 increases recombinant human acid α-glucosidase uptake and glycogen reduction in a mouse model of Pompe disease" *PLoS ONE*, 7(7):e40776, 14 pages.

Khanna, R. et al. (2014) "The pharmacological chaperone AT2220 increases the specific activity and lysosomal delivery of mutant acid alpha-glucosidase, and promotes glycogen reduction in a transgenic mouse model of Pompe disease" *PLoS One*, 9(7):e102092, 16 pages.

(56) References Cited

OTHER PUBLICATIONS

Khanna, R. et al. (2016) "Co-Administration of the Pharmacological Chaperone AT2221 with a Proprietary Recombinant Human Acid α-Glucosidase Leads to Greater Plasma Exposure and Substrate Reduction Compared to Alglucosidase Alfa" Amicus Therapeutics: Poster from the 12th Annual Lysosomal Disease Network WORLDSymposium Meeting, Feb. 29-Mar. 4, 2016, San Diego, California; 1 page.

Kishnani, P. et al. (2017) "Duvoglustat HCl Increases Systemic and Tissue Exposure of Active Acid α-Glucosidase in Pompe Patients Co-administered with Alglucosidase α" *Molecular Therapy*, 25(5):1199-1208.

Klinge, L. et al. (2005) "Enzyme replacement therapy in classical infantile Pompe disease: results of a ten-month follow-up study" *Neuropediatrics*, 36(1):6-11.

Legler, G. and S. Pohl (1986) "Synthesis of 5-amino-5-deoxy-D-galactopyranose and 1,5-dideoxy-1,5-imino-D-galactitol, and their inhibition of alpha- and beta-D-galactosidases" *Carbohydrate Res*, 155:119-129.

Lembcke, B. et al. (1991) "Lysosomal storage of glycogen as a sequel of alpha-glucosidase inhibition by the absorbed deoxynojirimycin derivative emiglitate (BAYo1248). A drug-induced pattern of hepatic glycogen storage mimicking Pompe's disease (glycogenesis type II)" *Res Exp Med*, 191(6): 389-404.

Lun, Y. et al. (2015) "Histological examination of the effect of a highly phosphorylated proprietary recombinant human acid alpha-glucosidase on glycogen reduction in disease-relevant muscles of Pompe mice" Amicus Technologies: Poster from the Lysosomal Disease Network 11th WORLDSymposium, Feb. 9-13, 2015, Orlando, Florida; 1 page.

Lun, Y. et al. (2017) "A Novel Recombinant Human Acid Alpha-Glucosidase, ATB200, Leads to Greater Substrate Reduction and Improvement in Pompe Disease-Relevant Markers Compared to Alglucosidase Alfa in Gaa KO Mice" Amicus Technologies: Poster from the 13th Annual Lysosomal Disease Network WORLDSymposium, San Diego, CA, Feb. 13-17, 2017; 1 page.

Lun, Y. et al. (2017) "Stabilized Next-Generation Recombinant Human Acid Alpha-Glucosidase ATB200 Clears Accumulated Glycogen and Reverses Cellular Dysfunction to Increase Muscle Strength in a Mouse Model of Pompe Disease" Amicus Therapeutics: Poster from the 2017 Muscular Dystrophy Association Scientific Conference, Mar. 19-11, 2017, Arlington, Virginia; 1 page.

Martiniuk et al., "Correction of Glycogen Storage Disease Type II by Enzyme Replacement with a Recombinant Human Acid Maltase Produced by Over-Expression in a CHO-HDFR$^{neg}$ Cell Line," Biochemical and Biophysical Research Communications, 276(3):917-923 (2000).

Mellor, H.R. et al. (2004) "Cellular effects of deoxynojirimycin analogues; uptake, retention and inhibition of glycosphingolipid biosynthesis" *Biochem J*, 381:861-866.

McVie-Wylie, et al., "Biochemical and pharmacological characterization of different recombinant acid α-glucosidase preparations evaluated for the treatment of Pompe disease," Molecular Genetics and Metabolism, 94: 448-455 (2008).

National Institutes of Health Clinical Center (2002) *Patient Education Materials: Giving a subcutaneous injection*. Bethesda, MD: NIH Clinical Center, 3 pages.

Okumiya et al., Chemical chaperones improve transport and enhance stability of mutant α-glucosidases in glycogen storage disease type II. Mol. Genet. Metab. 90: 49-57 (2007).

Parenti et al., A Chaperone Enhances Blood α-Glucosidase Activity in Pompe Disease Patients Treated with Enzyme Replacement Therapy. Mol. Ther. 22(11):2004-2012 (2014).

Parenti, G. et al. (2005) "Alpha-Glucosidase Enhancement in Fibroblasts from Patients with Pompe Disease" *J Inherit Metab Dis*, 28(Suppl. 1):193, Abstract 383-P.

PCT International Search Report and Written Opinion dated May 8, 2013, in PCT/US2013/029660, 8 pages.

PCT International Search Report and Written Opinion dated Oct. 1, 2013, in PCT/US2013/039215, 9 pages.

PCT International Search Report and Written Opinion dated Jan. 6, 2016, in PCT/US2015/053252, 9 pages.

PCT International Search Report and Written Opinion dated Mar. 7, 2017, in PCT/US2016/069243, 10 pages.

Platt, F.M. et al. (1997) "Prevention of Lysosomal Storage in Tay-Sachs Mice Treated with N-butyldeoxynojirimycin" *Science*, 276:428-431.

Porto, C. et al. (2009) "The Pharmacological Chaperone N-butyldeoxynojirimycin Enhances Enzyme Replacement Therapy in Pompe Disease Fibroblasts" *Mol Ther*, 17(6):964-971.

Raben, N. et al. (2005) "Replacing acid alpha-glucosidase in Pompe disease: recombinant and transgenic enzymes are equipotent, but neither completely clears glycogen from type II muscle fibers" *Mol Ther*, 11(1):48-56.

Ruvinov, S.B. et al. (1995) "Monovalent Cations Partially Repair a Conformational Defect in a Mutant Tryptophan Synthase $\alpha_2 \beta_2$ 132 Complex (β-E109A)" *J Biol Chem*, 270: 17333-17338.

Sathe, S. et al. (2017) "Preliminary Pharmacokinetic and Safety Data in Patients With Pompe Disease in First-in-Human Study Receiving ATB200/AT2221" Amicus Therapeutics: Poster from the 2017 Muscular Dystrophy Association Scientific Conference, Mar. 19-11, 2017, Arlington, Virginia; 1 page.

Sathe, S. et al. (2017) "Preliminary Safety, Pharmacokinetic, Pharmacodynamic, and Efficacy Data in Patients With Pompe Disease Receiving ATB200/AT2221 in First-in-Human Study" Amicus Therapeutics: Poster from the 4th International Glycogen Storage Disease (GSD) Conference, Jun. 15-17, 2017, University Medical Center, Groningen, The Netherlands; 1 page.

U.S. Appl. No. 14/379,131: Non-Final Office Action, dated Sep. 15, 2015, 13 pages.

Valenzano, K.J. et al. (Jun. 2011) "Identification and characterization of pharmacological chaperones to correct enzyme deficiencies in lysosomal storage disorders" *Assay and Drug Development Technologies*, 9(3):213-235.

Van Der Ploeg, A.T. et al. (1988) "Receptor-Mediated Uptake of Acid α-Glucosidase Corrects Lysosomal Glycogen Storage in Cultured Skeletal Muscle" *Pediatric Research*, 24(1):90-94.

Van Hove, J.L.K. et al. (1996) "High-level production of recombinant human lysosomal acid α-glucosidase in Chinese hamster ovary cells which targets to heart muscle and corrects glycogen accumulation in fibroblasts from patients with Pompe disease" *Proc Natl Acad Sci USA*, 93:65-70.

Van Hove, J.L.K. et al. (1997) "Purification of recombinant human precursor acid α-glucosidase" *Biochem Mol Biol Int*, 43(3):613-623.

Wilson, B.A. et al. (2003) *Prentice Hall Nurse's Drug Guide 2003 Companion Website*. [online]. Retrieved from: http://wps.prenhall.com/chet_wilson_drugguides_1 /6/1576/403472.cw/index.html; accessed Sep. 30, 2014.

Shin-Buehring, Y.S. et al. (1978) "Separation of acid and neutral α-glucosidase isoenzymes from fetal and adult tissues, cultivated fibroblasts and amniotic fluid cells by DEAE-cellulose and Sephadex G-100 column chromatography" *Clinica Chimica Acta* 89(3):393-404, 12 pages.

\* cited by examiner

Structure and Receptor Affinity for High Mannose and Phosphorylated Oligosaccharides

Non-phosporylated High Mannose N-glycan:

Mono-M6P N-glycan: Lower affinity for CI-MPR ($K_n \sim 7000$ nM)

Bis-M6P N-glycan: High Affinity for CI-MPR ($K_n = 2$ nM)

Mannose 6-phrosphate (M6P)

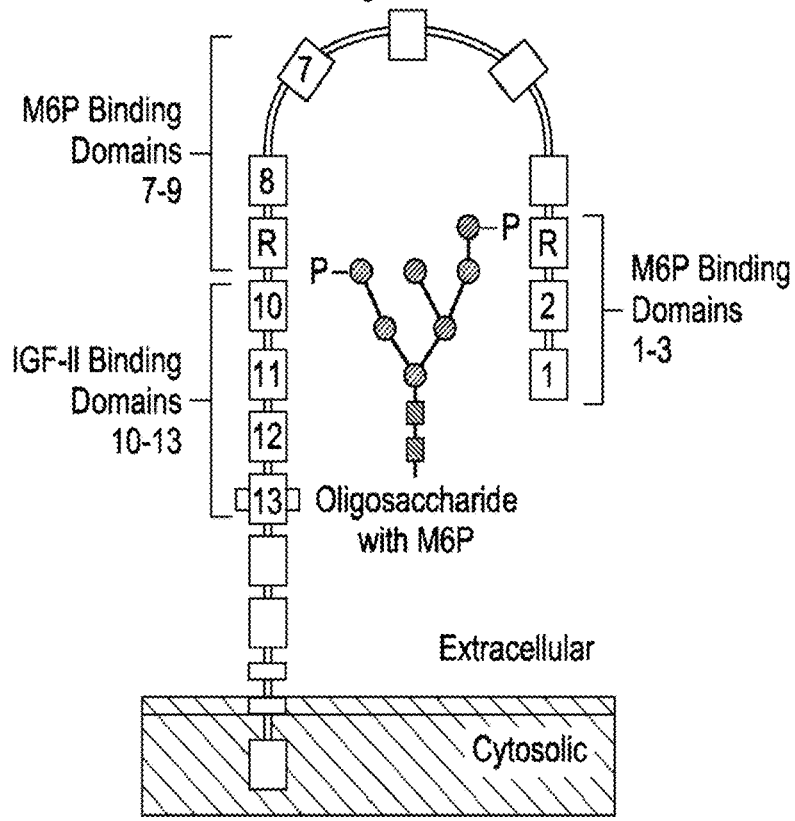

Fig. 3A

Ligands; Affinity and In Vivo Location of Three Glycoprotein Receptors

| Ligand | Receptor | Affinity (nmolar) | Location |
|---|---|---|---|
| Bis-Phosphoylated Glycan | CIMPR | 2 | All Cells |
| Mono-Phosphorylated Glycan | | 7,000 | |
| High Mannose Glycan | Mannose Receptor | 20[b] | Macrophages Dendritic Cells |
| De-sialylated Complex Glycan | Asialyoglycoprotein Receptor | 7[c] | Hepatocytes |

Reference: [a]Tong *et al* 1989; [b]Taylor *et al* 1992; [c]Schwartz *et al* 1981

Fig. 3B

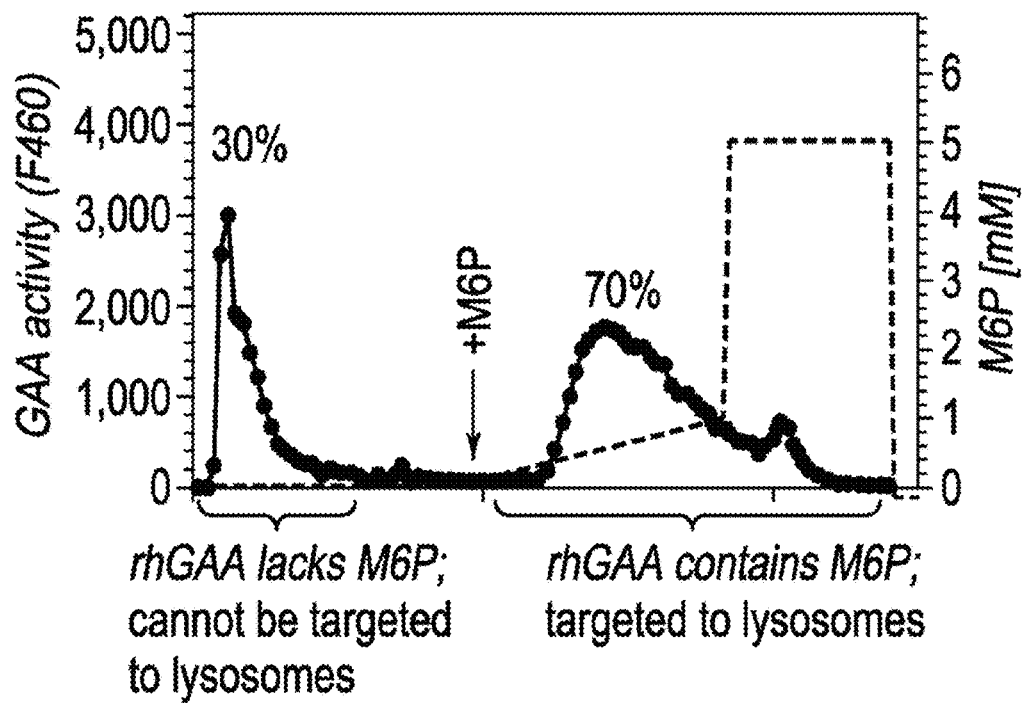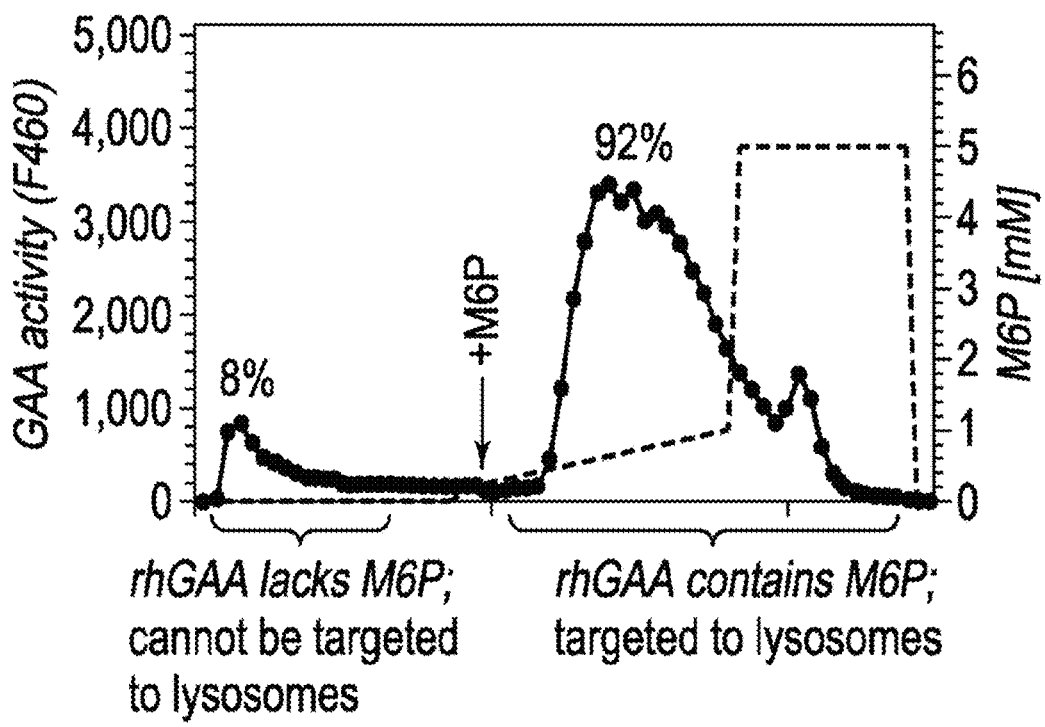
FIG. 8

Distribution of N-Glycans on rhGAA Preparations

| | Lumizyme | BP-rhGAA* | ATB200 1 | ATB200 2 |
|---|---|---|---|---|
| Complex Type N-Glycans | 70.7% | 48.9% | 51.0% | 47.5% |
| Hybrid Type N-Glycans | 6.7% | 9.7% | 4.4% | 3.7% |
| High Mannose Type N-Glycans: | | | | |
| Non-phosphorylated | 15.8% | 23.7% | 14.0% | 9.9% |
| Mono-M6P | 5.2% | 10.4% | 13.4% | 14.2% |
| Bis-M6P | 1.6% | 6.8% | 17.2% | 24.7% |

FIG. 10

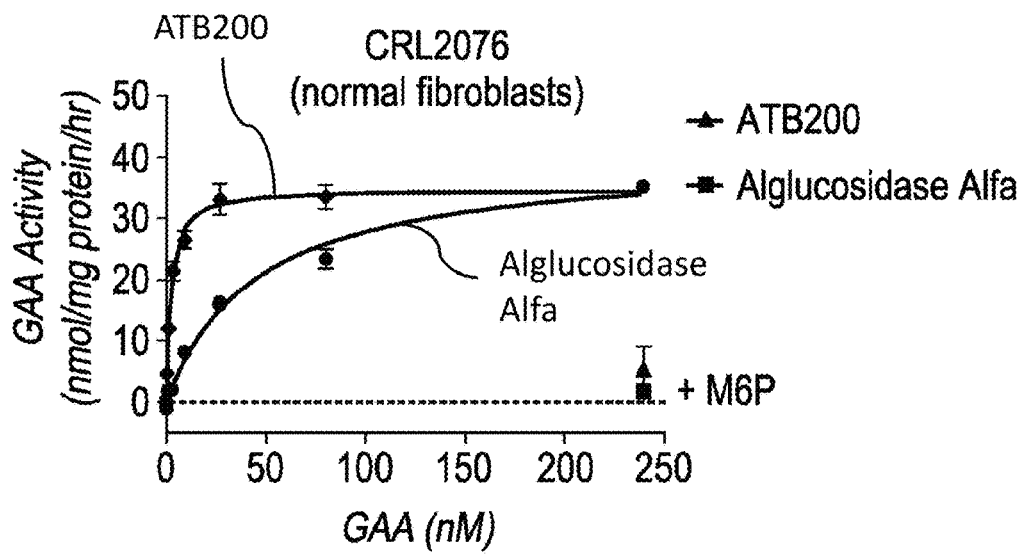
FIG. 13A
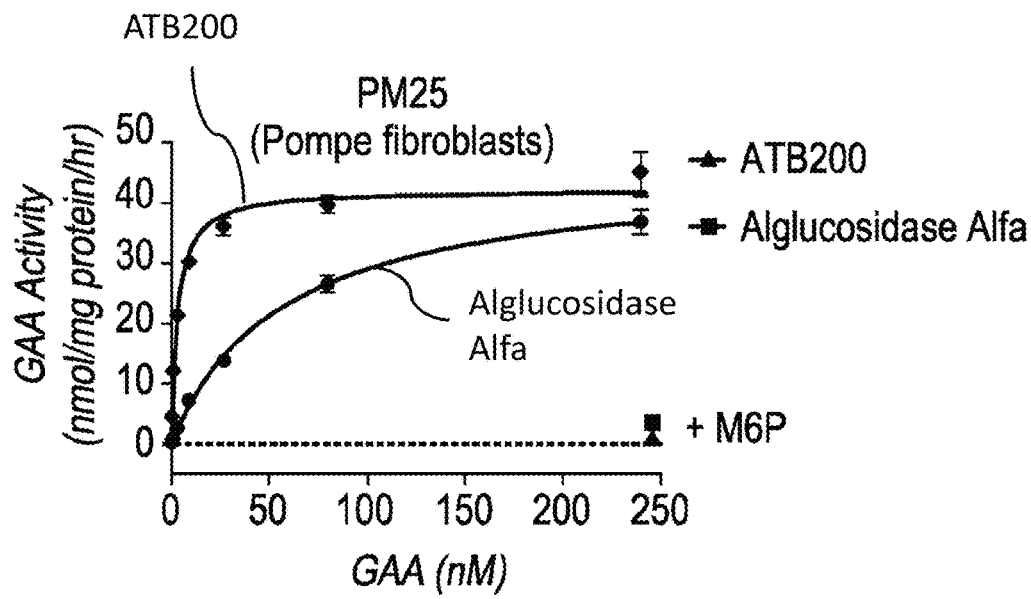
FIG. 13B
| Cell Line | $K_{uptake}$ (nM) | |
|---|---|---|
| | AT200 | Lumizyme |
| normal | 2 | 56 |
| Pompe | 3 | 57 |
FIG. 13C

| Comparison of % glycogen reduction in *Gaa* KO mice after Lumizyme or ATB200 administration (with or without miglustat) | | |
|---|---|---|
| Enzyme ± Chaperone | Quadriceps | Triceps |
| Lumizyme alone (20 mg/kg) | 14 | 14 |
| ATB200 alone (20 mg/kg) | 74 | 62 |
| ATB200 + Miglustat (20 mg/kg) + (10 mg/kg) | 94 | 73 |

A
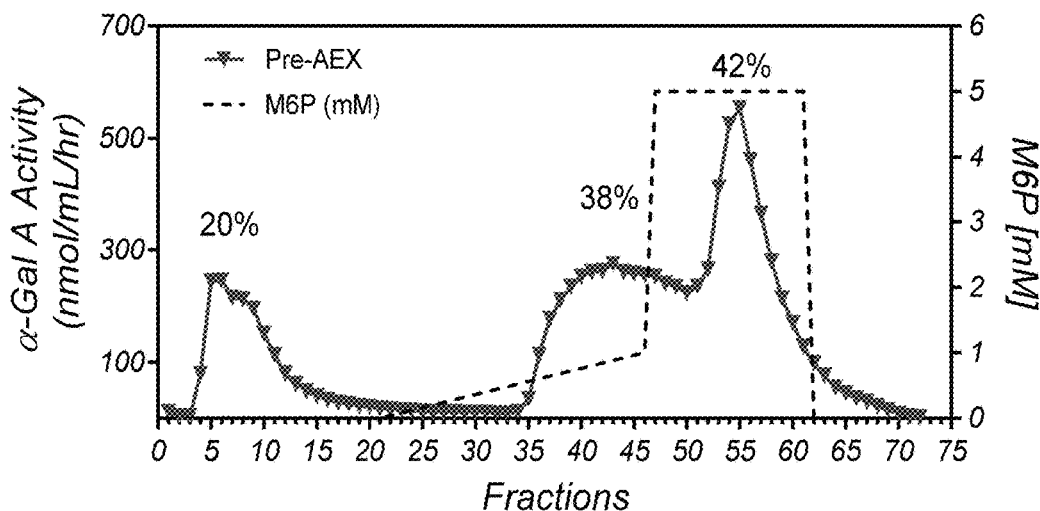
B
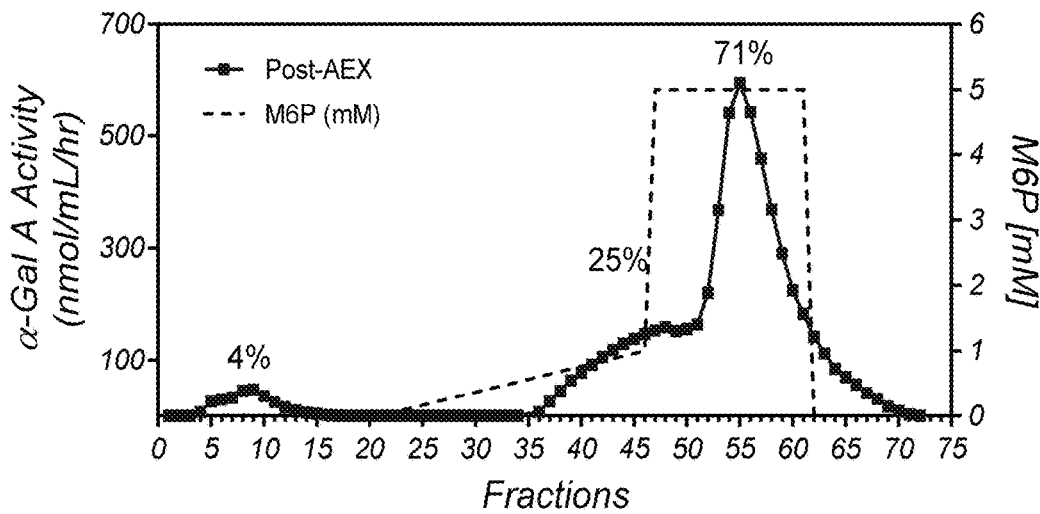
FIG. 20

SEQUENCE LISTING

```
<160> NUMBER OF SEQ ID NOS: 2

<210> SEQ ID NO 1
<211> LENGTH: 952
<212> TYPE: PRT
<213> ORGANISM: Homo sapiens

<400> SEQUENCE: 1

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300
```

```
Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
            325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
            610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720
```

```
Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
        740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
        770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
            850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
        930                 935                 940

Glu Gln Phe Leu Val Ser Trp Cys
945                 950

<210> SEQ ID NO 2
<211> LENGTH: 896
<212> TYPE: PRT
<213> ORGANISM: Homo sapiens

<400> SEQUENCE: 2

Gln Gln Gly Ala Ser Arg Pro Gly Pro Arg Asp Ala Gln Ala His Pro
1               5                   10                  15

Gly Arg Pro Arg Ala Val Pro Thr Gln Cys Asp Val Pro Pro Asn Ser
            20                  25                  30

Arg Phe Asp Cys Ala Pro Asp Lys Ala Ile Thr Gln Glu Gln Cys Glu
        35                  40                  45

Ala Arg Gly Cys Cys Tyr Ile Pro Ala Lys Gln Gly Leu Gln Gly Ala
    50                  55                  60

Gln Met Gly Gln Pro Trp Cys Phe Phe Pro Ser Tyr Pro Ser Tyr
65              70                  75                  80

Lys Leu Glu Asn Leu Ser Ser Ser Glu Met Gly Tyr Thr Ala Thr Leu
                85                  90                  95

Thr Arg Thr Thr Pro Thr Phe Phe Pro Lys Asp Ile Leu Thr Leu Arg
            100                 105                 110

Leu Asp Val Met Met Glu Thr Glu Asn Arg Leu His Phe Thr Ile Lys
        115                 120                 125

Asp Pro Ala Asn Arg Arg Tyr Glu Val Pro Leu Glu Thr Pro Arg Val
    130                 135                 140
```

```
His Ser Arg Ala Pro Ser Pro Leu Tyr Ser Val Glu Phe Ser Glu Glu
145                 150                 155                 160

Pro Phe Gly Val Ile Val His Arg Gln Leu Asp Gly Arg Val Leu Leu
                165                 170                 175

Asn Thr Thr Val Ala Pro Leu Phe Phe Ala Asp Gln Phe Leu Gln Leu
            180                 185                 190

Ser Thr Ser Leu Pro Ser Gln Tyr Ile Thr Gly Leu Ala Glu His Leu
        195                 200                 205

Ser Pro Leu Met Leu Ser Thr Ser Trp Thr Arg Ile Thr Leu Trp Asn
210                 215                 220

Arg Asp Leu Ala Pro Thr Pro Gly Ala Asn Leu Tyr Gly Ser His Pro
225                 230                 235                 240

Phe Tyr Leu Ala Leu Glu Asp Gly Gly Ser Ala His Gly Val Phe Leu
                245                 250                 255

Leu Asn Ser Asn Ala Met Asp Val Val Leu Gln Pro Ser Pro Ala Leu
            260                 265                 270

Ser Trp Arg Ser Thr Gly Gly Ile Leu Asp Val Tyr Ile Phe Leu Gly
        275                 280                 285

Pro Glu Pro Lys Ser Val Val Gln Gln Tyr Leu Asp Val Val Gly Tyr
290                 295                 300

Pro Phe Met Pro Pro Tyr Trp Gly Leu Gly Phe His Leu Cys Arg Trp
305                 310                 315                 320

Gly Tyr Ser Ser Thr Ala Ile Thr Arg Gln Val Val Glu Asn Met Thr
                325                 330                 335

Arg Ala His Phe Pro Leu Asp Val Gln Trp Asn Asp Leu Asp Tyr Met
            340                 345                 350

Asp Ser Arg Arg Asp Phe Thr Phe Asn Lys Asp Gly Phe Arg Asp Phe
        355                 360                 365

Pro Ala Met Val Gln Glu Leu His Gln Gly Gly Arg Arg Tyr Met Met
370                 375                 380

Ile Val Asp Pro Ala Ile Ser Ser Ser Gly Pro Ala Gly Ser Tyr Arg
385                 390                 395                 400

Pro Tyr Asp Glu Gly Leu Arg Arg Gly Val Phe Ile Thr Asn Glu Thr
                405                 410                 415

Gly Gln Pro Leu Ile Gly Lys Val Trp Pro Gly Ser Thr Ala Phe Pro
            420                 425                 430

Asp Phe Thr Asn Pro Thr Ala Leu Ala Trp Trp Glu Asp Met Val Ala
        435                 440                 445

Glu Phe His Asp Gln Val Pro Phe Asp Gly Met Trp Ile Asp Met Asn
450                 455                 460

Glu Pro Ser Asn Phe Ile Arg Gly Ser Glu Asp Gly Cys Pro Asn Asn
465                 470                 475                 480

Glu Leu Glu Asn Pro Pro Tyr Val Pro Gly Val Val Gly Gly Thr Leu
                485                 490                 495

Gln Ala Ala Thr Ile Cys Ala Ser Ser His Gln Phe Leu Ser Thr His
            500                 505                 510

Tyr Asn Leu His Asn Leu Tyr Gly Leu Thr Glu Ala Ile Ala Ser His
        515                 520                 525

Arg Ala Leu Val Lys Ala Arg Gly Thr Arg Pro Phe Val Ile Ser Arg
530                 535                 540

Ser Thr Phe Ala Gly His Gly Arg Tyr Ala Gly His Trp Thr Gly Asp
545                 550                 555                 560
```

-continued

```
Val Trp Ser Ser Trp Glu Gln Leu Ala Ser Ser Val Pro Glu Ile Leu
            565                 570                 575
Gln Phe Asn Leu Leu Gly Val Pro Leu Val Gly Ala Asp Val Cys Gly
            580                 585                 590
Phe Leu Gly Asn Thr Ser Glu Glu Leu Cys Val Arg Trp Thr Gln Leu
            595                 600                 605
Gly Ala Phe Tyr Pro Phe Met Arg Asn His Asn Ser Leu Leu Ser Leu
    610                 615                 620
Pro Gln Glu Pro Tyr Ser Phe Ser Glu Pro Ala Gln Gln Ala Met Arg
625                 630                 635                 640
Lys Ala Leu Thr Leu Arg Tyr Ala Leu Leu Pro His Leu Tyr Thr Leu
            645                 650                 655
Phe His Gln Ala His Val Ala Gly Glu Thr Val Ala Arg Pro Leu Phe
            660                 665                 670
Leu Glu Phe Pro Lys Asp Ser Ser Thr Trp Thr Val Asp His Gln Leu
            675                 680                 685
Leu Trp Gly Glu Ala Leu Leu Ile Thr Pro Val Leu Gln Ala Gly Lys
    690                 695                 700
Ala Glu Val Thr Gly Tyr Phe Pro Leu Gly Thr Trp Tyr Asp Leu Gln
705                 710                 715                 720
Thr Val Pro Ile Glu Ala Leu Gly Ser Leu Pro Pro Pro Pro Ala Ala
            725                 730                 735
Pro Arg Glu Pro Ala Ile His Ser Glu Gly Gln Trp Val Thr Leu Pro
            740                 745                 750
Ala Pro Leu Asp Thr Ile Asn Val His Leu Arg Ala Gly Tyr Ile Ile
            755                 760                 765
Pro Leu Gln Gly Pro Gly Leu Thr Thr Thr Glu Ser Arg Gln Gln Pro
    770                 775                 780
Met Ala Leu Ala Val Ala Leu Thr Lys Gly Gly Glu Ala Arg Gly Glu
785                 790                 795                 800
Leu Phe Trp Asp Asp Gly Glu Ser Leu Glu Val Leu Glu Arg Gly Ala
            805                 810                 815
Tyr Thr Gln Val Ile Phe Leu Ala Arg Asn Asn Thr Ile Val Asn Glu
            820                 825                 830
Leu Val Arg Val Thr Ser Glu Gly Ala Gly Leu Gln Leu Gln Lys Val
            835                 840                 845
Thr Val Leu Gly Val Ala Thr Ala Pro Gln Gln Val Leu Ser Asn Gly
    850                 855                 860
Val Pro Val Ser Asn Phe Thr Tyr Ser Pro Asp Thr Lys Val Leu Asp
865                 870                 875                 880
Ile Cys Val Ser Leu Leu Met Gly Glu Gln Phe Leu Val Ser Trp Cys
            885                 890                 895
```

METHOD FOR SELECTION OF HIGH M6P RECOMBINANT PROTEINS

CROSS-REFERENCE TO RELATED APPLICATIONS

This application claims the benefit under 35 U.S.C. § 119(e) to U.S. Provisional Application No. 62/315,400, filed Mar. 30, 2016, and U.S. Provisional Application No. 62/457,584, filed Feb. 10, 2017, the entire contents of which are incorporated herein by reference in their entirety.

TECHNICAL FIELD

Principles and embodiments of the present invention relate generally to the manufacturing of recombinant proteins, particularly lysosomal enzymes that have a high content of mannose-6-phosphate.

BACKGROUND

Lysosomal storage disorders are a group of autosomal recessive genetic diseases characterized by the accumulation of cellular glycosphingolipids, glycogen, or mucopolysaccharides within intracellular compartments called lysosomes. Individuals with these diseases carry mutant genes coding for enzymes which are defective in catalyzing the hydrolysis of one or more of these substances, which then build up in the lysosomes. For example, Pompe disease, also known as acid maltase deficiency or glycogen storage disease type II, is one of several lysosomal storage disorders. Other examples of lysosomal disorders include Gaucher disease, GM1-gangliosidosis, fucosidosis, mucopolysaccharidoses, Hurler-Scheie disease, Niemann-Pick A and B diseases, and Fabry disease. Pompe disease is also classified as a neuromuscular disease or a metabolic myopathy.

Pompe disease is estimated to occur in about 1 in 40,000 births, and is caused by a mutation in the GAA gene, which codes for the enzyme lysosomal α-glucosidase (EC: 3.2.1.20), also commonly known as acid α-glucosidase. Acid α-glucosidase is involved in the metabolism of glycogen, a branched polysaccharide which is the major storage form of glucose in animals, by catalyzing its hydrolysis into glucose within the lysosomes. Because individuals with Pompe disease produce mutant, defective acid α-glucosidase which is inactive or has reduced activity, glycogen breakdown occurs slowly or not at all, and glycogen accumulates in the lysosomes of various tissues, particularly in striated muscles, leading to a broad spectrum of clinical manifestations, including progressive muscle weakness and respiratory insufficiency. Tissues such as the heart and skeletal muscles are particularly affected.

Pompe disease can vary widely in the degree of enzyme deficiency, severity and age of onset, and over 500 different mutations in the GAA gene have been identified, many of which cause disease symptoms of varying severity. The disease has been classified into broad types: early onset or infantile and late onset. Earlier onset of disease and lower enzymatic activity are generally associated with a more severe clinical course. Infantile Pompe disease is the most severe, resulting from complete or near complete acid α-glucosidase deficiency, and presents with symptoms that include severe lack of muscle tone, weakness, enlarged liver and heart, and cardiomyopathy. The tongue may become enlarged and protrude, and swallowing may become difficult. Most affected children die from respiratory or cardiac complications before the age of two. Late onset Pompe disease can present at any age older than 12 months and is characterized by a lack of cardiac involvement and better short-term prognosis. Symptoms are related to progressive skeletal muscle dysfunction, and involve generalized muscle weakness and wasting of respiratory muscles in the trunk, proximal lower limbs, and diaphragm. Some adult patients are devoid of major symptoms or motor limitations. Prognosis generally depends on the extent of respiratory muscle involvement. Most subjects with Pompe disease eventually progress to physical debilitation requiring the use of a wheelchair and assisted ventilation, with premature death often occurring due to respiratory failure.

Recent treatment options for Pompe disease include enzyme replacement therapy (ERT) with recombinant human acid α-glucosidase (rhGAA). Conventional rhGAA products are known under the names alglucosidase alfa, Myozyme® or Lumizyme®, from Genzyme, Inc. ERT is a chronic treatment required throughout the lifetime of the patient, and involves administering the replacement enzyme by intravenous infusion. The replacement enzyme is then transported in the circulation and enters lysosomes within cells, where it acts to break down the accumulated glycogen, compensating for the deficient activity of the endogenous defective mutant enzyme, and thus relieving the disease symptoms. In subjects with infantile onset Pompe disease, treatment with alglucosidase alfa has been shown to significantly improve survival compared to historical controls, and in late onset Pompe disease, alglucosidase alfa has been shown to have a statistically significant, if modest, effect on the 6-Minute Walk Test (6MWT) and forced vital capacity (FVC) compared to placebo.

However, the majority of subjects either remain stable or continue to deteriorate while undergoing treatment with alglucosidase alfa. The reason for the apparent sub-optimal effect of ERT with alglucosidase alfa is unclear, but could be partly due to the progressive nature of underlying muscle pathology, or the poor tissue targeting of the current ERT. For example, the infused enzyme is not stable at neutral pH, including at the pH of plasma (about pH 7.4), and can be irreversibly inactivated within the circulation. Furthermore, infused alglucosidase alfa shows insufficient uptake in key disease-relevant muscles, possibly due to inadequate glycosylation with mannose-6-phosphate (M6P) residues. Such residues bind cation-independent mannose-6-phosphate receptors (CIMPR) at the cell surface, allowing the enzyme to enter the cell and the lysosomes within. Therefore, high doses of the enzyme may be required for effective treatment so that an adequate amount of active enzyme can reach the lysosomes, making the therapy costly and time-consuming.

There are seven potential N-linked glycosylation sites on rhGAA. Since each glycosylation site is heterogeneous in the type of N-linked oligosaccharides (N-glycans) present, rhGAA consist of a complex mixture of proteins with N-glycans having varying binding affinities for M6P receptor and other carbohydrate receptors. rhGAA that contains a high mannose N-glycans having one M6P group (mono-M6P) binds to CIMPR with low (~6,000 nM) affinity while rhGAA that contains two M6P groups on same N-glycan (bis-M6P) bind with high (~2 nM) affinity. Representative structures for non-phosphorylated, mono-M6P, and bis-M6P glycans are shown by FIG. 1A. The mannose-6-P group is shown by FIG. 1B. Once inside the lysosome, rhGAA can enzymatically degrade accumulated glycogen. However, conventional rhGAAs have low total levels of M6P- and bis-M6P bearing glycans and, thus, target muscle cells poorly resulting in inferior delivery of rhGAA to the lysosomes. Productive drug targeting of rhGAA is shown in FIG.

2A. The majority of rhGAA molecules in these conventional products do not have phosphorylated N-glycans, thereby lacking affinity for the CIMPR. Non-phosphorylated high mannose glycans can also be cleared by the mannose receptor which results in non-productive clearance of the ERT (FIG. 2B).

The other type of N-glycans, complex carbohydrates, which contain galactose and sialic acids, are also present on rhGAA. Since complex N-glycans are not phosphorylated they have no affinity for CIMPR. However, complex-type N-glycans with exposed galactose residues have moderate to high affinity for the asialoglycoprotein receptor on liver hepatocytes which leads to rapid non-productive clearance of rhGAA (FIG. 2B).

Current manufacturing processes used to make conventional rhGAA, such as Myozyme®, Lumizyme® or alglucosidase alfa, have not significantly increased the content of M6P or bis-M6P because cellular carbohydrate processing is naturally complex and extremely difficult to manipulate. Accordingly, there remains a need for further improvements to enzyme replacement therapy for treatment of Pompe disease, such as new manufacturing, capturing and purification processes for rhGAA.

Similarly, other recombinant proteins that are targeted to the lysosome, such as other lysosomal enzymes, also bind CIMPR. However, current manufacturing processes used to make other conventional recombinant proteins that are targeted to lysosomes do not provide recombinant proteins with a high content of M6P or bis-M6P. Accordingly, there remains a need for further improvements in the manufacturing, capturing and purification processes for these other recombinant proteins as well.

SUMMARY

One aspect of the present invention is related to a method for producing recombinant human lysosomal proteins. In various embodiments of this aspect, the method comprises culturing host cells in a bioreactor that secrete a recombinant human lysosomal protein, removing media from the bioreactor, filtering the media to provide a filtrate, loading the filtrate onto an anion exchange chromatography (AEX) column to capture the lysosomal protein and eluting a first protein product from the AEX column.

In one or more embodiments, the recombinant human lysosomal protein is recombinant human α-glucosidase (rhGAA). In one or more embodiments, the rhGAA comprises an amino acid sequence that is at least 95% identical to SEQ ID NO: 2.

In one or more embodiments, the method further comprises loading the first protein product onto a chromatography column, and eluting a second protein product from the column. In some embodiments, the column is an immobilized metal affinity chromatography (IMAC) column In one or more embodiments, the method further comprises loading the second protein product onto a chromatography column, and eluting a third protein product from the chromatography column. In some embodiments, the third chromatography column is selected from a cation exchange chromatography (CEX) column and a size exclusion chromatography (SEC) column.

In one or more embodiments, filtering the media is selected from alternating tangential flow filtration (ATF) and tangential flow filtration (TFF).

In one or more embodiments, the method further comprises inactivating viruses in one or more of the first protein product, the second protein product and the third protein product.

In one or more embodiments, the method further comprises filtering the second protein product or the third protein product to provide a filtered product and filling a vial with the filtered product. In one or more embodiments, the method further comprises lyophilizing the filtered product.

In one or more embodiments, the host cells comprise Chinese hamster ovary (CHO) cells. In some embodiments, the host cells comprise CHO cell line GA-ATB-200 or ATB-200-X5-14 or a subculture thereof.

In one or more embodiments, (i) at least 90% of the first protein product or the second protein product or the third protein product binds to cation-independent manose-6-phosphate receptor (CIMPR) or (ii) at least 90% of the first protein product or the second protein product or the third protein product contains an N-glycan carrying mono-mannose-6-phosphate (mono-M6P) or bis-mannose-6-phosphate (bis-M6P).

In one or more embodiments, the recombinant human lysosomal protein is rhGAA comprising seven potential N-glycosylation sites, at least 50% of molecules of the rhGAA comprise an N-glycan unit bearing two mannose-6-phosphate residues at the first site, at least 30% of molecules of the rhGAA comprise an N-glycan unit bearing one mannose-6-phosphate residue at the second site, at least 30% of molecules of the rhGAA comprise an N-glycan unit bearing two mannose-6-phosphate residue at the fourth site, and at least 20% of molecules of the rhGAA comprise an N-glycan unit bearing one mannose-6-phosphate residue at the fourth site.

Another aspect of the present invention is related to a recombinant protein product made by any of the methods described herein.

Another aspect of the present invention is related to pharmaceutical composition comprising the recombinant protein product and a pharmaceutically acceptable carrier.

Yet another aspect of the present invention is related to a method for treating a lysosomal storage disorder, the method comprising administering the pharmaceutical composition to a patient in need thereof.

In one or more embodiments, the lysosomal storage disorder is Pompe disease and the recombinant protein is rhGAA. In one or more embodiments, the patient is co-administered a pharmacological chaperone for α-glucosidase within 4 hours of the administration of the pharmaceutical composition comprising the rhGAA product. In some embodiments, the pharmacological chaperone is selected from 1-deoxynojirimycin and N-butyl-deoxynojirimycin. In some embodiments, the pharmacological chaperone is co-formulated with the rhGAA product.

Various embodiments are listed below. It will be understood that the embodiments listed below may be combined not only as listed below, but in other suitable combinations in accordance with the scope of the invention.

BRIEF DESCRIPTION OF THE DRAWINGS

Further features of the present invention will become apparent from the following written description and the accompanying figures, in which:

FIG. 3A graphically depicts a CIMPR receptor (also known as an IGF2 receptor) and domains of this receptor.

FIG. 3B is a table showing binding affinity (nmolar) of glycans bearing bis- and mono-M6P for CIMPR, the binding affinity of high mannose-type glycans to mannose receptors, and the binding affinity of desialylated complex glycan for asialyoglycoprotein receptors. RhGAA that has glycans bearing M6P and bis-M6P can productively bind to CIMPR on muscle.

As shown in FIG. 2A, 78% of the GAA activity in Lumizyme® eluted prior to addition of M6P. FIG. 2B shows that 73% of the GAA Myozyme® activity eluted prior to addition of M6P. Only 22% or 27% of the rhGAA in Lumizyme® or Myozyme®, respectively, was eluted with M6P. These figures show that most of the rhGAA in these two conventional rhGAA products lack glycans having M6P needed to target CIMPR in target muscle tissues.

FIG. 8 is a graph showing the results of CIMPR affinity chromatography of ATB200 rhGAA with and without capture on an anion exchange (AEX) column.

FIG. 10 is a table showing a summary of N-glycan structures of Lumizyme® compared to three different preparations of ATB200 rhGAA, identified as BP-rhGAA, ATB200-1 and ATB200-2.

FIG. 13A is a graph comparing ATB200 rhGAA activity (left trace) with Lumizyme® rhGAA activity (right trace) inside normal fibroblasts at various GAA concentrations.

FIG. 13B is a table comparing ATB200 rhGAA activity (left trace) with Lumizyme® rhGAA activity (right trace) inside fibroblasts from a subject having Pompe Disease at various GAA concentrations.

FIG. 13C is a table comparing $K_{uptake}$ of fibroblasts from normal subjects and subjects with Pompe Disease.

FIGS. 20A and 20B, respectively, are graphs showing the results of CIMPR affinity chromatography of recombinant α-galactosidase A (rhα-Gal A) enzyme before and after capture and purification on an anion exchange (AEX) column.

DETAILED DESCRIPTION

Figure 1A:
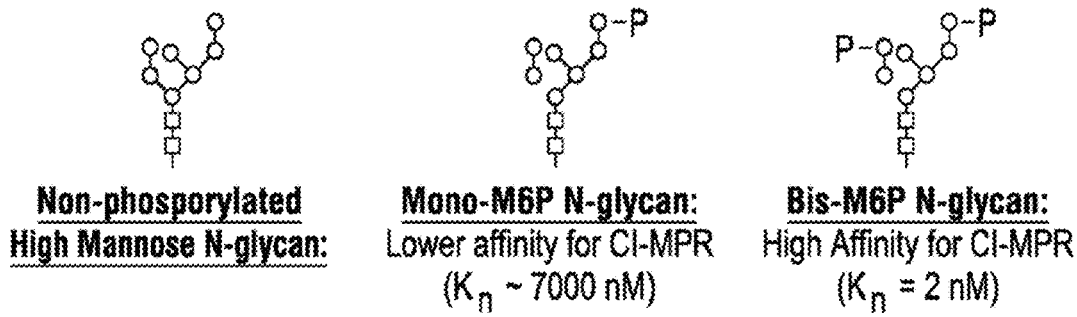
FIG. 1A shows non-phosphorylated high mannose glycan, a mono-M6P glycan, and a bis-M6P glycan.
Figure 1B:
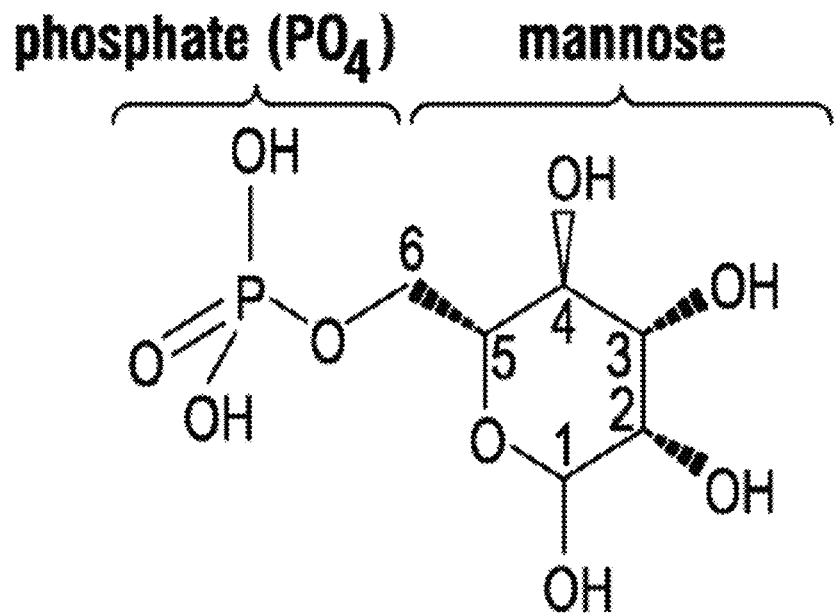
FIG. 1B shows the chemical structure of the M6P group.
Figures 2A, 2B:
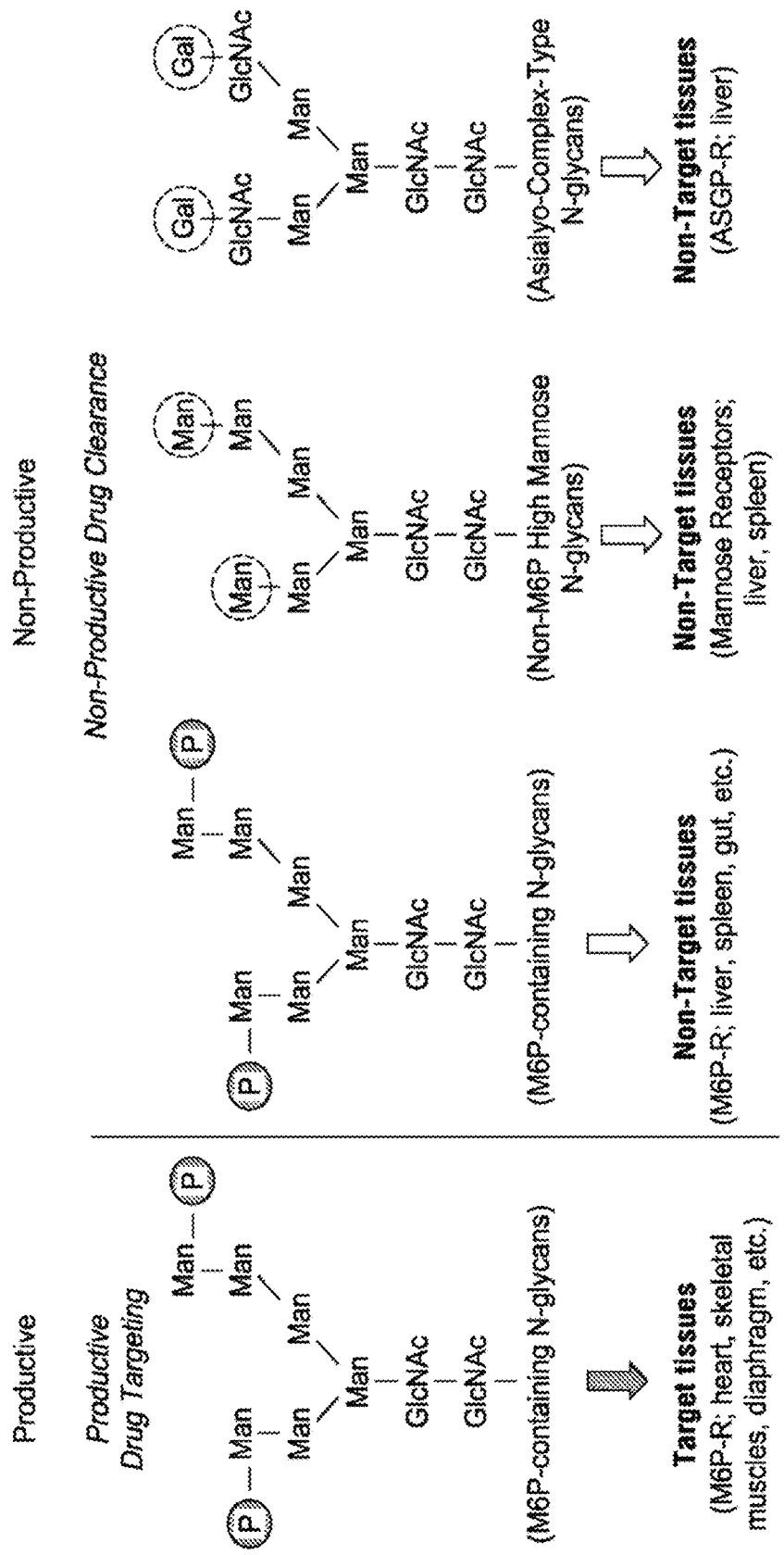
FIG. 2A describes productive targeting of rhGAA via glycans bearing M6P to target tissues (e.g. muscle tissues of subject with Pompe Disease).
FIG. 2B describes non-productive drug clearance to non-target tissues (e.g. liver and spleen) or by binding of non-M6P glycans to non-target tissues.

Before describing several exemplary embodiments of the invention, it is to be understood that the invention is not limited to the details of construction or process steps set forth in the following description. The invention is capable of other embodiments and of being practiced or being carried out in various ways.

Although specific reference is made to GAA, it will be understood by a person having ordinary skill in the art that the methods described herein may be used to produce, capture and purify other recombinant proteins that target the lysosome, including but not limited to the lysosomal enzyme α-galactosidase A.

Various aspects of the invention pertain to new methods for the production, capturing and purification of recombinant human lysosomal proteins, such as recombinant human acid α-glucosidase (rhGAA). Other aspects of the invention pertain to recombinant proteins produced by the processes described herein, as well as pharmaceutical compositions, methods of treatment, and uses of such recombinant proteins.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

As used herein, the term "lysosomal protein" refers to any protein that is targeted to the lysosome, such as a lysosomal enzyme. Examples of lysosomal enzymes and the associated disease are provided in Table 1 below:

TABLE 1

| Lysosomal Enzyme | Disease |
| --- | --- |
| Acid α-glucosidase | Pompe disease |
| α-galactosidase A | Fabry disease |
| Acid β-glucosidase | Gaucher disease |
| α-L-iduronidase | Hurler-Scheie disease |
| Iduronate sulfatase | Hunter disease |
| β-galactosidase | GM1-gangliosidosis; Morquio disease B |
| β-glucuronidase | Sly disease (MPS VI) |
| α-fucosidase | Fucosidosis |
| Acid sphingomyelinase | Niemann-Pick A and B |
| β-hexosaminidase A | Tay Sachs disease |
| β-hexosaminidase B | Sandhoff disease |
| β-galactocerebrosidase | Krabbe disease |
| Acid ceramidase | Farber disease |
| Heparan-N-sulfatase | Sanfilippo disease A (MPS IIIa) |
| α-N-acetyl-glucosaminidase | Sanfilippo disease B (MPS IIIb) |
| α-glucosaminide N-acetyltransferase | Sanfilippo disease C (MPS IIIc) |
| N-acetylglucosamine-6-sulfate sulfatase | Sanfilippo disease D (MPS IIId) |
| N-acetylgalactosamine-6-sulfate sulfatase | Morquio disease A (MPS Ivb) |
| Arylsulfatase A | Metachromatic leukodystrophy |
| Arylsulfatase B | Maroteaux-Lamy (MPS VI) |
| Acid lipase | Wolf disease |
| acid α-mannosidase | α-mannosidosis |
| acid β-mannosidase | β-mannosidosis |
| α-N-acetyl-neuraminidase | Sialidosis |
| α-N-acetylgalactosaminidase | Schindler-Kanzaki disease |
| N-aspartyl-β-glucosaminidase | Aspartylglucosaminuria |

As used herein, the term "Pompe disease," also referred to as acid maltase deficiency, glycogen storage disease type II (GSDII), and glycogenosis type II, is intended to refer to a genetic lysosomal storage disorder characterized by mutations in the GAA gene, which codes for the human acid α-glucosidase enzyme. The term includes but is not limited to early and late onset forms of the disease, including but not limited to infantile, juvenile and adult-onset Pompe disease.

As used herein, the term "acid α-glucosidase" is intended to refer to a lysosomal enzyme which hydrolyzes α-1,4 linkages between the D-glucose units of glycogen, maltose, and isomaltose. Alternative names include but are not limited to lysosomal α-glucosidase (EC:3.2.1.20); glucoamylase; 1,4-α-D-glucan glucohydrolase; amyloglucosidase; gamma-amylase and exo-1,4-α-glucosidase. Human acid α-glucosidase is encoded by the GAA gene (National Centre for Biotechnology Information (NCBI) Gene ID 2548), which has been mapped to the long arm of chromosome 17 (location 17q25.2-q25.3). More than 500 mutations have currently been identified in the human GAA gene, many of which are associated with Pompe disease. Mutations resulting in misfolding or misprocessing of the acid α-glucosidase enzyme include T1064C (Leu355Pro) and C2104T (Arg702Cys). In addition, GAA mutations which affect maturation and processing of the enzyme include Leu405Pro and Met519Thr. The conserved hexapeptide WIDMNE at amino acid residues 516-521 is required for activity of the acid α-glucosidase protein. As used herein, the abbreviation "GAA" is intended to refer to the acid α-glucosidase enzyme, while the italicized abbreviation "GAA" is intended to refer to the human gene coding for the human acid α-glucosidase enzyme The italicized abbreviation "Gaa" is intended to refer to non-human genes coding for non-human acid α-glucosidase enzymes, including but not limited to rat or mouse genes, and the abbreviation "Gaa" is intended to refer to non-human acid α-glucosidase enzymes. Thus, the abbreviation "rhGAA" is intended to refer to the recombinant human acid α-glucosidase enzyme.

As used herein, the term "alglucosidase alfa" is intended to refer to a recombinant human acid α-glucosidase identified as [199-arginine,223-histidine]prepro-α-glucosidase (human); Chemical Abstracts Registry Number 420794-05-0. Alglucosidase alfa is approved for marketing in the United States by Genzyme, as of January 2016, as the products Lumizyme® and Myozyme®.

As used herein, the term "ATB200" is intended to refer to a recombinant human acid α-glucosidase described in co-pending patent application PCT/US2015/053252, the disclosure of which is herein incorporated by reference.

As used herein, the term "glycan" is intended to refer to a polysaccharide chain covalently bound to an amino acid residue on a protein or polypeptide. As used herein, the term "N-glycan" or "N-linked glycan" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans can contain one or several monosaccharide units, and the monosaccharide units can be covalently linked to form a straight chain or a branched chain. In at least one embodiment, N-glycan units attached to ATB200 can comprise one or more monosaccharide units each independently selected from N-acetylglucosamine, mannose, galactose or sialic acid. The N-glycan units on the protein can be determined by any appropriate analytical technique, such as mass spectrometry. In some embodiments, the N-glycan units can be determined by liquid chromatography-tandem mass spectrometry (LC-MS/MS) utilizing an instrument such as the Thermo Scientific Orbitrap Velos Pro™ Mass Spectrometer, Thermo Scientific Orbitrap Fusion Lumos Tribid™ Mass Spectrometer or Waters Xevo® G2-XS QT of Mass Spectrometer.

As used herein, the term "high-mannose N-glycan" is intended to refer to an N-glycan having one to six or more mannose units. In at least one embodiment, a high mannose N-glycan unit can contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position; i.e. having a phosphate group bonded to the hydroxyl group at the 6 position. In at least one embodiment, one or more mannose units of one or more N-glycan units are phosphorylated at the 6 position to form mannose-6-phosphate units. In at least one embodiment, the term "M6P" or "mannose-6-phosphate" refers to both a mannose phosphodiester having N-acetylglucosamine (GlcNAc) as a "cap" on the phosphate group, as well as a mannose unit having an exposed phosphate group lacking the GlcNAc cap. In at least one embodiment, the N-glycans of a protein can have multiple M6P groups, with at least one M6P group having a GlcNAc cap and at least one other M6P group lacking a GlcNAc cap.

As used herein, the term "complex N-glycan" is intended to refer to an N-glycan containing one or more galactose and/or sialic acid units. In at least one embodiment, a complex N-glycan can be a high-mannose N-glycan in which one or mannose units are further bonded to one or more monosaccharide units each independently selected from N-acetylglucosamine, galactose and sialic acid.

As used herein, the compound miglustat, also known as N-butyl-1-deoxynojirimycin NB-DNJ or (2R,3R,4R,5S)-1-butyl-2-(hydroxymethyl)piperidine-3,4,5-triol, is a compound having the following chemical formula:

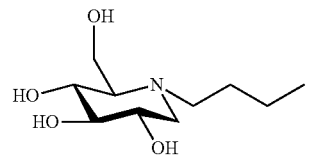

One formulation of miglustat is marketed commercially under the trade name Zavesca® as monotherapy for type 1 Gaucher disease.

As discussed below, pharmaceutically acceptable salts of miglustat may also be used in the present invention. When a salt of miglustat is used, the dosage of the salt will be adjusted so that the dose of miglustat received by the patient is equivalent to the amount which would have been received had the miglustat free base been used.

As used herein, the compound duvoglustat, also known as 1-deoxynojirimycin or DNJ or (2R,3R,4R,5S)-2-(hydroxymethyl)piperidine-3,4,5-triol, is a compound having the following chemical formula:

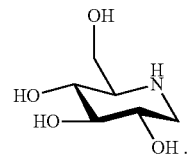

When a salt of duvoglustat is used, the dosage of the salt will be adjusted so that the dose of duvoglustat received by the patient is equivalent to the amount which would have been received had the duvoglustat free base been used.

As used herein, the term "pharmacological chaperone" or sometimes simply the term "chaperone" is intended to refer to a molecule that specifically binds to a lysosomal protein and has one or more of the following effects:

enhances the formation of a stable molecular conformation of the protein;

enhances proper trafficking of the protein from the endoplasmic reticulum to another cellular location, preferably a native cellular location, so as to prevent endoplasmic reticulum-associated degradation of the protein;

prevents aggregation of conformationally unstable or misfolded proteins;

restores and/or enhances at least partial wild-type function, stability, and/or activity of the protein; and/or improves the phenotype or function of the cell harboring the protein.

Thus, a pharmacological chaperone for acid α-glucosidase is a molecule that binds to acid α-glucosidase, resulting in proper folding, trafficking, non-aggregation, and activity of acid α-glucosidase. As used herein, this term includes but is not limited to active site-specific chaperones (ASSCs) which bind in the active site of the enzyme, inhibitors or antagonists, and agonists. In at least one embodiment, the pharmacological chaperone can be an inhibitor or antagonist of acid α-glucosidase. As used herein, the term "antagonist" is intended to refer to any molecule that binds to acid α-glucosidase and either partially or completely blocks, inhibits, reduces, or neutralizes an activity of acid α-glucosidase. In at least one embodiment, the pharmacological chaperone is miglustat. Another non-limiting example of a pharmacological chaperone for acid α-glucosidase is duvoglustat.

As used herein, the term "active site" is intended to refer to a region of a protein that is associated with and necessary for a specific biological activity of the protein. In at least one embodiment, the active site can be a site that binds a substrate or other binding partner and contributes the amino acid residues that directly participate in the making and breaking of chemical bonds.

As used herein, the "therapeutically effective dose" and "effective amount" are intended to refer to an amount of recombinant human lysosomal protein (e.g. rhGAA) and/or of chaperone and/or of a combination thereof, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Pompe disease such as those known in the art. Symptoms or markers of Pompe disease include but are not limited to decreased acid α-glucosidase tissue activity; cardiomyopathy; cardiomegaly; progressive muscle weakness, especially in the trunk or lower limbs; profound hypotonia; macroglossia (and in some cases, protrusion of the tongue); difficulty swallowing, sucking, and/or feeding; respiratory insufficiency; hepatomegaly (moderate); laxity of facial muscles; areflexia; exercise intolerance; exertional dyspnea; orthopnea; sleep apnea; morning headaches; somnolence; lordosis and/or scoliosis; decreased deep tendon reflexes; lower back pain; and failure to meet developmental motor milestones. It should be noted that a concentration of chaperone (e.g. miglustat) that has an inhibitory effect on acid α-glucosidase may constitute an "effective amount" for purposes of this invention because of dilution (and consequent shift in binding due to the change in equilibrium), bioavailability and metabolism of the chaperone upon administration in vivo.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "combination therapy" is intended to refer to any therapy wherein two or more individual therapies are administered concurrently or consecutively. In at least one embodiment, the results of the combination therapy are enhanced as compared to the effect of each therapy when it is performed individually. Enhancement may include any improvement of the effect of the various therapies that may result in an advantageous result as compared to the results achieved by the therapies when performed alone. Enhanced effect or results can include a synergistic enhancement, wherein the enhanced effect is more than the additive effects of each therapy when performed by itself; an additive enhancement, wherein the enhanced effect is substantially equal to the additive effect of each therapy when performed by itself; or less than a synergistic effect, wherein the enhanced effect is lower than the additive effect of each therapy when performed by itself, but still better than the effect of each therapy when performed by itself. Enhanced effect may be measured by any means known in the art by which treatment efficacy or outcome can be measured.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the term "carrier" is intended to refer to a diluent, adjuvant, excipient, or vehicle with which a compound is administered. Suitable pharmaceutical carriers are known in the art and, in at least one embodiment, are described in "Remington's Pharmaceutical Sciences" by E. W. Martin, 18th Edition, or other editions.

As used herein, the terms "subject" or "patient" are intended to refer to a human or non-human animal. In at least one embodiment, the subject is a mammal. In at least one embodiment, the subject is a human.

As used herein, the term "anti-drug antibody" is intended to refer to an antibody specifically binding to a drug administered to a subject and generated by the subject as at least part of a humoral immune response to administration of the drug to the subject. In at least one embodiment the drug is a therapeutic protein drug product. The presence of the anti-drug antibody in the subject can cause immune responses ranging from mild to severe, including but not limited to life-threatening immune responses which include but are not limited to anaphylaxis, cytokine release syndrome and cross-reactive neutralization of endogenous proteins mediating critical functions. In addition or alternatively, the presence of the anti-drug antibody in the subject can decrease the efficacy of the drug.

As used herein, the term "neutralizing antibody" is intended to refer to an anti-drug antibody acting to neutralize the function of the drug. In at least one embodiment, the therapeutic protein drug product is a counterpart of an endogenous protein for which expression is reduced or absent in the subject. In at least one embodiment, the neutralizing antibody can act to neutralize the function of the endogenous protein.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "concurrently" as used herein is intended to mean at the same time as or within a reasonably short period of time before or after, as will be understood by those skilled in the art. For example, if two treatments are administered concurrently with each other, one treatment can be administered before or after the other treatment, to allow for time needed to prepare for the later of the two treatments. Therefore "concurrent administration" of two treatments includes but is not limited to one treatment following the other by 20 minutes or less, about 20 minutes, about 15 minutes, about 10 minutes, about 5 minutes, about 2 minutes, about 1 minute or less than 1 minute.

The term "pharmaceutically acceptable salt" as used herein is intended to mean a salt which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19, herein incorporated by reference.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like.

ATB200 rhGAA

In at least one embodiment, the recombinant human lysosomal protein (e.g. rhGAA) is expressed in Chinese hamster ovary (CHO) cells and comprises an increased content of N-glycan units bearing one or more mannose-6-phosphate residues when compared to a content of N-glycan units bearing one or more mannose-6-phosphate residues of a conventional recombinant human lysosomal protein such as alglucosidase alfa. In at least one embodiment, the acid α-glucosidase is a recombinant human acid α-glucosidase referred to herein as ATB200, as described in co-pending international patent application PCT/US2015/053252. ATB200 has been shown to bind cation-independent mannose-6-phosphate receptors (CIMPR) with high affinity ($K_D$~2-4 nM) and to be efficiently internalized by Pompe fibroblasts and skeletal muscle myoblasts ($K_{uptake}$~7-14 nM). ATB200 was characterized in vivo and shown to have a shorter apparent plasma half-life ($t_{1/2}$~45 min) than alglucosidase alfa ($t_{1/2}$~60 min).

In at least one embodiment, the recombinant human acid α-glucosidase is an enzyme having an amino acid sequence as set forth in SEQ ID NO: 1 or SEQ ID NO: 2.

```
SEQ ID NO: 1    Met Gly Val Arg His Pro Pro Cys Ser His Arg Leu Leu Ala Val Cys
                Ala Leu Val Ser Leu Ala Thr Ala Ala Leu Leu Gly His Ile Leu Leu
                His Asp Phe Leu Leu Val Pro Arg Glu Leu Ser Gly Ser Ser Pro Val
                Leu Glu Glu Thr His Pro Ala His Gln Gln Gly Ala Ser Arg Pro Gly
                Pro Arg Asp Ala Gln Ala His Pro Gly Arg Pro Arg Ala Val Pro Thr
                Gln Cys Asp Val Pro Pro Asn Ser Arg Phe Asp Cys Ala Pro Asp Lys
                Ala Ile Thr Gln Glu Gln Cys Glu Ala Arg Gly Cys Cys Tyr Ile Pro
                Ala Lys Gln Gly Leu Gln Gly Ala Gln Met Gly Gln Pro Trp Cys Phe
                Phe Pro Pro Ser Tyr Pro Ser Tyr Lys Leu Glu Asn Leu Ser Ser Ser
                Glu Met Gly Tyr Thr Ala Thr Leu Thr Arg Thr Thr Pro Thr Phe Phe
                Pro Lys Asp Ile Leu Thr Leu Arg Leu Asp Val Met Met Glu Thr Glu
                Asn Arg Leu His Phe Thr Ile Lys Asp Pro Ala Asn Arg Arg Tyr Glu
                Val Pro Leu Glu Thr Pro Arg Val His Ser Arg Ala Pro Ser Pro Leu
                Tyr Ser Val Glu Phe Ser Glu Glu Pro Phe Gly Val Ile Val His Arg
                Gln Leu Asp Gly Arg Val Leu Leu Asn Thr Thr Val Ala Pro Leu Phe
                Phe Ala Asp Gln Phe Leu Gln Leu Ser Thr Ser Leu Pro Ser Gln Tyr
                Ile Thr Gly Leu Ala Glu His Leu Ser Pro Leu Met Leu Ser Thr Ser
                Trp Thr Arg Ile Thr Leu Trp Asn Arg Asp Leu Ala Pro Thr Pro Gly
                Ala Asn Leu Tyr Gly Ser His Pro Phe Tyr Leu Ala Leu Glu Asp Gly
                Gly Ser Ala His Gly Val Phe Leu Leu Asn Ser Asn Ala Met Asp Val
                Val Leu Gln Pro Ser Pro Ala Leu Ser Trp Arg Ser Thr Gly Gly Ile
```

-continued

```
            Leu Asp Val Tyr Ile Phe Leu Gly Pro Glu Pro Lys Ser Val Val Gln
            Gln Tyr Leu Asp Val Val Gly Tyr Pro Phe Met Pro Pro Tyr Trp Gly
            Leu Gly Phe His Leu Cys Arg Trp Gly Tyr Ser Ser Thr Ala Ile Thr
            Arg Gln Val Val Glu Asn Met Thr Arg Ala His Phe Pro Leu Asp Val
            Gln Trp Asn Asp Leu Asp Tyr Met Asp Ser Arg Arg Asp Phe Thr
            Phe Asn Lys Asp Gly Phe Arg Asp Phe Pro Ala Met Val Gln Glu
            Leu His Gln Gly Gly Arg Arg Tyr Met Met Ile Val Asp Pro Ala Ile
            Ser Ser Ser Gly Pro Ala Gly Ser Tyr Arg Pro Tyr Asp Glu Gly Leu
            Arg Arg Gly Val Phe Ile Thr Asn Glu Thr Gly Gln Pro Leu Ile Gly
            Lys Val Trp Pro Gly Ser Thr Ala Phe Pro Asp Phe Thr Asn Pro Thr
            Ala Leu Ala Trp Trp Glu Asp Met Val Ala Glu Phe His Asp Gln Val
            Pro Phe Asp Gly Met Trp Ile Asp Met Asn Glu Pro Ser Asn Phe Ile
            Arg Gly Ser Glu Asp Gly Cys Pro Asn Asn Glu Leu Glu Asn Pro Pro
            Tyr Val Pro Gly Val Val Gly Gly Thr Leu Gln Ala Ala Thr Ile Cys
            Ala Ser Ser His Gln Phe Leu Ser Thr His Tyr Asn Leu His Asn Leu
            Tyr Gly Leu Thr Glu Ala Ile Ala Ser His Arg Ala Leu Val Lys Ala
            Arg Gly Thr Arg Pro Phe Val Ile Ser Arg Ser Thr Phe Ala Gly His
            Gly Arg Tyr Ala Gly His Trp Thr Gly Asp Val Trp Ser Ser Trp Glu
            Gln Leu Ala Ser Ser Val Pro Glu Ile Leu Gln Phe Asn Leu Leu Gly
            Val Pro Leu Val Gly Ala Asp Val Cys Gly Phe Leu Gly Asn Thr Ser
            Glu Glu Leu Cys Val Arg Trp Thr Gln Leu Gly Ala Phe Tyr Pro Phe
            Met Arg Asn His Asn Ser Leu Leu Ser Leu Pro Gln Glu Pro Tyr Ser
            Phe Ser Glu Pro Ala Gln Gln Ala Met Arg Lys Ala Leu Thr Leu Arg
            Tyr Ala Leu Leu Pro His Leu Tyr Thr Leu Phe His Gln Ala His Val
            Ala Gly Glu Thr Val Ala Arg Pro Leu Phe Leu Glu Phe Pro Lys Asp
            Ser Ser Thr Trp Thr Val Asp His Gln Leu Leu Trp Gly Glu Ala Leu
            Leu Ile Thr Pro Val Leu Gln Ala Gly Lys Ala Glu Val Thr Gly Tyr
            Phe Pro Leu Gly Thr Trp Tyr Asp Leu Gln Thr Val Pro Ile Glu Ala
            Leu Gly Ser Leu Pro Pro Pro Ala Ala Pro Arg Glu Pro Ala Ile
            His Ser Glu Gly Gln Trp Val Thr Leu Pro Ala Pro Leu Asp Thr Ile
            Asn Val His Leu Arg Ala Gly Tyr Ile Ile Pro Leu Gln Gly Pro Gly
            Leu Thr Thr Thr Glu Ser Arg Gln Gln Pro Met Ala Leu Ala Val Ala
            Leu Thr Lys Gly Gly Glu Ala Arg Gly Glu Leu Phe Trp Asp Asp Gly
            Glu Ser Leu Glu Val Leu Glu Arg Gly Ala Tyr Thr Gln Val Ile Phe
            Leu Ala Arg Asn Asn Thr Ile Val Asn Glu Leu Val Arg Val Thr Ser
            Glu Gly Ala Gly Leu Gln Leu Gln Lys Val Thr Val Leu Gly Val Ala
            Thr Ala Pro Gln Gln Val Leu Ser Asn Gly Val Pro Val Ser Asn Phe
            Thr Tyr Ser Pro Asp Thr Lys Val Leu Asp Ile Cys Val Ser Leu Leu
            Met Gly Glu Gln Phe Leu Val Ser Trp Cys

SEQ ID NO: 2  Gln Gln Gly Ala Ser Arg Pro Gly Pro Arg Asp Ala Gln Ala His Pro
            Gly Arg Pro Arg Ala Val Pro Thr Gln Cys Asp Val Pro Pro Asn Ser
            Arg Phe Asp Cys Ala Pro Asp Lys Ala Ile Thr Gln Glu Gln Cys Glu
            Ala Arg Gly Cys Cys Tyr Ile Pro Ala Lys Gln Gly Leu Gln Gly Ala
            Gln Met Gly Gln Pro Trp Cys Phe Phe Pro Pro Ser Tyr Pro Ser Tyr
            Lys Leu Glu Asn Leu Ser Ser Ser Glu Met Gly Tyr Thr Ala Thr Leu
            Thr Arg Thr Thr Pro Thr Phe Phe Pro Lys Asp Ile Leu Thr Leu Arg
            Leu Asp Val Met Met Glu Thr Glu Asn Arg Leu His Phe Thr Ile Lys
            Asp Pro Ala Asn Arg Arg Tyr Glu Val Pro Leu Glu Thr Pro Arg Val
            His Ser Arg Ala Pro Ser Pro Leu Tyr Ser Val Glu Phe Ser Glu Glu
            Pro Phe Gly Val Ile Val His Arg Gln Leu Asp Gly Arg Val Leu Leu
            Asn Thr Thr Val Ala Pro Leu Phe Ala Asp Gln Phe Leu Gln Leu
            Ser Thr Ser Leu Pro Ser Gln Tyr Ile Thr Gly Leu Ala Glu His Leu
            Ser Pro Leu Met Leu Ser Thr Ser Trp Thr Arg Ile Thr Leu Trp Asn
            Arg Asp Leu Ala Pro Thr Pro Gly Ala Asn Leu Tyr Gly Ser His Pro
            Phe Tyr Leu Ala Leu Glu Asp Gly Gly Ser Ala His Gly Val Phe Leu
            Leu Asn Ser Asn Ala Met Asp Val Val Leu Gln Pro Ser Pro Ala Leu
            Ser Trp Arg Ser Thr Gly Gly Ile Leu Asp Val Tyr Ile Phe Leu Gly
            Pro Glu Pro Lys Ser Val Val Gln Gln Tyr Leu Asp Val Val Gly Tyr
            Pro Phe Met Pro Pro Tyr Trp Gly Leu Gly Phe His Leu Cys Arg Trp
            Gly Tyr Ser Ser Thr Ala Ile Thr Arg Gln Val Val Glu Asn Met Thr
            Arg Ala His Phe Pro Leu Asp Val Gln Trp Asn Asp Leu Asp Tyr
            Met Asp Ser Arg Arg Asp Phe Thr Phe Asn Lys Asp Gly Phe Arg
            Asp Phe Pro Ala Met Val Gln Glu Leu His Gln Gly Gly Arg Arg Tyr
            Met Met Ile Val Asp Pro Ala Ile Ser Ser Ser Gly Pro Ala Gly Ser Tyr
            Arg Pro Tyr Asp Glu Gly Leu Arg Arg Gly Val Phe Ile Thr Asn Glu
            Thr Gly Gln Pro Leu Ile Gly Lys Val Trp Pro Gly Ser Thr Ala Phe
            Pro Asp Phe Thr Asn Pro Thr Ala Leu Ala Trp Trp Glu Asp Met Val
            Ala Glu Phe His Asp Gln Val Pro Phe Asp Gly Met Trp Ile Asp Met
            Asn Glu Pro Ser Asn Phe Ile Arg Gly Ser Glu Asp Gly Cys Pro Asn
            Asn Glu Leu Glu Asn Pro Pro Tyr Val Pro Gly Val Val Gly Gly Thr
            Leu Gln Ala Ala Thr Ile Cys Ala Ser Ser His Gln Phe Leu Ser Thr
            His Tyr Asn Leu His Asn Leu Tyr Gly Leu Thr Glu Ala Ile Ala Ser
            His Arg Ala Leu Val Lys Ala Arg Gly Thr Arg Pro Phe Val Ile Ser
            Arg Ser Thr Phe Ala Gly His Gly Arg Tyr Ala Gly His Trp Thr Gly
            Asp Val Trp Ser Ser Trp Glu Gln Leu Ala Ser Ser Val Pro Glu Be
            Leu Gln Phe Asn Leu Leu Gly Val Pro Leu Val Gly Ala Asp Val Cys
            Gly Phe Leu Gly Asn Thr Ser Glu Glu Leu Cys Val Arg Trp Thr Gln
            Leu Gly Ala Phe Tyr Pro Phe Met Arg Asn His Asn Ser Leu Leu Ser
```

```
Leu Pro Gln Glu Pro Tyr Ser Phe Ser Glu Pro Ala Gln Gln Ala Met
Arg Lys Ala Leu Thr Leu Arg Tyr Ala Leu Leu Pro His Leu Tyr Thr
Leu Phe His Gln Ala His Val Ala Gly Glu Thr Val Ala Arg Pro Leu
Phe Leu Glu Phe Pro Lys Asp Ser Ser Thr Trp Thr Val Asp His Gln
Leu Leu Trp Gly Glu Ala Leu Leu Ile Thr Pro Val Leu Gln Ala Gly
Lys Ala Glu Val Thr Gly Tyr Phe Pro Leu Gly Thr Trp Tyr Asp Leu
Gln Thr Val Pro Ile Glu Ala Leu Gly Ser Leu Pro Pro Pro Pro Ala
Ala Pro Arg Glu Pro Ala Ile His Ser Glu Gly Gln Trp Val Thr Leu
Pro Ala Pro Leu Asp Thr Ile Asn Val His Leu Arg Ala Gly Tyr Ile Ile
Pro Leu Gln Gly Pro Gly Leu Thr Thr Thr Glu Ser Arg Gln Gln Pro
Met Ala Leu Ala Val Ala Leu Thr Lys Gly Gly Glu Ala Arg Gly Glu
Leu Phe Trp Asp Asp Gly Glu Ser Leu Glu Val Leu Glu Arg Gly Ala
Tyr Thr Gln Val Ile Phe Leu Ala Arg Asn Asn Thr Ile Val Asn Glu
Leu Val Arg Val Thr Ser Glu Gly Ala Gly Leu Gln Leu Gln Lys Val
Thr Val Leu Gly Val Ala Thr Ala Pro Gln Gln Val Leu Ser Asn Gly
Val Pro Val Ser Asn Phe Thr Tyr Ser Pro Asp Thr Lys Val Leu Asp
Ile Cys Val Ser Leu Leu Met Gly Glu Gln Phe Leu Val Ser Trp Cys
```

In at least one embodiment, the recombinant human acid α-glucosidase has a wild-type GAA amino acid sequence as set forth in SEQ ID NO: 1, as described in U.S. Pat. No. 8,592,362 and has GenBank accession number AHE24104.1 (GI:568760974). In at least one embodiment, the recombinant human acid α-glucosidase is glucosidase alfa, the human acid α-glucosidase enzyme encoded by the most predominant of nine observed haplotypes of the GAA gene.

In at least one embodiment, the recombinant human acid α-glucosidase is initially expressed as having the full-length 952 amino acid sequence of wild-type GAA as set forth in SEQ ID NO: 1, and the recombinant human acid α-glucosidase undergoes intracellular processing that removes a portion of the amino acids, e.g. the first 56 amino acids. Accordingly, the recombinant human acid α-glucosidase that is secreted by the host cell can have a shorter amino acid sequence than the recombinant human acid α-glucosidase that is initially expressed within the cell. In at least one embodiment, the shorter protein can have the amino acid sequence set forth in SEQ ID NO: 2, which only differs from SEQ ID NO: 1 in that the first 56 amino acids comprising the signal peptide and precursor peptide have been removed, thus resulting in a protein having 896 amino acids. Other variations in the number of amino acids is also possible, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. In some embodiments, the rhGAA product includes a mixture of recombinant human acid α-glucosidase molecules having different amino acid lengths.

In at least one embodiment, the recombinant human acid α-glucosidase undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments the enzyme is initially expressed as having an amino acid sequence as set forth in SEQ ID NO: 1 or SEQ ID NO: 2, and the enzyme undergoes one or more of these post-translational and/or chemical modifications. Such modifications are also within the scope of the present disclosure.

Polynucleotide sequences encoding GAA and such variant human GAAs are also contemplated and may be used to recombinantly express rhGAAs according to the invention.

Preferably, no more than 70, 65, 60, 55, 45, 40, 35, 30, 25, 20, 15, 10, or 5% of the total recombinant human lysosomal protein (e.g. rhGAA) molecules lack an N-glycan unit bearing one or more mannose-6-phosphate residues or lacks a capacity to bind to the cation independent mannose-6-phosphate receptor (CIMPR). Alternatively, 30, 35, 40, 45, 50, 55, 60, 65, 70, 75, 80, 85, 90, 95, 99%, <100% or more of the recombinant human lysosomal protein (e.g. rhGAA) molecules comprise at least one N-glycan unit bearing one or more mannose-6-phosphate residues or has the capacity to bind to CIMPR.

The recombinant human lysosomal protein (e.g. rhGAA) molecules may have 1, 2, 3 or 4 mannose-6-phosphate (M6P) groups on their glycans. For example, only one N-glycan on a recombinant human lysosomal protein molecule may bear M6P (mono-phosphorylated), a single N-glycan may bear two M6P groups (bis-phosphorylated), or two different N-glycans on the same recombinant human lysosomal protein molecule may each bear single M6P groups. Recombinant human lysosomal protein molecules may also have N-glycans bearing no M6P groups. In another embodiment, on average the N-glycans contain greater than 3 mol/mol of M6P and greater than 4 mol/mol sialic acid, such that the recombinant human lysosomal protein comprises on average at least 3 moles of mannose-6-phosphate residues per mole of recombinant human lysosomal protein and at least 4 moles of sialic acid per mole of recombinant human lysosomal protein. On average at least about 3, 4, 5, 6, 7, 8, 9, or 10% of the total glycans on the recombinant human lysosomal protein may be in the form of a mono-M6P glycan, for example, about 6.25% of the total glycans may carry a single M6P group and on average, at least about 0.5, 1, 1.5, 2.0, 2.5, 3.0% of the total glycans on recombinant human lysosomal protein are in the form of a bis-M6P glycan and on average less than 25% of total recombinant human lysosomal protein contains no phosphorylated glycan binding to CIMPR.

The recombinant human lysosomal protein (e.g. rhGAA) may have an average content of N-glycans carrying M6P ranging from 0.5 to 7.0 mol/mol lysosomal protein or any intermediate value of subrange including 0.5, 1.0, 1.5, 2.0, 2.5, 3.0, 3.5, 4.0, 4.5, 5.0, 5.5, 6.0, 6.5, or 7.0 mol/mol lysosomal protein. The lysosomal protein can be fractionated to provide lysosomal protein preparations with different average numbers of M6P-bearing or bis-M6P-bearing glycans thus permitting further customization of lysosomal protein targeting to the lysosomes in target tissues by selecting a particular fraction or by selectively combining different fractions.

In some embodiments, the recombinant human lysosomal protein (e.g. rhGAA) will bear, on average, 2.0 to 8.0 moles of M6P per mole of recombinant human lysosomal protein (e.g. rhGAA). This range includes all intermediate values and subranges including 2.0, 2.5, 3.0, 3.5, 4.0, 4.5, 5.0, 5.5, 6.0, 6.5, 7.0, 7.5 and 8.0 mol M6P/mol recombinant human lysosomal protein (e.g. rhGAA).

Up to 60% of the N-glycans on the recombinant human lysosomal protein (e.g. rhGAA) may be fully sialylated, for example, up to 10%, 20%, 30%, 40%, 50% or 60% of the N-glycans may be fully sialylated. In some embodiments from 4 to 20% of the total N-glycans are fully sialylated. In other embodiments no more than 5%, 10%, 20% or 30% of N-glycans on the recombinant human lysosomal protein (e.g. rhGAA) carry sialic acid and a terminal galactose residue (Gal). This range includes all intermediate values and subranges, for example, 7 to 30% of the total N-glycans on the recombinant human lysosomal protein can carry sialic acid and terminal galactose. In yet other embodiments, no more than 5, 10, 15, 16, 17, 18, 19 or 20% of the N-glycans on recombinant human lysosomal protein have a terminal galactose only and do not contain sialic acid. This range includes all intermediate values and subranges, for example, from 8 to 19% of the total N-glycans on the recombinant human lysosomal protein in the composition may have terminal galactose only and do not contain sialic acid.

In other embodiments of the invention, 40, 45, 50, 55 to 60% of the total N-glycans on the recombinant human lysosomal protein (e.g. rhGAA) are complex type N-glycans; or no more than 1, 2, 3, 4, 5, 6, 7% of total N-glycans on the recombinant human lysosomal protein (e.g. rhGAA) are hybrid-type N-glycans; no more than 5, 10, or 15% of the high mannose-type N-glycans on the recombinant human lysosomal protein (e.g. rhGAA) are non-phosphorylated; at least 5% or 10% of the high mannose-type N-glycans on the recombinant human lysosomal protein (e.g. rhGAA) are mono-M6P phosphorylated; and/or at least 1 or 2% of the high mannose-type N-glycans on the recombinant human lysosomal protein (e.g. rhGAA) are bis-M6P phosphorylated. These values include all intermediate values and subranges. A recombinant human lysosomal protein (e.g. rhGAA) may meet one or more of the content ranges described above.

In some embodiments, the recombinant human lysosomal protein (e.g. rhGAA) will bear, on average, 2.0 to 8.0 moles of sialic acid residues per mole of recombinant human lysosomal protein (e.g. rhGAA). This range includes all intermediate values and subranges including 2.0, 2.5, 3.0, 3.5, 4.0, 4.5, 5.0, 5.5, 6.0, 6.5, 7.0, 7.5 and 8.0 mol residues/mol recombinant human lysosomal protein (e.g. rhGAA). Without being bound by theory, it is believed that the presence of N-glycan units bearing sialic acid residues may prevent non-productive clearance of the recombinant human lysosomal protein (e.g. rhGAA) by asialoglycoprotein receptors.

In one or more embodiments, the recombinant human lysosomal protein (e.g. rhGAA) has M6P and/or sialic acid units at certain N-glycosylation sites of the recombinant human lysosomal protein. For example, as stated above, there are seven potential N-linked glycosylation sites on rhGAA. These potential glycosylation sites are at the following positions of SEQ ID NO: 2: N84, N177, N334, N414, N596, N826 and N869. Similarly, for the full-length amino acid sequence of SEQ ID NO: 1, these potential glycosylation sites are at the following positions: N140, N233, N390, N470, N652, N882 and N925. Other variants of rhGAA can have similar glycosylation sites, depending on the location of asparagine residues. Generally, sequences of ASN-X-SER or ASN-X-THR in the protein amino acid sequence indicate potential glycosylation sites, with the exception that X cannot be HIS or PRO.

In various embodiments, the rhGAA has a certain N-glycosylation profile. In one or more embodiments, at least 20% of the rhGAA is phosphorylated at the first N-glycosylation site (e.g. N84 for SEQ ID NO: 2 and N140 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the first N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the first N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the first N-glycosylation site.

In one or more embodiments, at least 20% of the rhGAA is phosphorylated at the second N-glycosylation site (e.g. N177 for SEQ ID NO: 2 and N223 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the second N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the second N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the second N-glycosylation site. In one or more embodiments, at least 5% of the rhGAA is phosphorylated at the third N-glycosylation site (e.g. N334 for SEQ ID NO: 2 and N390 for SEQ ID NO: 1). In other embodiments, less than 5%, 10%, 15%, 20% or 25% of the rhGAA is phosphorylated at the third N-glycosylation site. For example, the third N-glycosylation site can have a mixture of non-phosphorylated high mannose glycans, di-, tri-, and tetra-antennary complex glycans, and hybrid glycans as the major species. In some embodiments, at least 3%, 5%, 8%, 10%, 15%, 20%, 25%, 30%, 35%, 40%, 45% or 50% of the rhGAA is sialylated at the third N-glycosylation site.

In one or more embodiments, at least 20% of the rhGAA is phosphorylated at the fourth N-glycosylation site (e.g. N414 for SEQ ID NO: 2 and N470 for SEQ ID NO: 1). For example, at least 20%, 25%, 30%, 35%, 40%, 45%, 50%, 55%, 60%, 65%, 70%, 75%, 80%, 85%, 90% or 95% of the rhGAA can be phosphorylated at the fourth N-glycosylation site. This phosphorylation can be the result of mono-M6P and/or bis-M6P units. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a mono-M6P unit at the fourth N-glycosylation site. In some embodiments, at least 10%, 15%, 20%, 25%, 30%, 35%, 40%, 45%, 50%, 55%, 60%, 65%, 70%, 75%, 80%, 85%, 90% or 95% of the rhGAA bears a bis-M6P unit at the fourth N-glycosylation site. In some embodiments, at least 3%, 5%, 8%, 10%, 15%, 20% or 25% of the rhGAA is sialylated at the fourth N-glycosylation site.

In one or more embodiments, at least 5% of the rhGAA is phosphorylated at the fifth N-glycosylation site (e.g. N596 for SEQ ID NO: 2 and N692 for SEQ ID NO: 1). In other embodiments, less than 5%, 10%, 15%, 20% or 25% of the rhGAA is phosphorylated at the fifth N-glycosylation site. For example, the fifth N-glycosylation site can have fucosylated di-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the fifth N-glycosylation site.

In one or more embodiments, at least 5% of the rhGAA is phosphorylated at the sixth N-glycosylation site (e.g. N826 for SEQ ID NO: 2 and N882 for SEQ ID NO: 1). In other embodiments, less than 5%, 10%, 15%, 20% or 25% of the rhGAA is phosphorylated at the sixth N-glycosylation site. For example, the sixth N-glycosylation site can have a mixture of di-, tri-, and tetra-antennary complex glycans as the major species. In some embodiments, at least 3%, 5%, 8%, 10%, 15%, 20%, 25%, 30%, 35%, 40%, 45%, 50%, 55%, 60%, 65%, 70%, 75%, 80%, 85%, 90% or 95% of the rhGAA is sialylated at the sixth N-glycosylation site.

In one or more embodiments, at least 5% of the rhGAA is phosphorylated at the seventh N-glycosylation site (e.g. N869 for SEQ ID NO: 2 and N925 for SEQ ID NO: 1). In other embodiments, less than 5%, 10%, 15%, 20% or 25% of the rhGAA is phosphorylated at the seventh N-glycosylation site. In some embodiments, less than 40%, 45%, 50%, 55%, 60% or 65% % of the rhGAA has any glycan at the seventh N-glycosylation site. In some embodiments, at least 30%, 35% or 40% of the rhGAA has a glycan at the seventh N-glycosylation site.

In various embodiments, the rhGAA has an average fucose content of 0-5 mol per mol of rhGAA, GlcNAc content of 10-30 mol per mol of rhGAA, galactose content of 5-20 mol per mol of rhGAA, mannose content of 10-40 mol per mol of rhGAA, M6P content of 2-8 mol per mol of rhGAA and sialic acid content of 2-8 mol per mol of rhGAA. In various embodiments, the rhGAA has an average fucose content of 2-3 mol per mol of rhGAA, GlcNAc content of 20-25 mol per mol of rhGAA, galactose content of 8-12 mol per mol of rhGAA, mannose content of 22-27 mol per mol of rhGAA, M6P content of 3-5 mol per mol of rhGAA and sialic acid content of 4-7 mol of rhGAA.

The recombinant human lysosomal protein (e.g. rhGAA) is preferably produced by Chinese hamster ovary (CHO) cells, such as CHO cell line GA-ATB-200 or ATB-200-001-X5-14, or by a subculture or derivative of such a CHO cell culture. DNA constructs, which express allelic variants of acid α-glucosidase or other variant acid α-glucosidase amino acid sequences such as those that are at least 90%, 95%, 98% or 99% identical to SEQ ID NO: 1 or SEQ ID NO: 2, may be constructed and expressed in CHO cells. These variant acid α-glucosidase amino acid sequences may contain deletions, substitutions and/or insertions relative to SEQ ID NO: 1 or SEQ ID NO: 2, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. Those of skill in the art can select alternative vectors suitable for transforming CHO cells for production of such DNA constructs.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The inventors have found that recombinant human acid α-glucosidase having superior ability to target cation-independent mannose-6-phosphate receptors (CIMPR) and cellular lysosomes as well as glycosylation patterns that reduce its non-productive clearance in vivo can be produced using Chinese hamster ovary (CHO) cells. These cells can be induced to express recombinant human acid α-glucosidase with significantly higher levels of N-glycan units bearing one or more mannose-6-phosphate residues than conventional recombinant human acid α-glucosidase products such as alglucosidase alfa. The recombinant human acid α-glucosidase produced by these cells, for example, as exemplified by ATB200, has significantly more muscle cell-targeting mannose-6-phosphate (M6P) and bis-mannose-6-phosphate N-glycan residues than conventional acid α-glucosidase, such as Lumizyme®. Without being bound by theory, it is believed that this extensive glycosylation allows the ATB200 enzyme to be taken up more effectively into target cells, and therefore to be cleared from the circulation more efficiently than other recombinant human acid α-glucosidases, such as for example, alglucosidase alfa, which has a much lower M6P and bis-M6P content. ATB200 has been shown to efficiently bind to CIMPR and be efficiently taken up by skeletal muscle and cardiac muscle and to have a glycosylation pattern that provides a favorable pharmacokinetic profile and reduces non-productive clearance in vivo.

It is also contemplated that the extensive glycosylation of ATB200 can contribute to a reduction of the immunogenicity of ATB200 compared to, for example, alglucosidase alfa. As will be appreciated by those skilled in the art, glycosylation of proteins with conserved mammalian sugars generally enhances product solubility and diminishes product aggregation and immunogenicity. Glycosylation indirectly alters protein immunogenicity by minimizing protein aggregation as well as by shielding immunogenic protein epitopes from the immune system (Guidance for Industry—Immunogenicity Assessment for Therapeutic Protein Products, US Department of Health and Human Services, Food and Drug Administration, Center for Drug Evaluation and Research, Center for Biologics Evaluation and Research, August 2014). Therefore, in at least one embodiment, administration of the recombinant human acid α-glucosidase does not induce anti-drug antibodies. In at least one embodiment, administration of the recombinant human acid α-glucosidase induces a lower incidence of anti-drug antibodies in a subject than the level of anti-drug antibodies induced by administration of alglucosidase alfa.

As described in co-pending international patent application PCT/US2015/053252, cells such as CHO cells can be used to produce the rhGAA described therein, and this rhGAA can be used in the present invention. Examples of such a CHO cell line are GA-ATB-200 or ATB-200-001-X5-14, or a subculture thereof that produces a rhGAA composition as described therein. Such CHO cell lines may contain multiple copies of a gene, such as 5, 10, 15, or 20 or more copies, of a polynucleotide encoding GAA.

The high M6P and bis-M6P rhGAA, such as ATB200 rhGAA, can be produced by transforming CHO cells with a DNA construct that encodes GAA. While CHO cells have been previously used to make rhGAA, it was not appreciated that transformed CHO cells could be cultured and selected in a way that would produce rhGAA having a high content of M6P and bis-M6P glycans which target the CIMPR.

Surprisingly, it was found that it was possible to transform CHO cell lines, select transformants that produce rhGAA containing a high content of glycans bearing M6P or bis-M6P that target the CIMPR, and to stably express this high-M6P rhGAA. Thus, methods for making these CHO cell lines are also described in co-pending international patent application PCT/US2015/053252. This method involves transforming a CHO cell with DNA encoding GAA or a GAA variant, selecting a CHO cell that stably integrates the DNA encoding GAA into its chromosome(s) and that stably expresses GAA, and selecting a CHO cell that expresses GAA having a high content of glycans bearing M6P or bis-M6P, and, optionally, selecting a CHO cell having N-glycans with high sialic acid content and/or having N-glycans with a low non-phosphorylated high-mannose content.

These CHO cell lines may be used to produce rhGAA and rhGAA compositions by culturing the CHO cell line and recovering said composition from the culture of CHO cells.

Production, Capturing and Purification of Recombinant Human Lysosomal Protein

Various embodiments of the present invention pertain to methods for the production and/or capturing and/or purification of recombinant human lysosomal protein (e.g. rhGAA). An exemplary process 600 for producing, capturing and purifying recombinant human lysosomal protein is shown in FIG. 6.

Figure 6:
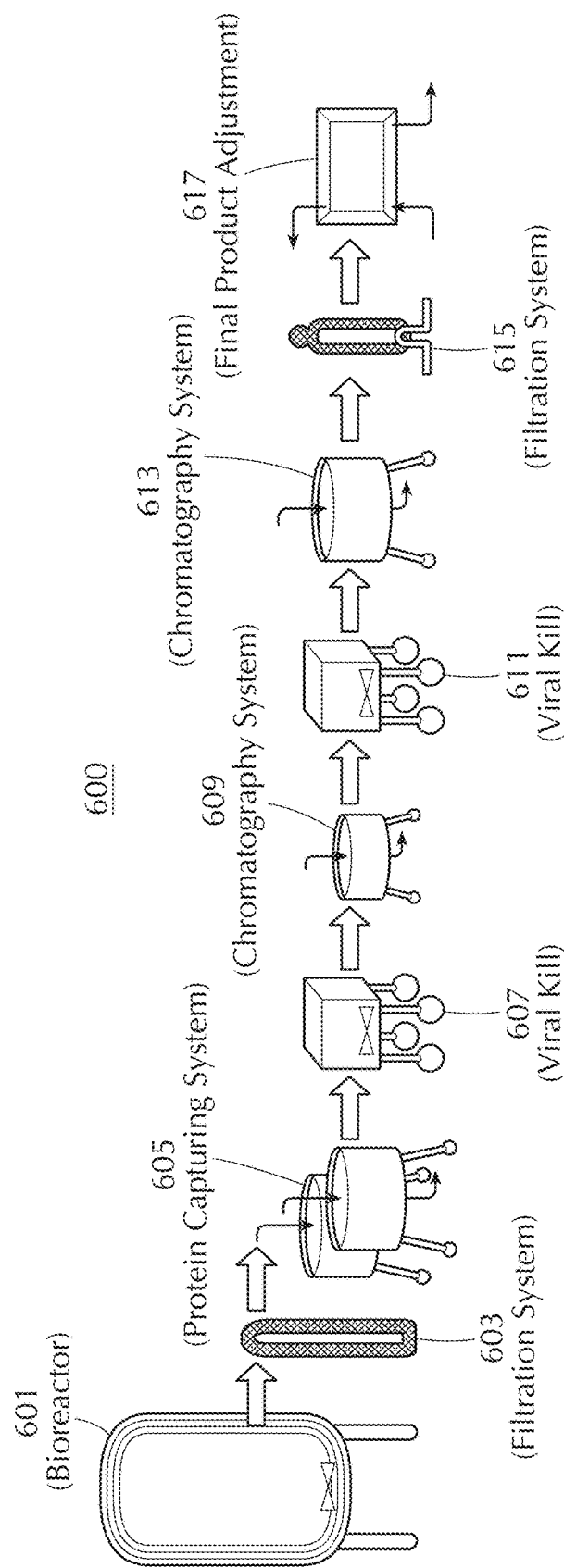
FIG. 6 is a schematic diagram of an exemplary process for the manufacturing, capturing and purification of a recombinant lysosomal protein.
Figure 7A:
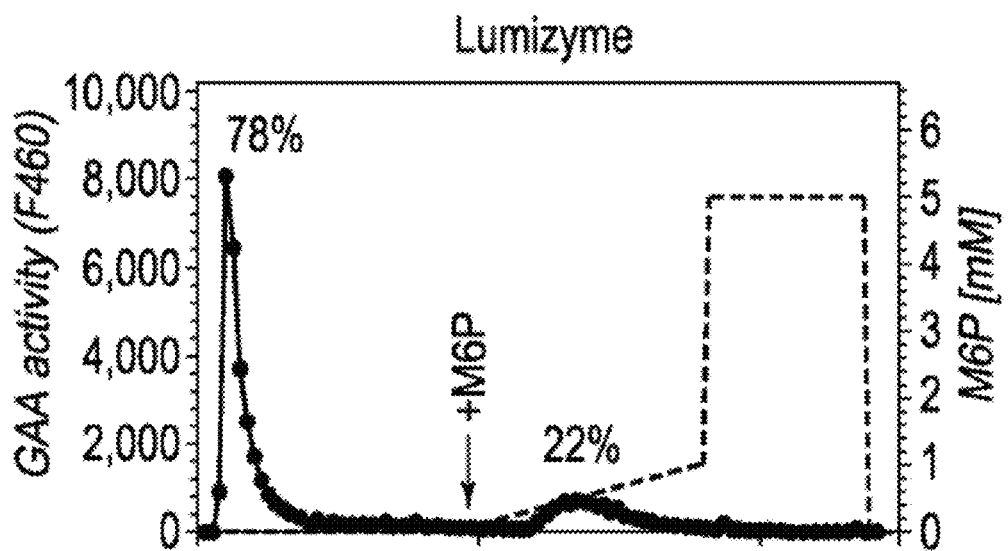
FIGS. 7A and 7B, respectively, are graphs showing the results of CIMPR affinity chromatography of Myozyme® and ATB200 rhGAA. As apparent from FIG. 7B, about 70% of the rhGAA in ATB200 rhGAA contained M6P.
Figure 7B:
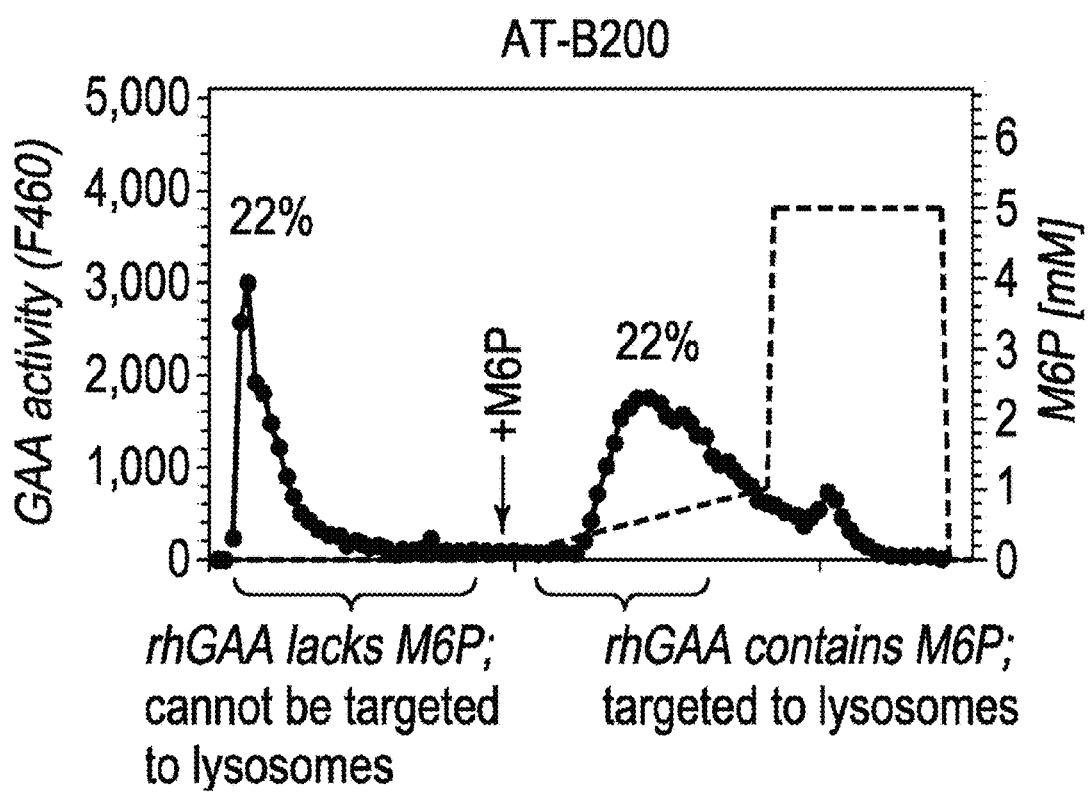

In FIG. 6, the arrows indicate the direction of movement for the various liquid phases containing the recombinant human lysosomal protein. Bioreactor 601 contains a culture of cells, such as CHO cells, that express and secrete recombinant human lysosomal protein (e.g. rhGAA) into the surrounding liquid culture media. The bioreactor 601 can be any appropriate bioreactor for culturing the cells, such as a perfusion, batch or fed-batch bioreactor. In various embodiments, the bioreactor has a volume between about 1 L and about 20,000 L. Exemplary bioreactor volumes include about 1 L, about 10 L, about 20 L, about 30 L, about 40 L, about 50 L, about 60 L, about 70 L, about 80 L, about 90 L, about 100 L, about 150 L, about 200 L, about 250 L, about 300 L, about 350 L, about 400 L, about 500 L, about 600 L, about 700 L, about 800 L, about 900 L, about 1,000 L, about 1,500 L, about 2,000 L, about 2,500 L, about 3,000 L, about 3,500 L, about 4,000 L, about 5,000 L, about 6,000 L, about 7,000 L, about 8,000 L, about 9,000 L, about 10,000 L, about 15,000 L and about 20,000 L.

As shown in FIG. 6, the media can be removed from the bioreactor. Such media removal can be continuous for a perfusion bioreactor or can be batchwise for a batch or fed-batch reactor. The media is filtered by filtration system 603 to remove cells. In some embodiments, the cells removed from the media are re-introduced to the bioreactor and the media comprising the secrete recombinant human lysosomal protein can be further processed. Filtration system 603 can be any suitable filtration system, including an alternating tangential flow filtration (ATF) system, a tangential flow filtration (TFF) system, centrifugal filtration system, etc. In various embodiments, the filtration system utilizes a filter having a pore size between about 10 nanometers and about 2 micrometers. Exemplary filter pore sizes include about 10 nm, about 20 nm, about 30 nm, about 40 nm, about 50 nm, about 60 nm, about 70 nm, about 80 nm, about 90 nm, about 100 nm, about 150 nm, about 200 nm, about 250 nm, about 300 nm, about 350 nm, about 400 nm, about 500 nm, about 600 nm, about 700 nm, about 800 nm, about 900 nm, about 1 μm, about 1.5 μm and about 2 μm.

In various embodiments, the media removal rate is between about 1 L/day and about 20,000 L/day. Exemplary media removal rates include about 1 L/day, about 10 L/day, about 20 L/day, about 30 L/day, about 40 L/day, about 50 L/day, about 60 L/day, about 70 L/day, about 80 L/day, about 90 L/day, about 100 L/day, about 150 L/day, about 200 L/day, about 250 L/day, about 300 L/day, about 350 L/day, about 400 L/day, about 500 L/day, about 600 L/day, about 700 L/day, about 800 L/day, about 900 L/day, about 1,000 L/day, about 1,500 L/day, about 2,000 L/day, about 2,500 L/day, about 3,000 L/day, about 3,500 L/day, about 4,000 L/day, about 5,000 L/day, about 6,000 L/day, about 7,000 L/day, about 8,000 L/day, about 9,000 L/day, about 10,000 L/day, about 15,000 L/day and about 20,000 L/day. Alternatively, the media removal rate can be expressed as a function of the bioreactor volume, such as about 0.1 to about 3 reactor volumes per day. Exemplary media removal rates include about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 2, about 2.5 and about 3 reactor volumes per day.

For a continuous or fed-batch process, the rate at which fresh media is provided to the bioreactor can be between about 1 L/day and about 20,000 L/day. Exemplary media introduction rates include about 1 L/day, about 10 L/day, about 20 L/day, about 30 L/day, about 40 L/day, about 50 L/day, about 60 L/day, about 70 L/day, about 80 L/day, about 90 L/day, about 100 L/day, about 150 L/day, about 200 L/day, about 250 L/day, about 300 L/day, about 350 L/day, about 400 L/day, about 500 L/day, about 600 L/day, about 700 L/day, about 800 L/day, about 900 L/day, about 1,000 L/day, about 1,500 L/day, about 2,000 L/day, about 2,500 L/day, about 3,000 L/day, about 3,500 L/day, about 4,000 L/day, about 5,000 L/day, about 6,000 L/day, about 7,000 L/day, about 8,000 L/day, about 9,000 L/day, about 10,000 L/day, about 15,000 L/day and about 20,000 L/day. Alternatively, the media introduction rate can be expressed as a function of the bioreactor volume, such as about 0.1 to about 3 reactor volumes per day. Exemplary media introduction rates include about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 2, about 2.5 and about 3 reactor volumes per day.

After filtration, the filtrate is loaded onto a protein capturing system 605. The protein capturing system 605 can include one or more chromatography columns. If more than one chromatography column is used, then the columns may be placed in series so that the next column can begin loading once the first column is loaded. Alternatively, the media removal process can be stopped during the time that the columns are switched.

In various embodiments, the protein capturing system 605 includes one or more anion exchange (AEX) columns for the direct product capture of recombinant human lysosomal protein, particularly lysosomal protein having a high M6P content. While not wishing to be bound by any particular theory, it is believed that using AEX chromatography to capture the recombinant human lysosomal protein from the filtered media ensures that the captured recombinant protein product has a higher M6P content, due to the more negative charge of the recombinant protein having one or more M6P groups. As a result, non-phosphorylated recombinant protein and host cell impurities do not bind the column resin as well as the highly phosphorylated recombinant protein, and the non-phosphorylated recombinant protein and host cell impurities passes through the column. Accordingly, the AEX chromatography can be used to enrich the M6P content of the protein product (i.e. select for proteins having more M6P) due to the high affinity of the M6P-containing proteins for the AEX resin.

Furthermore, while not wishing to be bound by any particular theory, it is also believed that having a direct product capture of recombinant protein using AEX chromatography ensures that the recombinant proteins having high M6P content are removed from the media containing proteases and other enzymes that can degrade the protein and/or dephosphorylate the protein. As a result, the high quality product is preserved.

Suitable AEX chromatography columns have functional chemical groups that bind negatively charged proteins. Exemplary functional groups include, but are not limited to, primary, secondary, tertiary, and quaternary ammonium or amine groups. These functional groups may be bound to membranes (e.g. cellulose membranes) or conventional chromatography resins. Exemplary column media include SP, CM, Q and DEAE Sepharose® Fast Flow media from GE Healthcare Lifesciences.

The volume of the AEX chromatography column can be any suitable volume, such as between 1 L and 1,000 L. Exemplary column volumes include about 1 L, about 2 L, about 3 L, about 4 L, about 5 L, about 6 L, about 7 L, about 8 L, about 9 L, about 10 L, about 20 L, about 30 L, about 40 L, about 50 L, about 60 L, about 70 L, about 80 L, about 90 L, about 100 L, about 150 L, about 200 L, about 250 L, about 300 L, about 350 L, about 400 L and about 500 L, about 600 L, about 700 L, about 800 L, about 900 L and about 1,000 L.

Exemplary conditions for an anion-exchange column are provided in Table 2 below:

TABLE 2

| Procedure | Buffer | Flow rate (cm/h) | Volume (CV) | Temperature (° C.) |
|---|---|---|---|---|
| Pre-used Sanitization | 0.1-10M NaOH | ≤25-2500 | ≥1-3 (≥10-120 min) | 15-25 |
| Pre-Equilibration | 20-2000 mM phosphate buffer (PB), pH 6.9-7.3 | ≤25-2500 | ≥1-5 | 15-25 |
| Equilibration | 4-400 mM PB, pH 6.9-7.3 | ≤25-2500 | ≥1-5 | 2-15 |
| Load | NA | ≤10-1000 | NA | 2-15 |
| Wash1 | 4-400 mM PB, pH 6.9-7.3 | ≤25-2500 | ≥2-10 | 2-15 |
| Wash2 | 4-400 mM PB, pH 6.9-7.3 | ≤25-2500 | ≥2-10 | 15-25 |
| Elution | 4-400 mM PB, 20-2000 mM NaCl, pH 6.1-6.5 | ≤25-2500 | NA | 15-25 |
| Strip | 4-400 mM PB, 0.1-10M NaCl, pH 6.1-6.5 | ≤25-2500 | ≥1-5 | 15-25 |
| Post-use Sanitization | 0.1-10M NaOH | ≤25-2500 | ≥1-3 (≥10-120 min) | 15-25 |
| Storage | 0.01-1.0M NaOH | ≤25-2500 | ≥1-5 | 15-25 |

After the recombinant human lysosomal protein is loaded onto the protein capturing system 605, the recombinant human lysosomal protein is eluted from the column(s) by changing the pH and/or salt content in the column.

The eluted recombinant human lysosomal protein can be subjected to further purification steps and/or quality assurance steps. For example, as shown in FIG. 6, the eluted recombinant human lysosomal protein can be subjected to a virus kill step 607. Such a virus kill 607 can include one or more of a low pH kill, a detergent kill, or other technique known in the art.

The recombinant protein product from the virus kill step 607 can be introduced into a second chromatography system 609 to further purify the recombinant protein product. Alternatively, the eluted recombinant protein from the protein capturing system 605 can be fed directly to the second chromatography system 609. In various embodiments, the second chromatography system 609 includes one or more immobilized metal affinity chromatography (IMAC) columns for further removal of impurities. Exemplary metal ions include cobalt, nickel, copper, iron, zinc or gallium.

The volume of the second chromatography column (e.g. IMAC column) can be any suitable volume, such as between 0.1 L and 100 L. Exemplary column volumes include about 0.1 L, about 0.2 L, about 0.3 L, about 0.4 L, about 0.5 L, about 0.6 L, about 0.7 L, about 0.8 L, about 0.9 L, about 1 L, about 1.5 L, about 2 L, about 2.5 L, about 3 L, about 3.5 L, about 4 L, about 4.5 L, about 5 L, about 6 L, about 7 L, about 8 L, about 9 L, about 10 L, about 15 L, about 20 L, about 25 L, about 30 L, about 35 L, about 40 L and about 50 L, about 60 L, about 70 L, about 80 L, about 90 L and about 100 L.

Exemplary conditions for an IMAC column are provided in Table 3 below:

TABLE 3

| Procedure | Buffer | Flow rate (cm/h) | Vol (CV) |
|---|---|---|---|
| Rinse | 4-400 mM PB, pH 6.3-6.7 | ≤25-2500 | ≥1-5 |
| Pre-use Sanitization | 0.01-1.0M NaOH | ≤25-2500 | ≥1-3 (10-30 min) |
| Equilibration | 4-400 mM PB, pH 6.5 | ≤25-2500 | ≥1-5 |
| Wash with WFI | Water For Injection (WFI) | ≤25-2500 | ≥1-3 |
| Chelating | 0.01-1.0M Copper Acetate | ≤25-2500 | ≥1-5 |
| Wash with WFI | WFI | ≤25-2500 | ≥2-10 |
| Wash with acidic buffer | 2-200 mM Sodium Acetate, 0.05-5M NaCl, pH 3.5-4.5 | ≤25-2500 | ≥2-10 |
| Equilibration | 4-400 mM PB, pH 6.3-6.7 | ≤25-2500 | ≥1-5 |
| Blank run with | 4-400 mM PB, 15-1500 mM | ≤25-2500 | ≥2-20 |

TABLE 3-continued

| Procedure | Buffer | Flow rate (cm/h) | Vol (CV) |
|---|---|---|---|
| elution buffer | Glycine, pH 6.1-6.5 | | |
| Equilibration | 4-400 mM PB, pH 6.3-6.7 | ≤25-2500 | ≥1-5 |
| Load | NA | ≤25-2500 | ≥1-5 |
| Wash1 | 4-400 mM PB, pH 6.3-6.7 | ≤25-2500 | ≥2-10 |
| Wash2 | 4-400 mM PB, 0.1-10M NaCl, 5-30% propylene glycol, pH 6.3-6.7 | ≤25-2500 | ≥2-10 |
| Wash3 | 4-400 mM PB, pH 6.3-6.7 | ≤25-2500 | ≥2-10 |
| Elution | 4-400 mM PB, 15-1500 mM Glycine, pH 6.1-6.5 | ≤25-2500 | NA |
| Strip | 4-400 mM PB, 50-5000 mM imidazole, pH 6.3-6.7 | ≤25-2500 | ≥1-5 |
| Post-use Sanitization | 0.01-1M NaOH | ≤25-2500 | ≥1-3 (10-30 min) |
| Rinse | 4-400 mM PB, pH 6.3-6.7 | ≤25-2500 | ≥1-5 |
| Storage | 5-30% ethanol | ≤25-2500 | ≥1-5 |

After the recombinant protein is loaded onto the second chromatography system 609, the recombinant protein is eluted from the column(s). As shown in FIG. 6, the eluted recombinant protein can be subjected to a virus kill step 611. As with virus kill 607, virus kill 611 can include one or more of a low pH kill, a detergent kill, or other technique known in the art. In some embodiments, only one of virus kill 607 or 611 is used, or the virus kills are performed at the same stage in the purification process.

As shown in FIG. 6, the recombinant protein product from the virus kill step 611 can be introduced into a third chromatography system 613 to further purify the recombinant protein product. Alternatively, the eluted recombinant protein from the second chromatography system 609 can be fed directly to the third chromatography system 613. In various embodiments, the third chromatography system 613 includes one or more cation exchange chromatography (CEX) columns and/or size exclusion chromatography (SEC) columns for further removal of impurities. The recombinant protein product is then eluted from the third chromatography system 613.

The volume of the third chromatography column (e.g. CEX or SEC column) can be any suitable volume, such as between 0.1 L and 200 L. Exemplary column volumes include about 0.1 L, about 0.2 L, about 0.3 L, about 0.4 L, about 0.5 L, about 0.6 L, about 0.7 L, about 0.8 L, about 0.9 L, about 1 L, about 1.5 L, about 2 L, about 2.5 L, about 3 L, about 3.5 L, about 4 L, about 4.5 L, about 5 L, about 6 L, about 7 L, about 8 L, about 9 L, about 10 L, about 15 L, about 20 L, about 25 L, about 30 L, about 35 L, about 40 L and about 50 L, about 60 L, about 70 L, about 80 L, about 90 L, about 100 L, about 150 L and about 200 L.

Exemplary conditions for a CEX column are provided in Table 4 below:

TABLE 4

| Procedure | Buffer | Flow rate (cm/h) | Vol (CV) |
|---|---|---|---|
| Pre-used Sanitization | 0.1-10M NaOH | ≤25-2500 | ≥1-3 (≥10-120 min) |
| Equilibration | 2-200 mM Sodium citrate, pH 4.0-5.0 | ≤30-3000 | ≥2-10 |
| Load | NA | ≤30-3000 | NA |
| Wash | 2-200 mM Sodium citrate, pH 4.0-5.0 | ≤30-3000 | ≥2-10 |
| Elution | 2-200 mM Sodium citrate, 15-1500 mM NaCl, pH 4.0-5.0 | ≤30-3000 | ≥2-10 |
| Strip | 2-200 mM Sodium citrate, 0.1-10M NaCl, pH 4.0-5.0 | ≤30-3000 | ≥1-5 |
| Post-use Sanitization | 0.1-10M NaOH | ≤25-2500 | ≥1-3 (≥10-120 min) |
| Storage | 0.01-1.0M NaOH | ≤30-3000 | ≥1-5 |

The recombinant protein product may also be subjected to further processing. For example, another filtration system 615 may be used to remove viruses. In some embodiments, such filtration can utilize filters with pore sizes between 5 and 50 μm. Other product processing can include a product adjustment step 617, in which the recombinant protein product may be sterilized, filtered, concentrated, stored and/or have additional components for added for the final product formulation. For example, the recombinant protein product can be concentrated by a factor of 2-10 times, such as from an initial protein concentration of about 2 to about 20 mg/ml to a final protein concentration of about 4 to about 200 mg/ml. This final product can be used to fill vials and may be lyophilized for future use.

Administration of Recombinant Protein

The recombinant human lysosomal protein (e.g. rhGAA), or a pharmaceutically acceptable salt thereof, can be formulated in accordance with the routine procedures as a pharmaceutical composition adapted for administration to human beings. For example, in a preferred embodiment, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Recombinant human lysosomal protein (e.g. rhGAA) (or a composition or medicament containing recombinant human lysosomal protein) is administered by an appropriate route. In one embodiment, the recombinant human lysosomal protein is administered intravenously. In other embodiments, recombinant human lysosomal protein (e.g. rhGAA) is administered by direct administration to a target tissue, such as to heart or skeletal muscle (e.g. intramuscular), or nervous system (e.g. direct injection into the brain; intraventricularly; intrathecally). More than one route can be used concurrently, if desired.

The recombinant human lysosomal protein (e.g. rhGAA) (or a composition or medicament containing recombinant human lysosomal protein) is administered in a therapeutically effective amount (e.g. a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In at least one embodiment, the recombinant human acid α-glucosidase is administered by intravenous infusion at a dose of about about 1 mg/kg to about 100 mg/kg, such as about 5 mg/kg to about 30 mg/kg, typically about 5 mg/kg to about 20 mg/kg. In at least one embodiment, the recombinant human acid α-glucosidase is administered by intravenous infusion at a dose of about 5 mg/kg, about 10 mg/kg, about 15 mg/kg, about 20 mg/kg, about 25 mg/kg, about 30 mg/kg, about 35 mg/kg, about 40 mg/kg, about 50 mg/kg, about 50 mg/kg, about 60 mg/kg, about 70 mg/kg, about 80 mg/kg, about 90 mg/kg or about 100 mg/kg. In at least one embodiment, the recombinant human acid α-glucosidase is administered by intravenous infusion at a dose of about 20 mg/kg. The effective dose for a particular individual can be varied (e.g. increased or decreased) over time, depending on the needs of the individual. For example, in times of physical illness or stress, or if anti-acid α-glucosidase antibodies become present or increase, or if disease symptoms worsen, the amount can be increased.

The therapeutically effective amount of recombinant human acid α-glucosidase (or composition or medicament containing recombinant human acid α-glucosidase) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, recombinant human acid α-glucosidase is administered monthly, bimonthly; weekly; twice weekly; or daily. The administration interval for a single individual need not be a fixed interval, but can be varied over time, depending on the needs of the individual. For example, in times of physical illness or stress, if anti-recombinant human acid α-glucosidase antibodies become present or increase, or if disease symptoms worsen, the interval between doses can be decreased. In some embodiments, a therapeutically effective amount of 5, 10, 20, 50, 100, or 200 mg enzyme/kg body weight is administered twice a week, weekly or every other week with or without a chaperone.

The recombinant human lysosomal protein (e.g. rhGAA) may be prepared for later use, such as in a unit dose vial or syringe, or in a bottle or bag for intravenous administration. Kits containing the recombinant human lysosomal protein (e.g. rhGAA), as well as optional excipients or other active ingredients, such as chaperones or other drugs, may be enclosed in packaging material and accompanied by instructions for reconstitution, dilution or dosing for treating a subject in need of treatment, such as a patient having Pompe disease.

Combination Therapy of rhGAA and Pharmacological Chaperone

In various embodiments, the rhGAA (e.g. ATB200) produced by the processes described herein can be used in combination therapy with a pharmacological chaperone such as miglustat or duvoglustat.

In at least one embodiment, the pharmacological chaperone (e.g. miglustat) is administered orally. In at least one embodiment, the miglustat is administered at an oral dose of about 200 mg to about 400 mg, or at an oral dose of about 200 mg, about 250 mg, about 300 mg, about 350 mg or about 400 mg. In at least one embodiment, the miglustat is administered at an oral dose of about 233 mg to about 400 mg. In at least one embodiment, the miglustat is administered at an oral dose of about 250 to about 270 mg, or at an oral dose of about 250 mg, about 255 mg, about 260 mg, about 265 mg or about 270 mg. In at least one embodiment, the miglustat is administered as an oral dose of about 260 mg.

It will be understood by those skilled in the art that an oral dose of miglustat in the range of about 200 mg to 400 mg or any smaller range there within can be suitable for an adult patient with an average body weight of about 70 kg. For patients having a significantly lower body weight than about 70 kg, including but not limited to infants, children or underweight adults, a smaller dose may be considered suitable by a physician. Therefore, in at least one embodiment, the miglustat is administered as an oral dose of from about 50 mg to about 200 mg, or as an oral dose of about 50 mg, about 75 mg, about 100 mg, 125 mg, about 150 mg, about 175 mg or about 200 mg. In at least one embodiment, the miglustat is administered as an oral dose of from about 65 mg to about 195 mg, or as an oral dose of about 65 mg, about 130 mg or about 195 mg.

In at least one embodiment, the miglustat is administered as a pharmaceutically acceptable dosage form suitable for oral administration, and includes but is not limited to tablets, capsules, ovules, elixirs, solutions or suspensions, gels, syrups, mouth washes, or a dry powder for reconstitution with water or other suitable vehicle before use, optionally with flavoring and coloring agents for immediate-, delayed-, modified-, sustained-, pulsed- or controlled-release applications. Solid compositions such as tablets, capsules, lozenges, pastilles, pills, boluses, powder, pastes, granules, bullets, dragées or premix preparations can also be used. In at least one embodiment, the miglustat is administered as a tablet. In at least one embodiment, the miglustat is administered as a capsule. In at least one embodiment, the dosage form contains from about 50 mg to about 300 mg of miglustat. In at least one embodiment, the dosage form contains about 65 mg of miglustat. In at least one embodiment, the dosage form contains about 130 mg of miglustat. In at least one embodiment, the dosage form contains about 260 mg of miglustat. It is contemplated that when the dosage form contains about 65 mg of miglustat, the miglustat can be administered as a dosage of four dosage forms, or a total dose of 260 mg of miglustat. However, for patients who have a significantly lower weight than an average adult weight of 70 kg, including but not limited to infants, children or underweight adults, the miglustat can be administered as a dosage of one dosage form (a total dose of 65 mg of miglustat), two dosage forms (a total dose of 130 mg of miglustat), or three dosage forms (a total dose of 195 mg of miglustat).

Solid and liquid compositions for oral use can be prepared according to methods well known in the art. Such compositions can also contain one or more pharmaceutically acceptable carriers and excipients which can be in solid or liquid form. Tablets or capsules can be prepared by conventional means with pharmaceutically acceptable excipients, including but not limited to binding agents, fillers, lubricants, disintegrants or wetting agents. Suitable pharmaceutically acceptable excipients are known in the art and include but are not limited to pregelatinized starch, polyvinylpyrrolidone, povidone, hydroxypropyl methylcellulose (HPMC), hydroxypropyl ethylcellulose (HPEC), hydroxypropyl cellulose (HPC), sucrose, gelatin, acacia, lactose, microcrystalline cellulose, calcium hydrogen phosphate, magnesium stearate, stearic acid, glyceryl behenate, talc, silica, corn, potato or tapioca starch, sodium starch glycolate, sodium lauryl sulfate, sodium citrate, calcium carbonate, dibasic calcium phosphate, glycine croscarmellose sodium and complex silicates. Tablets can be coated by methods well known in the art. In at least one embodiment, the miglustat is administered as a formulation available commercially as Zavesca® (Actelion Pharmaceuticals).

In at least one embodiment, the miglustat and the recombinant human acid α-glucosidase are administered simultaneously. In at least one embodiment, the miglustat and the recombinant human acid α-glucosidase are administered sequentially. In at least one embodiment, the miglustat is administered prior to administration of the recombinant human acid α-glucosidase. In at least one embodiment, the miglustat is administered less than three hours prior to administration of the recombinant human acid α-glucosidase. In at least one embodiment, the miglustat is administered about two hours prior to administration of the recombinant human acid α-glucosidase. In at least one embodiment, the miglustat is administered less than two hours prior to administration of the recombinant human acid α-glucosidase. In at least one embodiment, the miglustat is administered about 1.5 hours prior to administration of the recombinant human acid α-glucosidase. In at least one embodiment, the miglustat is administered about one hour prior to administration of the recombinant human acid α-glucosidase. In at least one embodiment, the miglustat is administered from about 50 minutes to about 70 minutes prior to administration of the recombinant human acid α-glucosidase. In at least one embodiment, the miglustat is administered from about 55 minutes to about 65 minutes prior to administration of the recombinant human acid α-glucosidase. In at least one embodiment, the miglustat is administered about 30 minutes prior to administration of the recombinant human acid α-glucosidase. In at least one embodiment, the miglustat is administered from about 25 minutes to about 35 minutes prior to administration of the recombinant human acid α-glucosidase. In at least one embodiment, the miglustat is administered from about 27 minutes to about 33 minutes prior to administration of the recombinant human acid α-glucosidase.

In at least one embodiment, the miglustat is administered concurrently with administration of the recombinant human acid α-glucosidase. In at least one embodiment, the miglustat is administered within 20 minutes before or after administration of the recombinant human acid α-glucosidase. In at least one embodiment, the miglustat is administered within 15 minutes before or after administration of the recombinant human acid α-glucosidase. In at least one embodiment, the miglustat is administered within 10 minutes before or after administration of the recombinant human acid α-glucosidase. In at least one embodiment, the miglustat is administered within 5 minutes before or after administration of the recombinant human acid α-glucosidase.

In at least one embodiment, the miglustat is administered after administration of the recombinant human acid α-glucosidase. In at least one embodiment, the miglustat is administered up to 2 hours after administration of the recombinant human acid α-glucosidase. In at least one embodiment, the miglustat is administered about 30 minutes after administration of the recombinant human acid α-glucosidase. In at least one embodiment, the miglustat is administered about one hour after administration of the recombinant human acid α-glucosidase. In at least one embodiment, the miglustat is administered about 1.5 hours after administration of the recombinant human acid α-glucosidase. In at least one embodiment, the miglustat is administered about 2 hours after administration of the recombinant human acid α-glucosidase.

Another aspect of the invention provides a kit for combination therapy of Pompe disease in a patient in need thereof. The kit includes a pharmaceutically acceptable dosage form comprising miglustat, a pharmaceutically acceptable dosage form comprising a recombinant human acid α-glucosidase as defined herein, and instructions for administering the pharmaceutically acceptable dosage form comprising miglustat and the pharmaceutically acceptable dosage form comprising the recombinant acid α-glucosidase to a patient in need thereof. In at least one embodiment, the pharmaceutically acceptable dosage form comprising miglustat is an oral dosage form as described herein, including but not limited to a tablet or a capsule. In at least one embodiment, the pharmaceutically acceptable dosage form comprising a recombinant human acid α-glucosidase is a sterile solution suitable for injection as described herein. In at least one embodiment, the instructions for administering the dosage forms include instructions to administer the pharmaceutically acceptable dosage form comprising miglustat orally prior to administering the pharmaceutically acceptable dosage form comprising the recombinant human acid α-glucosidase by intravenous infusion, as described herein.

Without being bound by theory, it is believed that miglustat acts as a pharmacological chaperone for the recombinant human acid α-glucosidase ATB200 and binds to its active site. For example, miglustat has been found to decrease the percentage of unfolded ATB200 protein and stabilize the active conformation of ATB200, preventing denaturation and irreversible inactivation at the neutral pH of plasma and allowing it to survive conditions in the circulation long enough to reach and be taken up by tissues. However, the binding of miglustat to the active site of ATB200 also can result in inhibition of the enzymatic activity of ATB200 by preventing the natural substrate, glycogen, from accessing the active site. It is believed that when miglustat and the recombinant human acid α-glucosidase are administered to a patient under the conditions described herein, the concentrations of miglustat and ATB200 within the plasma and tissues are such that ATB200 is stabilized until it can be taken up into the tissues and targeted to lysosomes, but, because of the rapid clearance of miglustat, hydrolysis of glycogen by ATB200 within lysosomes is not overly inhibited by the presence of miglustat, and the enzyme retains sufficient activity to be therapeutically useful.

All the embodiments described above may be combined. This includes in particular embodiments relating to:
    the nature of the pharmacological chaperone, for example miglustat; and the active site for which it is specific;
    the dosage, route of administration of the pharmacological chaperone (e.g. miglustat) and the type of pharmaceutical composition including the nature of the carrier and the use of commercially available compositions;

the nature of the drug, e.g. therapeutic protein drug product, which may be a counterpart of an endogenous protein for which expression is reduced or absent in the subject, suitably recombinant human lysosomal protein (e.g. rhGAA), for example the recombinant human acid α-glucosidase expressed in Chinese hamster ovary (CHO) cells and comprising an increased content of N-glycan units bearing one or more mannose-6-phosphate residues when compared to a content of N-glycan units bearing one or more mannose-6-phosphate residues of alglucosidase alfa; and suitably having an amino acid sequence as set forth in SEQ ID NO: 1 or SEQ ID NO: 2;

the number and type of N-glycan units on the recombinant human lysosomal protein (e.g. rhGAA), such as the N-acetylglucosamine, galactose, sialic acid or complex N-glycans formed from combinations of these, attached to the recombinant human lysosomal protein;

the degree of phosphorylation of mannose units on the recombinant human lysosomal protein (e.g. rhGAA) to form mannose-6-phosphate and/or bis-mannose-6-phosphate;

the dosage and route of administration (e.g. intravenous administration, especially intravenous infusion, or direct administration to the target tissue) of the replacement enzyme (e.g. recombinant human acid α-glucosidase) and the type of formulation including carriers and therapeutically effective amount;

the dosage interval of the pharmacological chaperone (miglustat) and the recombinant human acid α-glucosidase;

the nature of the therapeutic response and the results of the combination therapy (e.g. enhanced results as compared to the effect of each therapy performed individually);

the timing of the administration of the combination therapy, e.g. simultaneous administration of miglustat and the recombinant human acid α-glucosidase or sequential administration, for example wherein the miglustat is administered prior to the recombinant human acid α-glucosidase or after the recombinant human acid α-glucosidase or within a certain time before or after administration of the recombinant human acid α-glucosidase; and the nature of the patient treated (e.g. mammal such as human) and the condition suffered by the individual (e.g. enzyme insufficiency).

Any of the embodiments in the list above may be combined with one or more of the other embodiments in the list.

EXAMPLES

Other features of the present invention will become apparent from the following non-limiting examples which illustrate, by way of example, the principles of the invention.

Example 1: Limitations of Existing Myozyme® and Lumizyme® rhGAA Products

To evaluate the ability of the rhGAA in Myozyme® and Lumizyme®, the only currently approved treatments for Pompe disease, these rhGAA preparations were injected onto a CIMPR column (which binds rhGAA having M6P groups) and subsequently eluted with a free M6 gradient. Fractions were collected in 96-well plate and GAA activity assayed by 4MU-α-glucose substrate. The relative amounts of bound and unbound rhGAA were determined based on GAA activity and reported as the fraction of total enzyme.

Figure 4A:
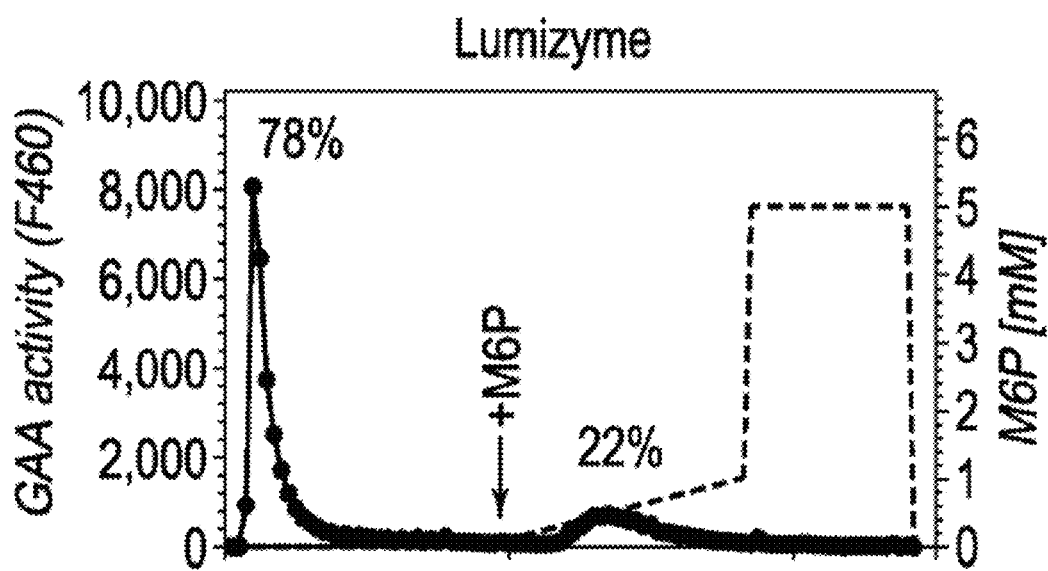
FIGS. 4A and 4B, respectively, are graphs showing the results of CIMPR affinity chromatography of Lumizyme® and Myozyme®. The dashed lines refer to the M6P elution gradient. Elution with M6P displaces GAA molecules bound via an M6P containing glycan to CIMPR.
Figure 4B:
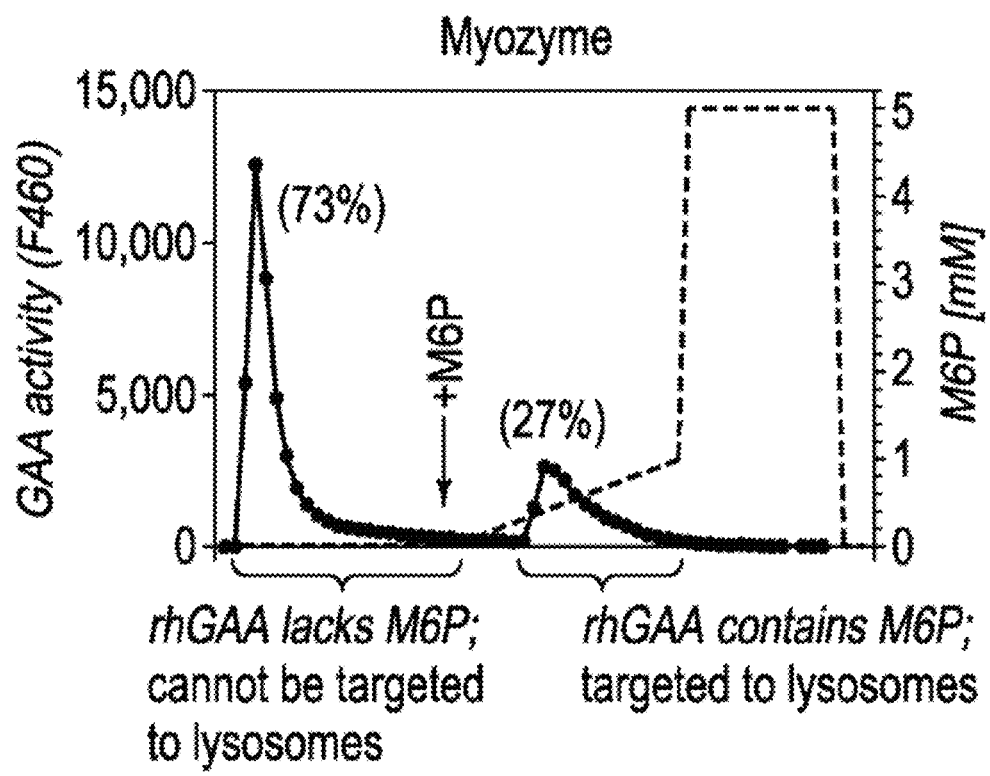

FIGS. 4A-B describe the problems associated with conventional ERTs (Myozyme® and Lumizyme®): 73% of the rhGAA in Myozyme® (FIG. 4B) and 78% of the rhGAA in Lumizyme® (FIG. 4A) did not bind to the CIMPR, see the left-most peaks in each figure. Only 27% of the rhGAA in Myozyme® and 22% of the rhGAA in Lumizyme® contained M6P that can productive to target it to the CIMPR on muscle cells.

An effective dose of Myozyme® and Lumizyme® corresponds to the amount of rhGAA containing M6P which targets the CIMPR on muscle cells. However, most of the rhGAA in these two conventional products does not target the CIMPR receptor on target muscle cells. The administration of a conventional rhGAA where most of the rhGAA is not targeted to muscle cells increases the risk of allergic reaction or induction of immunity to the non-targeted rhGAA.

Figure 5:
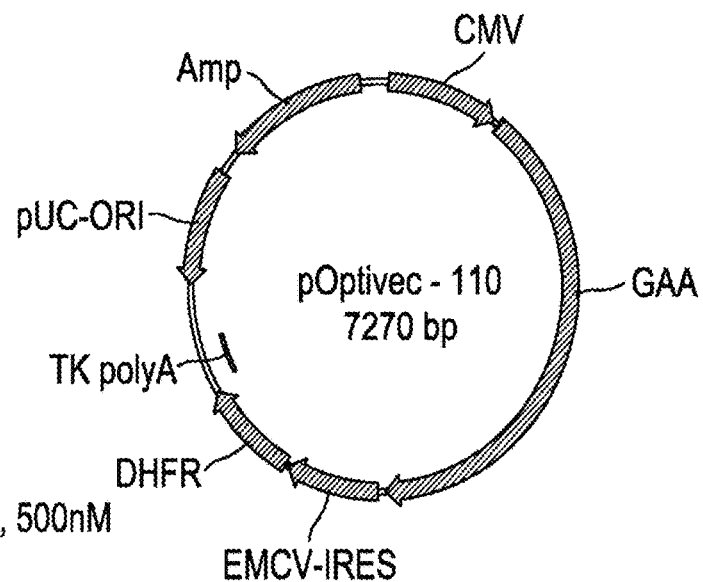
FIG. 5 shows a DNA construct for transforming CHO cells with DNA encoding rhGAA. CHO cells were transformed with a DNA construct encoding rhGAA.

Example 2: Preparation of CHO Cells Producing ATB200 rhGAA Having a High Content of mono- or bis-M6P-Bearing N-Glycans CHO cells were transfected with DNA that expresses rhGAA followed by selection of transformants producing rhGAA. A DNA construct for transforming CHO cells with DNA encoding rhGAA is shown in FIG. 5. CHO cells were transfected with DNA that expresses rhGAA followed by selection of transformants producing rhGAA.

After transfection, DG44 CHO (DHFR-) cells containing a stably integrated GAA gene were selected with hypoxanthine/thymidine deficient (–HT) medium). Amplification of GAA expression in these cells was induced by methotrexate treatment (MTX, 500 nM). Cell pools that expressed high amounts of GAA were identified by GAA enzyme activity assays and were used to establish individual clones producing rhGAA. Individual clones were generated on semisolid media plates, picked by ClonePix system, and were transferred to 24-deep well plates. The individual clones were assayed for GAA enzyme activity to identify clones expressing a high level of GAA. Conditioned media for determining GAA activity used a 4-MU-α-Glucosidase substrate. Clones producing higher levels of GAA as measured by GAA enzyme assays were further evaluated for viability, ability to grow, GAA productivity, N-glycan structure and stable protein expression. CHO cell lines, including CHO cell line GA-ATB-200, expressing rhGAA with enhanced mono-M6P or bis-M6P N-glycans were isolated using this procedure.

Example 3: Capturing and Purification of ATB200 rhGAA

Multiple batches of the rhGAA according to the invention were produced in shake flasks and in perfusion bioreactors using CHO cell line GA-ATB-200 and CIMPR binding was measured. Similar CIMPR receptor binding (~70%) to that shown in FIG. 7B and FIG. 8 was observed for purified ATB200 rhGAA from different production batches indicating that ATB200 rhGAA can be consistently produced. As shown by FIGS. 4A, 4B, 7A and 7B, Myozyme® and Lumizyme® rhGAAs exhibited significantly less CIMPR binding than ATB200 rhGAA.

Example 4: Analytical Comparison of ATB200 to Lumizyme®

Figure 9:
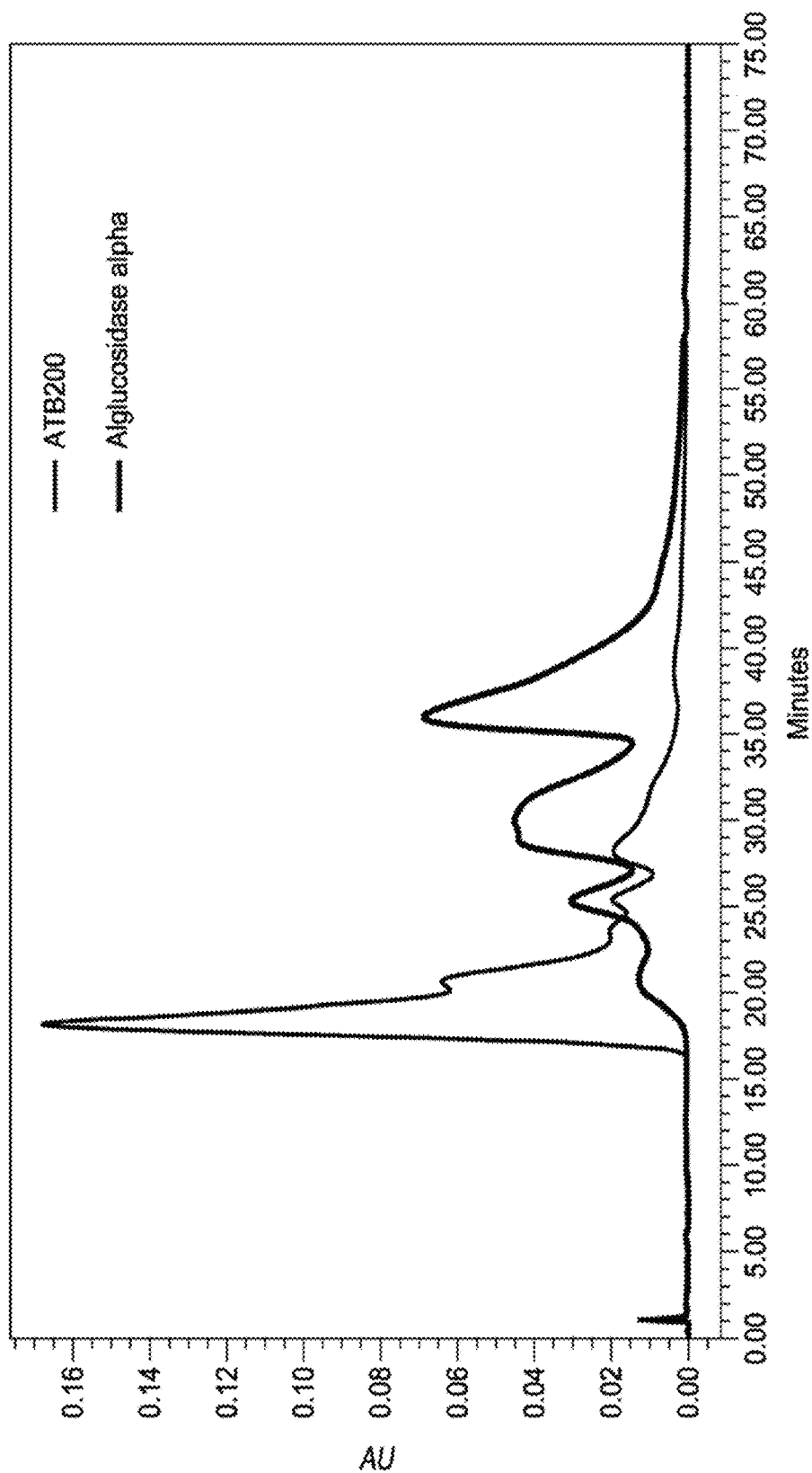
FIG. 9 is a graph showing Polywax elution profiles of Lumizyme® and ATB200 rhGAAs.

Weak anion exchange ("WAX") liquid chromatography was used to fractionate ATB200 rhGAA according to terminal phosphate. Elution profiles were generated by eluting the ERT with increasing amount of salt. The profiles were monitored by UV (A280 nm). ATB200 rhGAA was obtained from CHO cells and purified. Lumizyme® was obtained from a commercial source. Lumizyme® exhibited a high peak on the left of its elution profile. ATB200 rhGAA exhibited four prominent peaks eluting to the right of Lumizyme® (FIG. 9). This confirms that ATB200 rhGAA was phosphorylated to a greater extent than Lumizyme® since this evaluation is by terminal charge rather than CIMPR affinity.

Example 5: Oligosaccharide Characterization of ATB200 rhGAA

Purified ATB200 rhGAA and Lumizyme® glycans were evaluated by MALDI-TOF to determine the individual glycan structures found on each ERT (FIG. 10). ATB200 samples were found to contain lower amounts of non-phosphorylated high-mannose type N-glycans than Lumizyme®. The higher content of M6P glycans in ATB200 than in Lumizyme®, targets ATB200 rhGAA to muscle cells more effectively. The high percentage of mono-phosphorylated and bis-phosphorylated structures determined by MALDI agree with the CIMPR profiles which illustrated significantly greater binding of ATB200 to the CIMPR receptor. N-glycan analysis via MALDI-TOF mass spectrometry confirmed that on average each ATB200 molecule contains at least one natural bis-M6P N-glycan structure. This higher bis-M6P N-glycan content on ATB200 rhGAA directly correlated with high-affinity binding to CIMPR in M6P receptor plate binding assays (KD about 2-4 nM) FIG. 12A.

ATB200 rhGAA was also analyzed for site-specific N-glycan profiles using two different LC-MS/MS analytical techniques. In the first analysis, the protein was denatured, reduced, alkylated and digested prior to LC-MS/MS analysis. During protein denaturation and reduction, 200 μg of protein sample, 5 μL 1 mol/L tris-HCl (final concentration 50 mM), 75 μL 8 mol/L guanidine HCl (final concentration 6 M), 1 μL 0.5 mol/L EDTA (final concentration 5 mM), 2 μL 1 mol/L DTT (final concentration 20 mM) and Milli-Q® water were added to a 1.5 mL tube to provide a total volume of 100 μL. The sample was mixed and incubated at 56° C. for 30 minutes in a dry bath. During alkylation, the denatured and reduced protein sample was mixed with 5 μL 1 mol/L iodoacetamide (IAM, final concentration 50 mM), then incubated at 10-30° C. in the dark for 30 minutes. After alkylation, 400 μL of precooled acetone was added to the sample and the mixture was frozen at −80° C. refrigeration for 4 hours. The sample was then centrifuged for 5 min at 13000 rpm at 4° C. and the supernatant was removed. 400 μL of precooled acetone was added to the pellets, which was then centrifuged for 5 min at 13000 rpm at 4° C. and the supernatant was removed. The sample was then air dried on ice in the dark to remove acetone residue. 40 μL of 8M urea and 160 μL of 100 mM $NH_4HCO_3$ were added to the sample to dissolve the protein. During trypsin digestion, 50 μg of the protein was then added with trypsin digestion buffer to a final volume of 100 μL, and 5 μL 0.5 mg/mL trypsin (protein to enzyme ratio of 20/1 w/w) was added. The solution was mixed well and incubated overnight (16±2 hours) at 37° C. 2.5 μL 20% TFA (final concentration 0.5%) was added to quench the reaction. The sample was then analyzed using the Thermo Scientific Orbitrap Velos Pro™ Mass Spectrometer.

In the second LC-MS/MS analysis, the ATB200 sample was prepared according to a similar denaturation, reduction, alkylation and digestion procedure, except that iodoacetic acid (IAA) was used as the alkylation reagent instead of JAM, and then analyzed using the Thermo Scientific Orbitrap Fusion Lumos Tribid™ Mass Spectrometer.

The results of the first and second analyses are shown in FIGS. 11A-11H. In FIGS. 11A-11H, the results of the first analysis are represented by left bar (dark grey) and the results from the second analysis are represented by the right bar (light grey). In FIGS. 11B-11G, the symbol nomenclature for glycan representation is in accordance with Varki, A., Cummings, R. D., Esko J. D., et al., *Essentials of Glycobiology*, 2nd edition (2009).

Figure 11A:
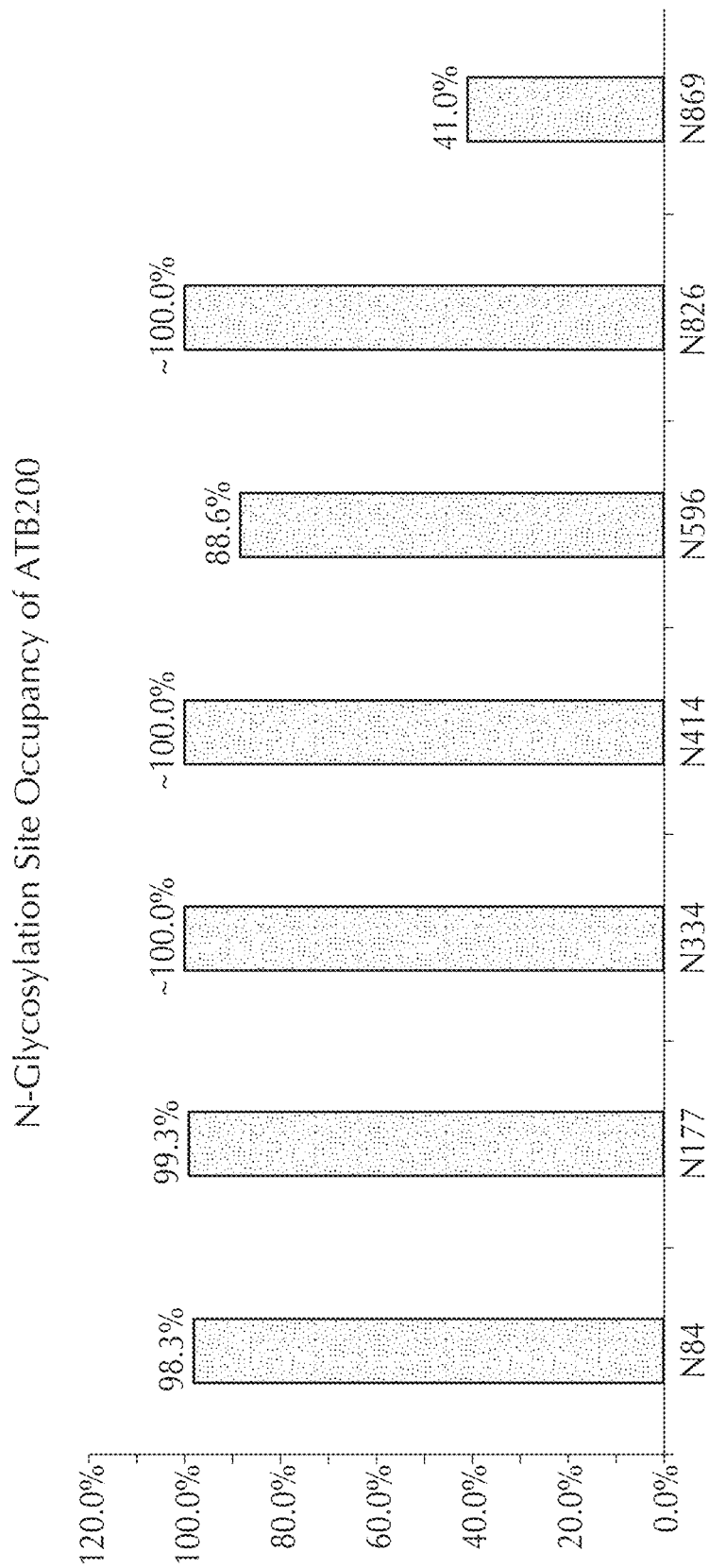
FIGS. 11A-11H show the results of a site-specific N-glycosylation analysis of ATB200 rhGAA.

As can be seen from FIGS. 8A-8I, the two analyses provided similar results, although there was some variation between the results. This variation can be due to a number of factors, including the instrument used and the completeness of N-glycan analysis. For example, if some species of phosphorylated glycans were not identified and/or not quantified, then the total number of phosphorylated glycans may be underrepresented, and the percentage of rhGAA bearing the phosphorylated glycans at that site may be underrepresented. As another example, if some species of non-phosphorylated glycans were not identified and/or not quantified, then the total number of non-phosphorylated glycans may be underrepresented, and the percentage of rhGAA bearing the phosphorylated glycans at that site may be overrepresented. FIG. 11A shows the N-glycosylation site occupancy of ATB200. As can be seen from FIG. 11A, the first, second, third, fourth, fifth and sixth N-glycosylation sites are mostly occupied, with both analyses detecting over 90% and up to about 100% of the ATB200 enzyme having a glycan detected at each potential site. However, the seventh potential N-glycosylation site is glycosylated about half of the time.

Figure 11B:
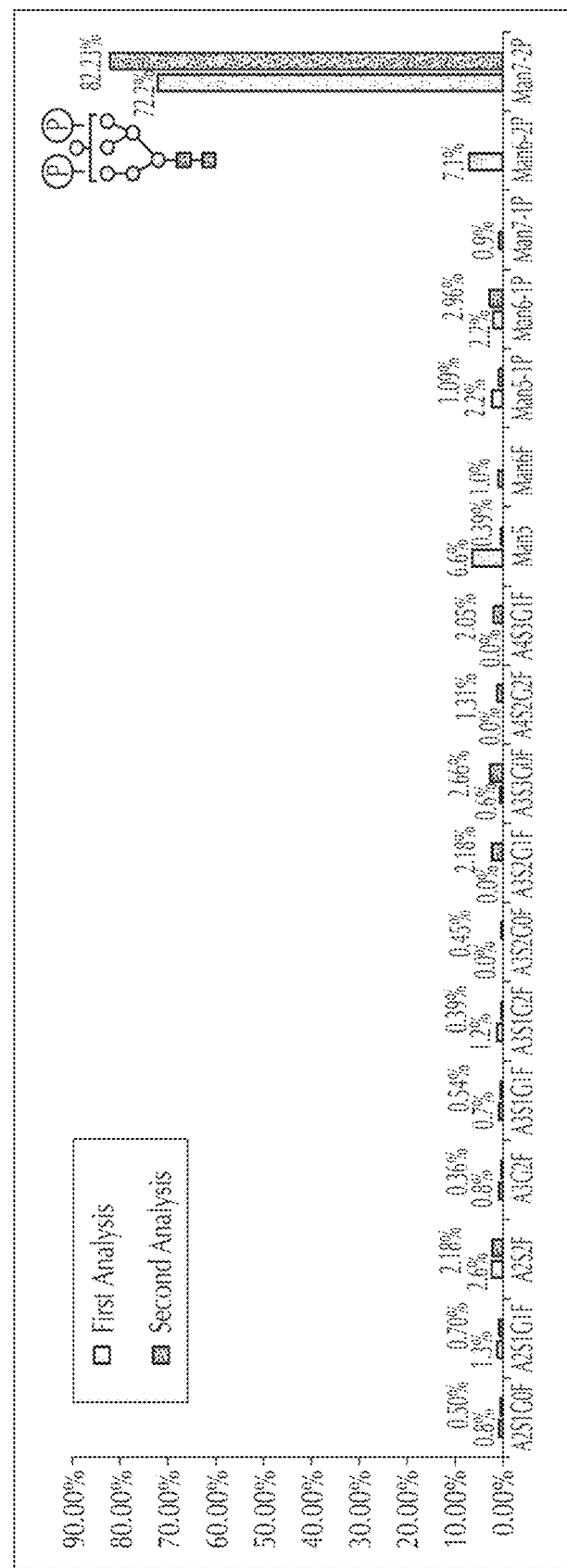

FIG. 11B shows the N-glycosylation profile of the first site, N84. As can be seen from FIG. 11B, the major glycan species is bis-M6P glycans. Both the first and second analyses detected over 75% of the ATB200 had a bis-M6P glycan at the first site.

Figure 11C:
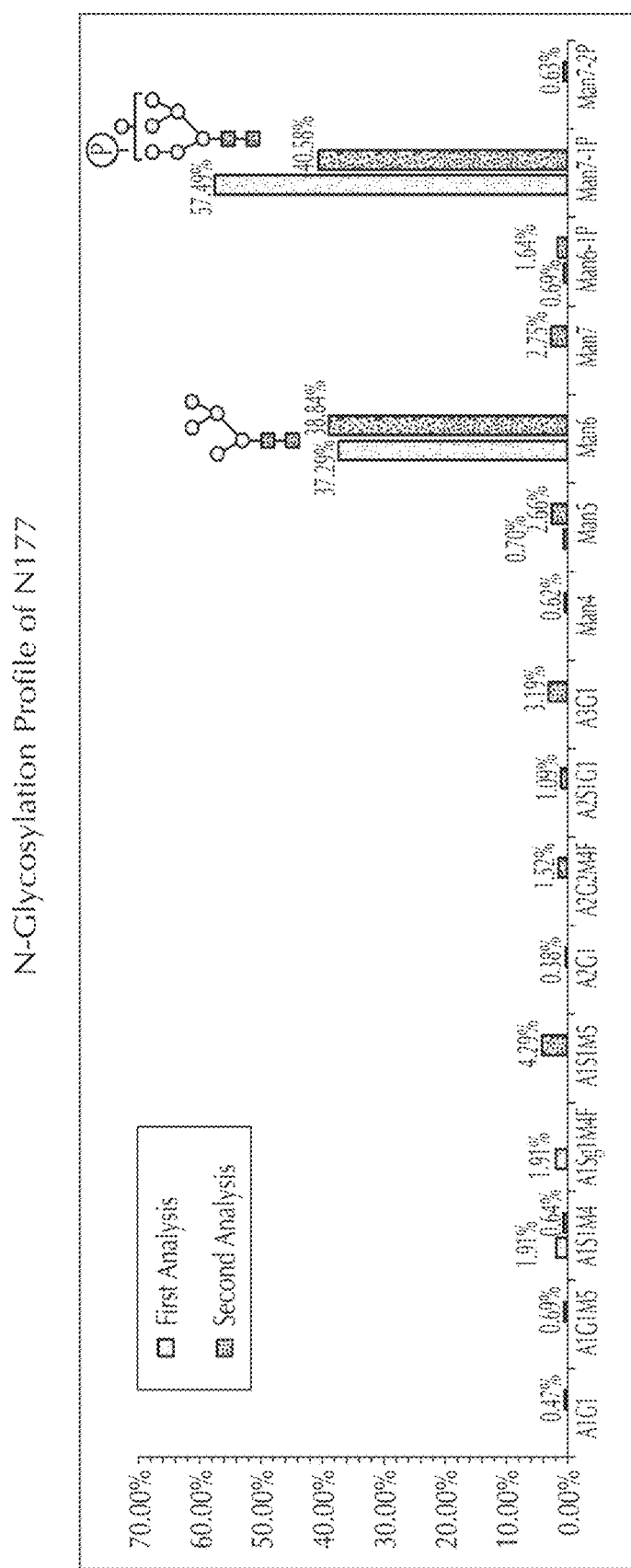

FIG. 11C shows the N-glycosylation profile of the second site, N177. As can be seen from FIG. 11C, the major glycan species are mono-M6P glycans and non-phosphorylated high mannose glycans. Both the first and second analyses detected over 40% of the ATB200 had a mono-M6P glycan at the second site.

Figure 11D:
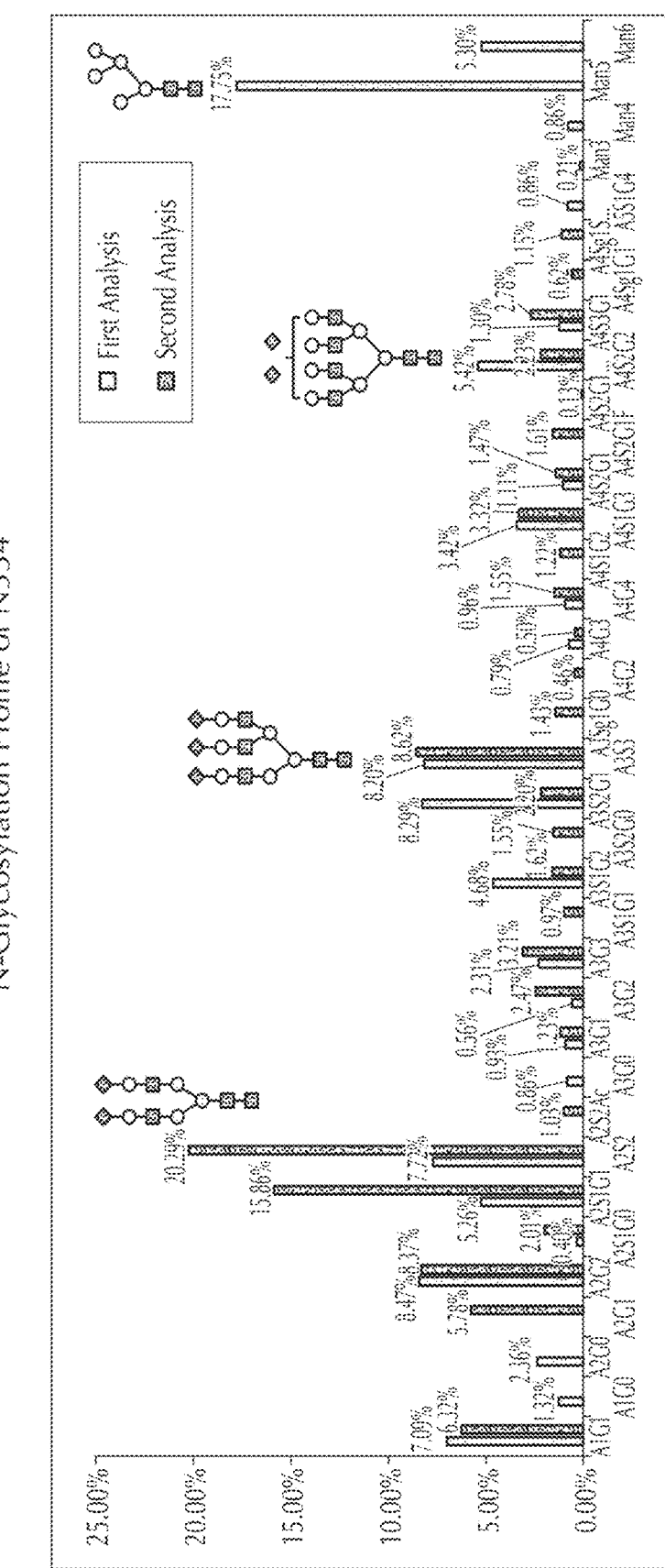

FIG. 11D shows the N-glycosylation profile of the third site, N334. As can be seen from FIG. 11D, the major glycan species are non-phosphorylated high mannose glycans, di-, tri-, and tetra-antennary complex glycans, and hybrid glycans. Both the first and second analyses detected over 20% of the ATB200 had a sialic acid residue at the third site.

Figure 11E:
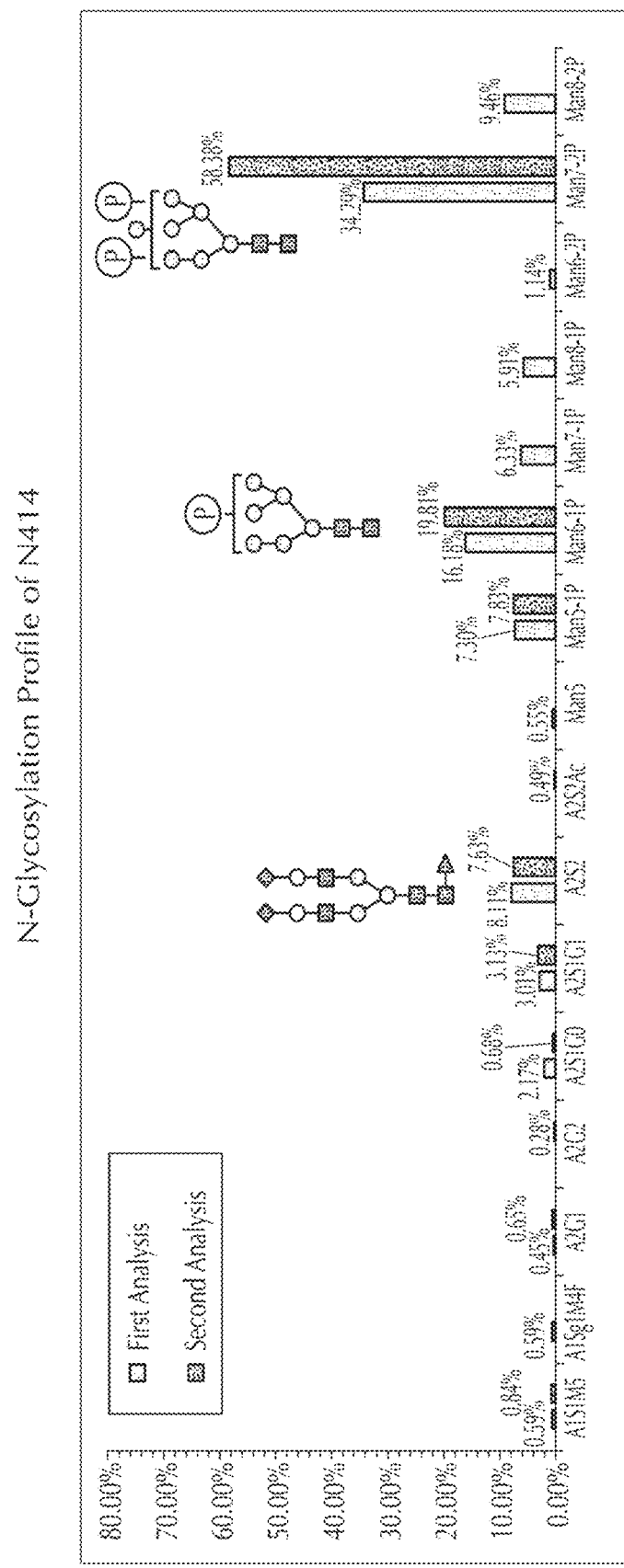

FIG. 11E shows the N-glycosylation profile of the fourth site, N414. As can be seen from FIG. 11E, the major glycan species are bis-M6P and mono-MGP glycans. Both the first and second analyses detected over 40% of the ATB200 had a bis-M6P glycan at the fourth site. Both the first and second analyses also detected over 25% of the ATB200 had a mono-M6P glycan at the fourth site.

Figure 11F:
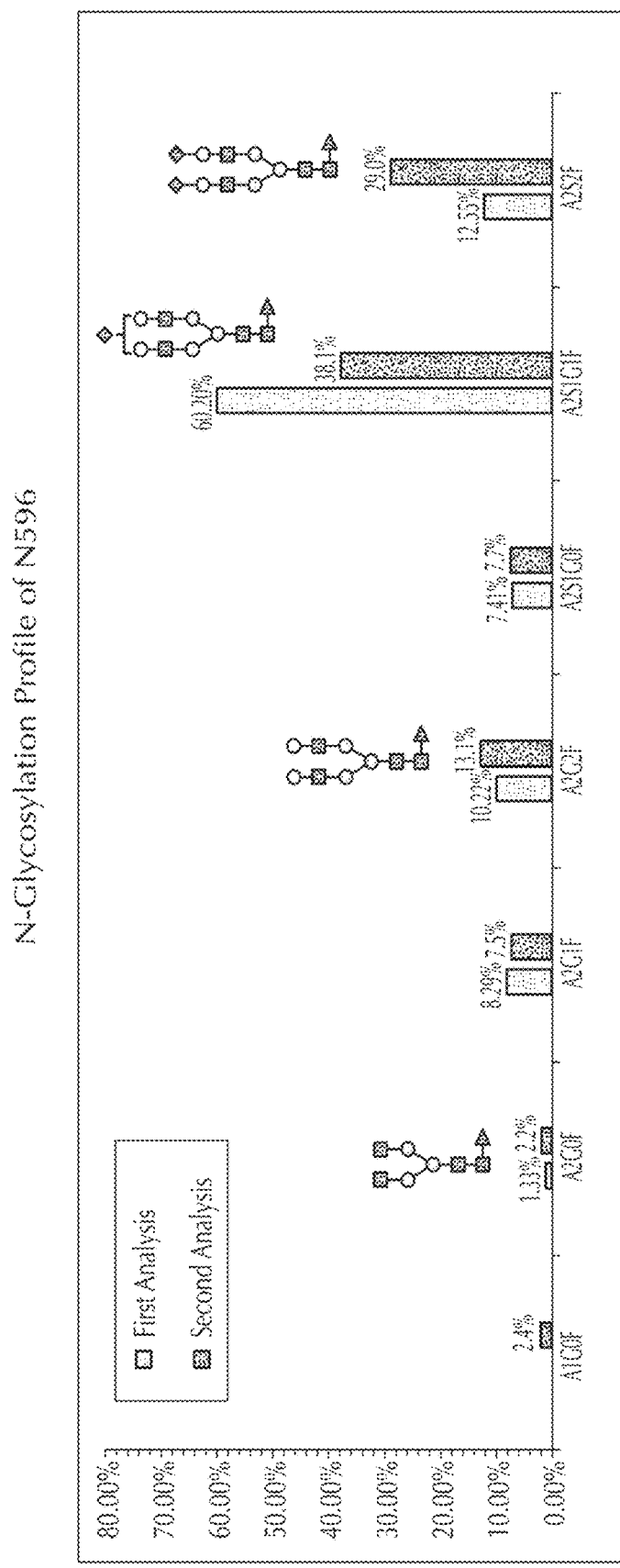

FIG. 11F shows the N-glycosylation profile of the fifth site, N596. As can be seen from FIG. 11F, the major glycan species are fucosylated di-antennary complex glycans. Both the first and second analyses detected over 70% of the ATB200 had a sialic acid residue at the fifth site.

Figure 11G:
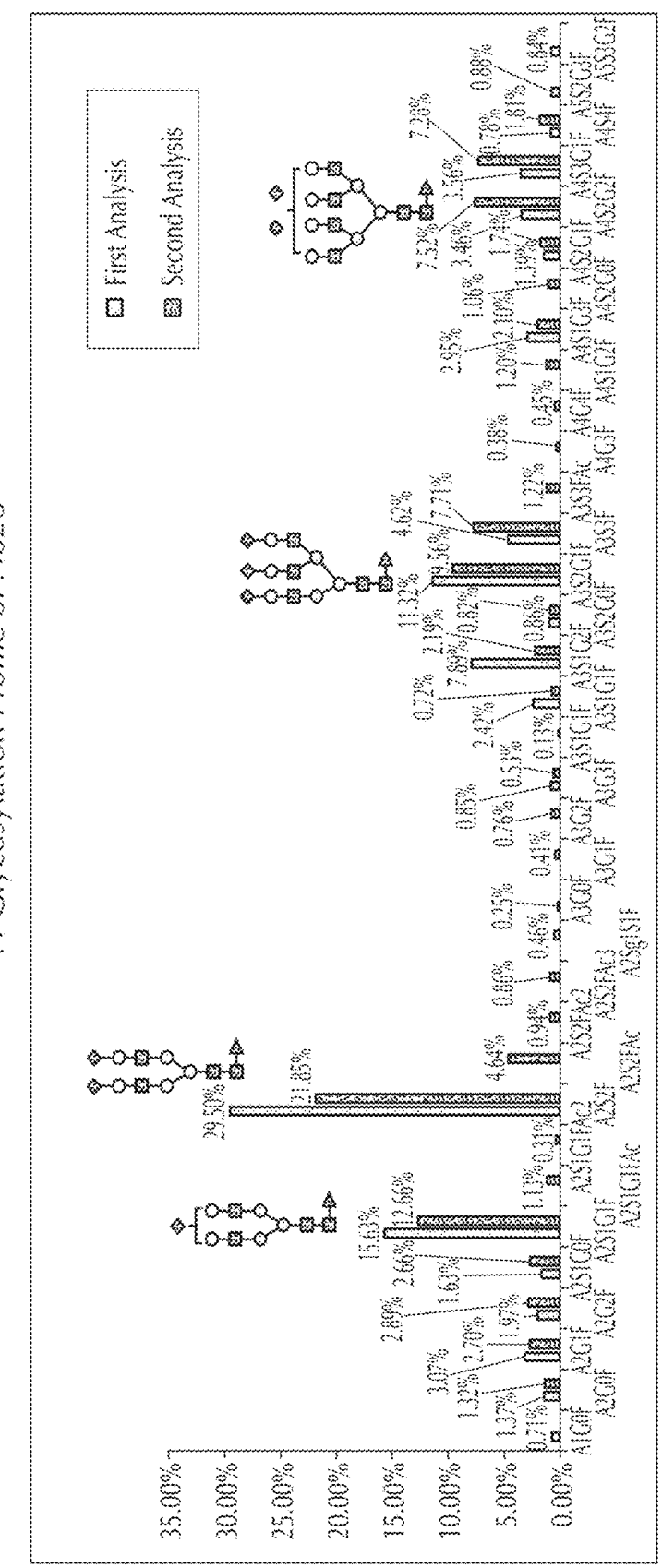

FIG. 11G shows the N-glycosylation profile of the sixth site, N826. As can be seen from FIG. 11G, the major glycan species are di-, tri-, and tetra-antennary complex glycans. Both the first and second analyses detected over 80% of the ATB200 had a sialic acid residue at the sixth site.

An analysis of the glycosylation at the seventh site, N869, showed approximately 40% glycosylation, with the most common glycans being A4S3S3GF (12%), A5S3G2F (10%), A4S2G2F (8%) and A6S3G3F (8%).

Figure 11H:
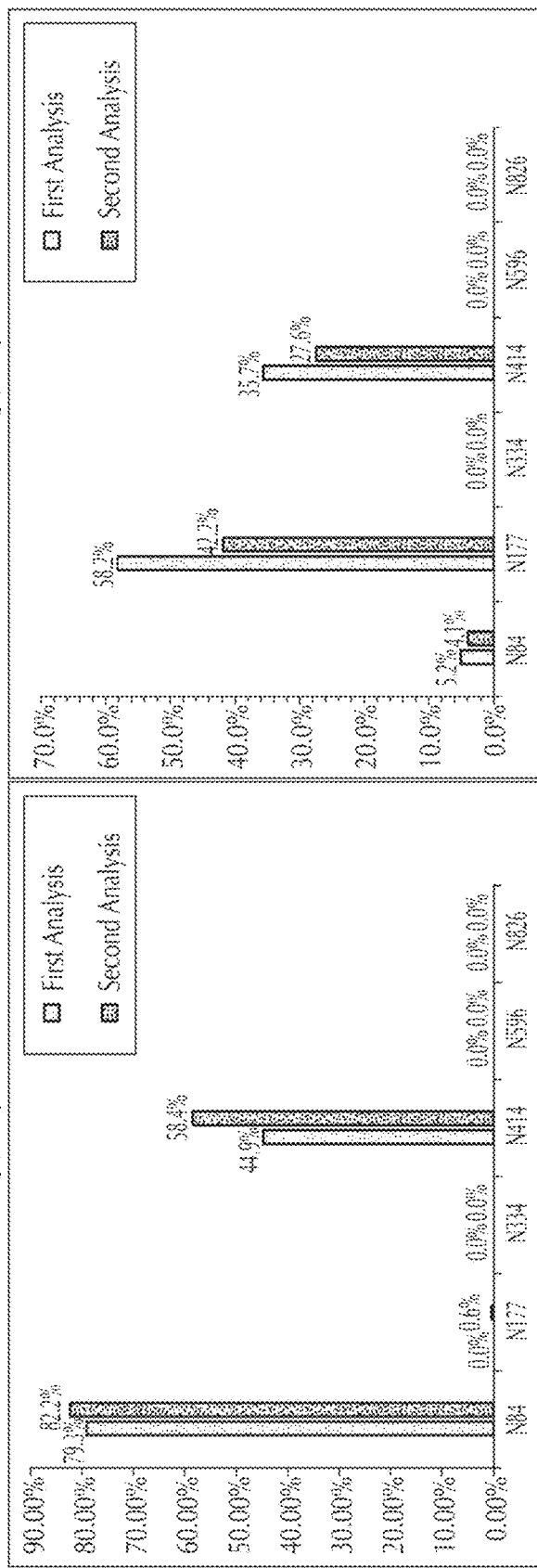

FIG. 11H shows a summary of the phosphorylation at each of the seven potential N-glycosylation sites. As can be seen from FIG. 11H, both the first and second analyses detected high phosphorylation levels at the first, second and fourth sites. Both analyses detected over 80% of the ATB200 was mono- or di-phosphorylated at the first site, over 40% of the ATB200 was mon-phosphorylated at the second site, and over 80% of the ATB200 was mono- or di-phosphorylated at the fourth site.

Another glycan analysis of ATB200 was performed according to a hydrophilic interaction liquid chromatography-fluorescent detection-mass spectrometry (HILIC-FLD-MS) method.

The results of HILIC-FLD-MS analysis are provided in Table 5 below: In Table 5, the first number in the three-digit number indicates the number of branches in the glycan, the second number indicates the number of core fucose units and the third number indicates the number of terminal sialic acid units. Using this nomenclature, "303" represents a tri-antennary glycan (the first 3) with 0 core fucose (the 2nd 0) and 3 terminal sialic acids (the last 3), "212" represents a bi-antennary glycan with 1 core fucose and 2 terminal sialic acids, "404" represents a tetra-antennary glycan with 0 core fucose and 4 terminal sialic acids, etc.

TABLE 5

| FLD Peak Number | MS Peak Number | RT (min) | Glycan Structure | % Peak Area |
|---|---|---|---|---|
| 1 | 1 | | BisP__Man 8 | 2.83% |
| 2 | 2 | 13.41 | BisP__Man 7 | 17.58% |
| | 3 | 14.30 | BisP__Man 6 | 1.02% |
| 3 | 4 | 20.89 | MonoP__Man 6 | 2.34% |
| 4 | 5 | 21.65 | MonoP__Man 5 | 1.16% |
| 5 | 6 | 23.51 | MonoP__Man 8 | 1.28% |
| 6 | 7 | 24.33 | MonoP__Man 7 | 4.35% |
| 7 | 8 | 25.61 | MonoP__Man 7 __(+)GlcNAc | 0.50% |
| 8 | 9 | 28.76 | MonoP__hMan6__101 | 0.48% |
| 9 | 10 | 30.54 | MonoP__Man 6__(+)GlcNAc | 0.68% |
| 10 | 11 | 33.50 | Man 6 | 3.97% |
| | 12 | 33.65 | 303 | 0.74% |
| 11 | 13 | 34.97 | Man 7 | 0.20% |
| 12 | 14 | 35.64 | 403 | 0.39% |
| 13 | 15 | 36.61 | 302 | 0.36% |
| 14 | 16 | 38.07 | 302 | 0.61% |
| 15 | 17 | 38.53 | Man 5 | 1.85% |
| 16 | 18 | 39.57 | 302 | 0.48% |
| | 19 | 39.78 | hMan 5__101 | 0.42% |
| | 20 | 40.05 | hMan 5__100__(−)Gal | 0.30% |
| 17 | 21 | 40.77 | 301__(−)Gal | 0.52% |
| | 22 | 40.58 | 301 | 0.50% |
| 18 | 23 | 41.47 | 300__(−)Gal | 0.80% |
| 19 | 24 | 42.17 | 301__(−)Gal | 0.11% |
| | 25 | 42.13 | 301 | 0.58% |
| 20 | 26 | 42.89 | 301__(−)Gal | 0.07% |
| | 27 | 42.79 | 301 | 0.80% |
| 21 | 28 | 43.41 | 300 | 0.85% |
| | 29 | 43.28 | 101 | 0.39% |
| 22 | 30 | 43.94 | 202 | 0.63% |
| 23 | 31 | 44.45 | 401 | 0.39% |
| 24 | 32 | 45.04 | MonoP__hMan6__111 | 0.36% |
| 25 | 33 | 45.69 | MonoP__hMan6__111 | 1.45% |
| | 34 | 45.90 | 100 | 0.23% |
| | 35 | 45.90 | 400 | 0.19% |
| 26 | 36 | 46.87 | 201 | 0.49% |
| | 37 | 47.15 | 202 | 0.34% |
| 27 | 38 | 48.19 | 414 | 0.37% |
| 28 | 39 | 48.94 | 202 | 1.97% |
| 29 | 40 | 50.79 | MonoP__Man 6 __110__(−)Gal | 1.31% |
| | 41 | 51.37 | 414 | 0.62% |
| 30 | 42 | 52.22 | 313 | 0.74% |
| | 43 | 52.42 | 201__(−)Gal | 0.46% |
| | 44 | 52.42 | 201 | 1.18% |
| | 45 | 53.11 | hMan6__111 | 0.20% |
| 31 | 46 | 53.83 | 200__(−)Gal | 0.80% |
| | 47 | 54.23 | 201 | 1.27% |
| | 48 | 54.75 | 413 | 0.30% |
| 32 | 49 | 55.47 | 200 | 1.30% |
| 33 | 50 | 57.45, 58.34 | 414__(+)GlcNAcGal | 0.14% |
| | 51 | 56.62, 56.91, 57.99 | 413 | 0.94% |
| | 52 | 56.11, 57.26, 57.99 | 312 | 0.98% |
| 34 | 53 | 60.19 | 413 | 0.33% |
| | 54 | 59.39 | 413__(+)GlcNAcGal | 0.42% |
| | 55 | 59.80 | 312 | 0.52% |
| | 56 | 59.49 | 412 | 0.18% |
| 35 | 57 | 60.75 | 413 | 0.78% |
| | 58 | 60.89 | 413__(+)GlcNAcGal | 0.07% |
| 36 | 59 | 61.79 | 413 | 0.20% |
| | 60 | 61.75 | 312 | 0.16% |
| | 61 | 62.12 | 412 | 0.64% |
| 37 | 62 | 63.87 | 311 | 0.73% |
| | 63 | 63.18, 64.32 | 412 | 0.29% |
| | 64 | 63.84 | 413__(+)GlcNAcGal | 0.45% |
| | 65 | 63.5, 64.36 | 311__(−)Gal | 0.42% |
| 38 | 66 | 65.73, 66.20 | 311 | 0.68% |
| | 67 | 65.85, 66.49 | 412 | 0.72% |
| | 68 | 65.91 | 310__(−)Gal | 0.28% |
| 39 | 69 | 67.37 | 212 | 1.42% |
| | 70 | 67.57 | 310 | 0.34% |
| 40 | 71 | 68.67 | 412__(+)GlcNAcGal | 0.24% |
| | 72 | 68.36 | 412 | 0.53% |
| 41 | 73 | 68.36 | 412__(+)GlcNAcGal | 0.17% |
| | 74 | 69.03 | 412 | 0.35% |
| | 75 | 69.30 | 413__(+)2(GlcNAcGal) | 0.16% |
| 42 | 76 | 70.66 | 412__(+)GlcNAcGal | 0.73% |
| 43 | 77 | 71.74 | 211 | 1.09% |
| | 78 | 71.23 | 211__(−)Gal | 0.19% |
| 44 | 79 | 72.46 | 212 | 3.66% |
| 45 | 80 | 74.82 | 221__(−)Gal(+)GalNAc | 0.38% |
| | 81 | 74.43, 74.96 | 411__(+)GlcNAcGal | 0.66% |
| 46 | 82 | 75.92 | 410 | 0.42% |
| 47 | 83 | 76.73, 77.87 | 211__(−)Gal | 1.24% |
| | 84 | 77.23 | 211 | 3.64% |
| 48 | 85 | 79.05 | 211 | 1.52% |
| | 86 | 79.38 | 210__(−)2Gal | 0.45% |
| 49 | 87 | 80.11 | 210__(−)Gal | 1.58% |
| 50 | 88 | 81.15 | 210 | 2.41% |
| 51 | 89 | 84.22-87.15 | 311 | 1.26% |
| 52 | 90 | 95.35 | Mono__Acetyl__NANA__212 | 0.99% |
| 53 | 91 | 96.23 | Mono__Acetyl__NANA__211 | 0.76% |
| 54 | 92 | 97.37 | Bis__Acetyl__NANA__212 | 0.42% |

Based on this HILIC-FLD-MS analysis, the ATB200 tested is expected to have an average fucose content of 2-3 mol per mol of ATB200, GlcNAc content of 20-25 mol per mol of ATB200, galactose content of 8-12 mol per mol of ATB200, mannose content of 22-27 mol per mol of ATB200, M6P content of 3-5 mol per mol of ATB200 and sialic acid content of 4-7 mol of ATB200.

Example 6: Characterization of CIMPR Affinity of ATB200

Figures 12A, 12B:
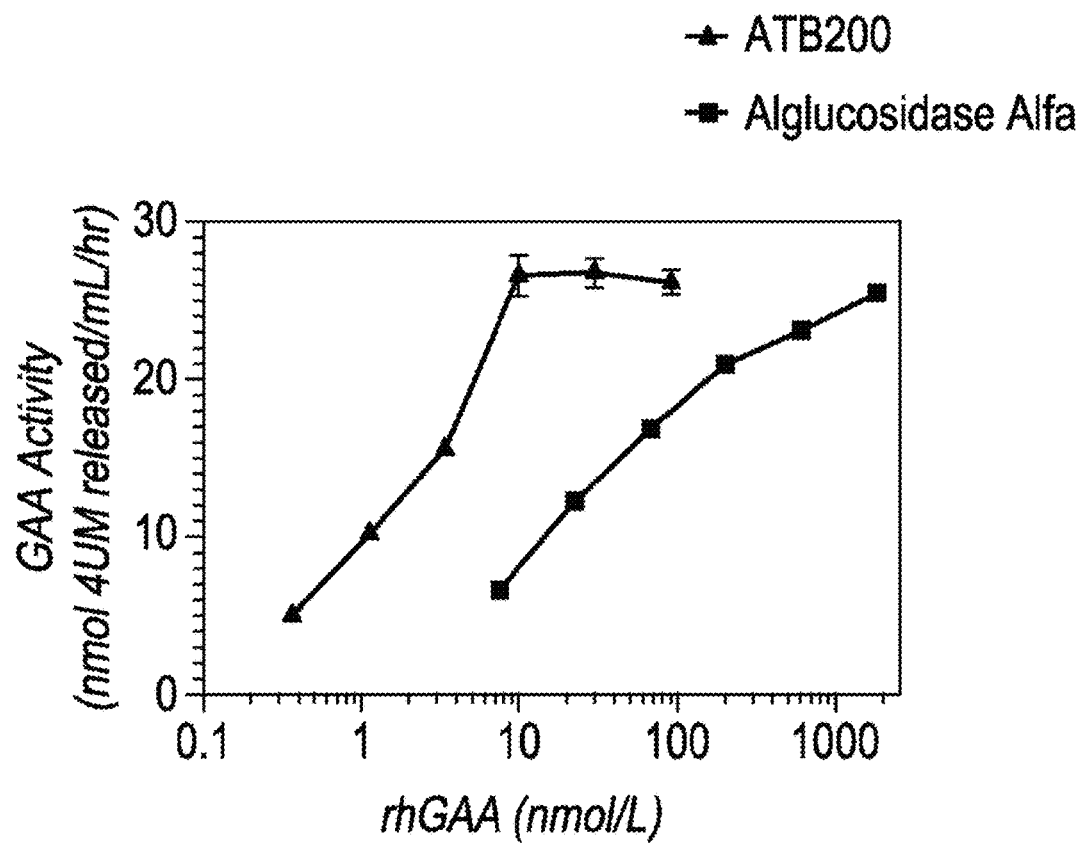
FIG. 12A is a graph comparing the CIMPR binding affinity of ATB200 rhGAA (left trace) with that of Lumizyme® (right trace).
FIG. 12B is a table comparing the Bis-M6P content of Lumizyme® and ATB200 rhGAA.

In addition to having a greater percentage of rhGAA that can bind to the CIMPR, it is important to understand the quality of that interaction. Lumizyme® and ATB200 rhGAA receptor binding was determined using a CIMPR plate binding assay. Briefly, CIMPR-coated plates were used to capture GAA. Varying concentrations of rhGAA were applied to the immobilized receptor and unbound rhGAA was washed off. The amount of remaining rhGAA was determined by GAA activity. As shown by FIG. 12A, ATB200 rhGAA bound to CIMPR significantly better than Lumizyme®.

FIG. 12B shows the relative content of bis-M6P glycans in Lumizyme®, a conventional rhGAA, and ATB200 according to the invention. For Lumizyme® there is on average only 10% of molecules have a bis-phosphorylated glycan. Contrast this with ATB200 where on average every rhGAA molecule has at least one bis-phosphorylated glycan.

Example 7: ATB200 rhGAA was More Efficiently Internalized by Fibroblast than Lumizyme The relative cellular uptake of ATB200 and Lumizyme® rhGAA were compared using normal and Pompe fibroblast cell lines. Comparisons involved 5-100 nM of ATB200 rhGAA according to the invention with 10-500 nM conventional rhGAA Lumizyme®. After 16-hr incubation, external rhGAA was inactivated with TRIS base and cells were washed 3-times with PBS prior to harvest. Internalized GAA measured by 4MU-α-Glucoside hydrolysis and was graphed relative to total cellular protein and the results appear in FIGS. 13A-B.

ATB200 rhGAA was also shown to be efficiently internalized into cells (FIGS. 13A and 13B), respectively, show that ATB200 rhGAA is internalized into both normal and Pompe fibroblast cells and that it is internalized to a greater degree than conventional Lumizyme® rhGAA. ATB200 rhGAA saturates cellular receptors at about 20 nM, while about 250 nM of Lumizyme® is needed. The uptake efficiency constant ($K_{uptake}$) extrapolated from these results is 2-3 nm for ATB200 and 56 nM for Lumizyme® as shown by FIG. 13C. These results suggest that ATB200 rhGAA is a well-targeted treatment for Pompe disease.

Example 8: Glycogen Reduction in Gaa-Knockout Mice

Figure 14A:
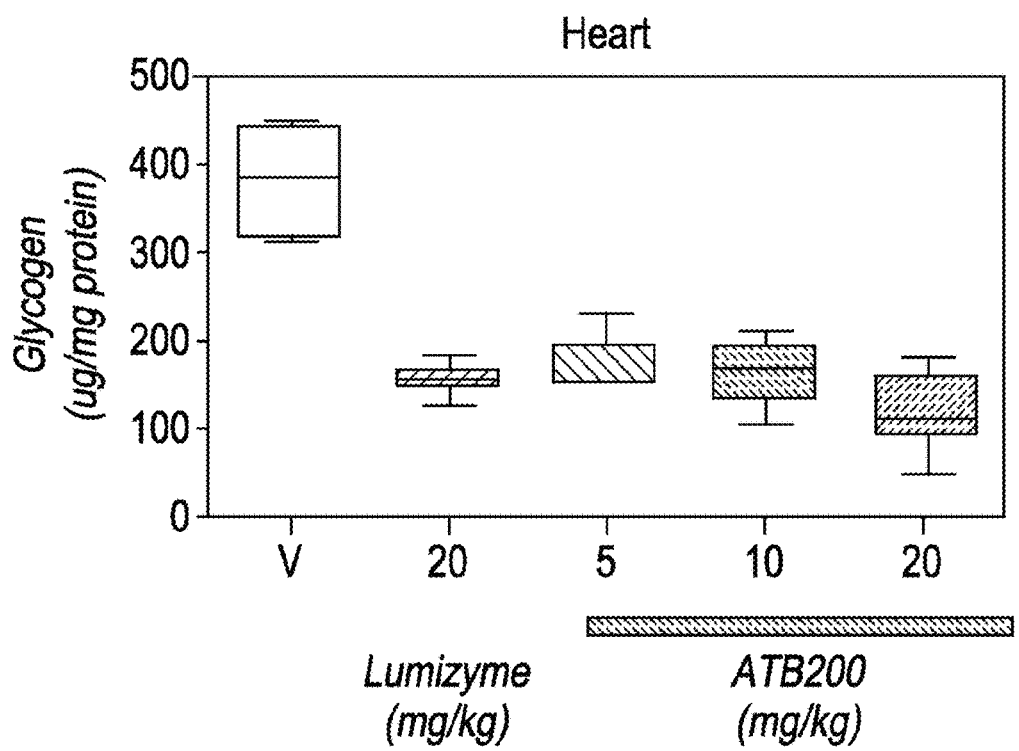
FIG. 14A is a graph showing the amount of glycogen relative to dose of recombinant human acid α-glucosidase in mouse heart muscle after contact with vehicle (negative control), with 20 mg/ml alglucosidase alfa (Lumizyme®), or with 5, 10 or 20 mg/kg ATB200.
Figure 14B:
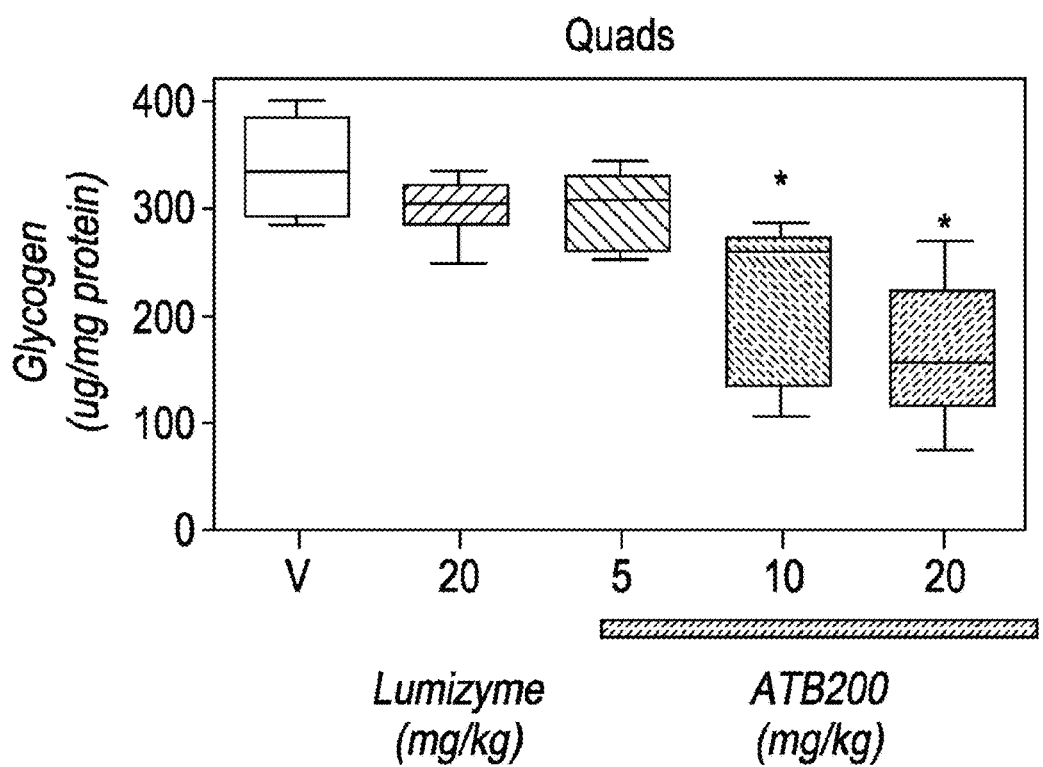
FIG. 14B is a graph showing the amount of glycogen relative to dose of recombinant human acid α-glucosidase in mouse quadriceps muscle after contact with vehicle (negative control), with 20 mg/ml alglucosidase alfa (Lumizyme®), or with 5, 10 or 20 mg/kg ATB200.
Figures 14C, 15:
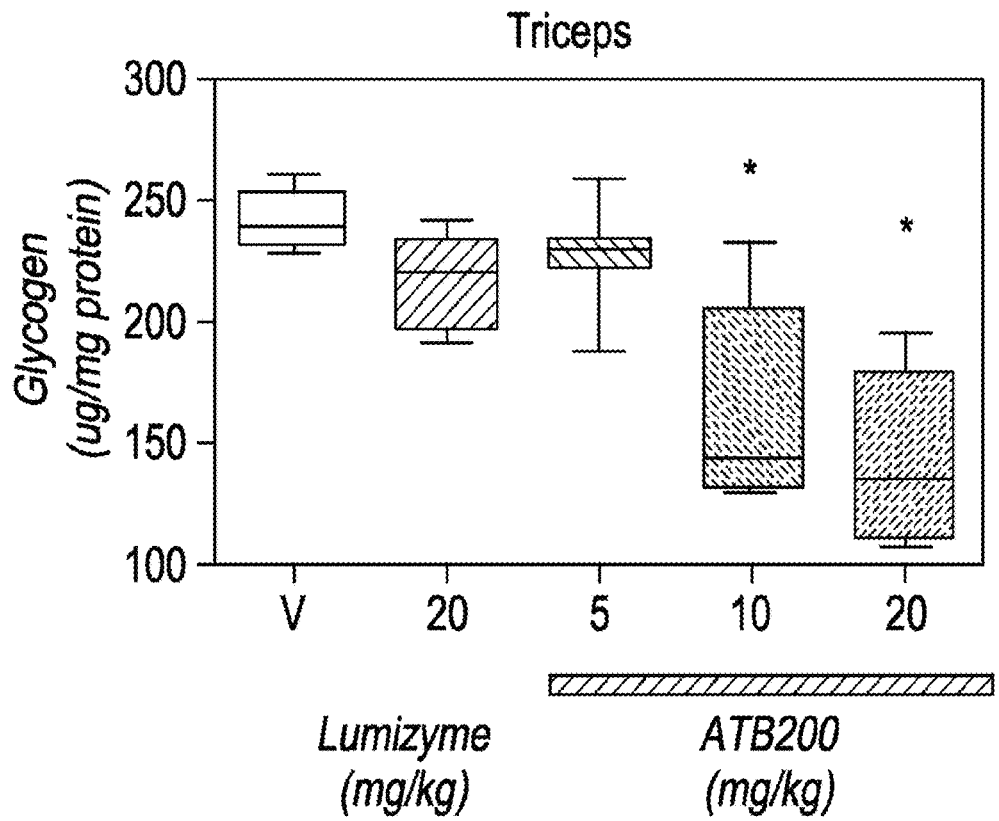
FIG. 14C is a graph showing the amount of glycogen relative to dose of recombinant human acid α-glucosidase in mouse triceps muscle after contact with vehicle (negative control), with 20 mg/ml alglucosidase alfa (Lumizyme®), or with 5, 10 or 20 mg/kg ATB200.
FIG. 15 is a table showing that the combination of ATB200 rhGAA and chaperone miglustat provided significantly better glycogen clearance in GAA knock-out mice than treatments with either Lumizyme® or ATB200 rhGAAs without the miglustat chaperone.

FIGS. 14A to 14C show the effects of administering alglucosidase alfa (Lumizyme®) and ATB200 on glycogen clearance in Gaa knockout mice. Animals were given two IV bolus administrations (every other week); tissues were harvested two weeks after the last dose and analyzed for acid α-glucosidase activity and glycogen content.

As seen from FIGS. 14A to 14C, ATB200 was found to deplete tissue glycogen in acid α-glucosidase (Gaa) knockout mice in a dose-dependent fashion. The 20 mg/kg dose of ATB200 consistently removed a greater proportion of stored glycogen in Gaa knockout mice than the 5 and 10 mg/kg dose levels. However, as seen in FIGS. 14A to 14C, ATB200 administered at 5 mg/kg showed a similar reduction of glycogen in mouse heart and skeletal muscles (quadriceps and triceps) to Lumizyme® administered at 20 mg/kg, while ATB200 dosed at 10 and 20 mg/kg showed significantly better reduction of glycogen levels in skeletal muscles than Lumizyme®.

FIG. 15 shows the effects of administering alglucosidase alfa (Lumizyme®) and ATB200 on glycogen clearance in Gaa knockout mice, as well as the effect of co-administration of ATB200 and miglustat on glycogen clearance. Twelve week old GAA KO mice treated with Lumizyme® or ATB200, 20 mg/kg IV every other week 4 injections; miglustat was co-administered at 10 mg/kg PO, 30 min prior to rhGAA as indicated. Tissues were collected 14 days after last enzyme dose for glycogen measurement. FIG. 15 shows the relative reduction of glycogen in quadriceps and triceps skeletal muscle, with ATB200 providing a greater reduction of glycogen than Lumizyme®, and ATB200/miglustat providing an even greater reduction of glycogen.

Example 9: Muscle Physiology and Morphology in Gaa-Knockout Mice

Gaa knockout mice were given two IV bolus administrations of recombinant human acid α-glucosidase (alglucosidase alfa or ATB200) at 20 mg/kg every other week. Miglustat was orally administered at dosages of 10 mg/kg to a subset of animals treated with ATB200 30 mins prior to administration of ATB200. Control mice were treated with vehicle alone. Soleus, quadriceps and diaphragm tissue is harvested two weeks after the last dose of recombinant human acid α-glucosidase. Soleus and diaphragm tissue were analyzed for glycogen levels, by staining with periodic acid—Schiff reagent (PAS), and for lysosome proliferation, by measuring levels of the lysosome-associated membrane protein (LAMP1) marker, which is upregulated in Pompe disease. Semi-thin sections of quadriceps muscle embedded in epoxy resin (Epon) were stained with methylene blue and observed by electron microscopy (1000×) to determine the extent of the presence of vacuoles. Quadriceps muscle samples were analyzed immunohistochemically to determine levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

In a similar study, Gaa knockout mice were given four IV bolus administrations of recombinant human acid α-glucosidase (alglucosidase alfa or ATB200) at 20 mg/kg every other week. Miglustat was orally administered at dosages of 10 mg/kg to a subset of animals treated with ATB200 30 mins prior to administration of ATB200. Control mice were treated with vehicle alone. Cardiac muscle tissue was harvested two weeks after the last dose of recombinant human acid α-glucosidase and analyzed for glycogen levels, by staining with periodic acid—Schiff reagent (PAS), and for lysosome proliferation, by measuring levels of LAMP1.

Figure 16:
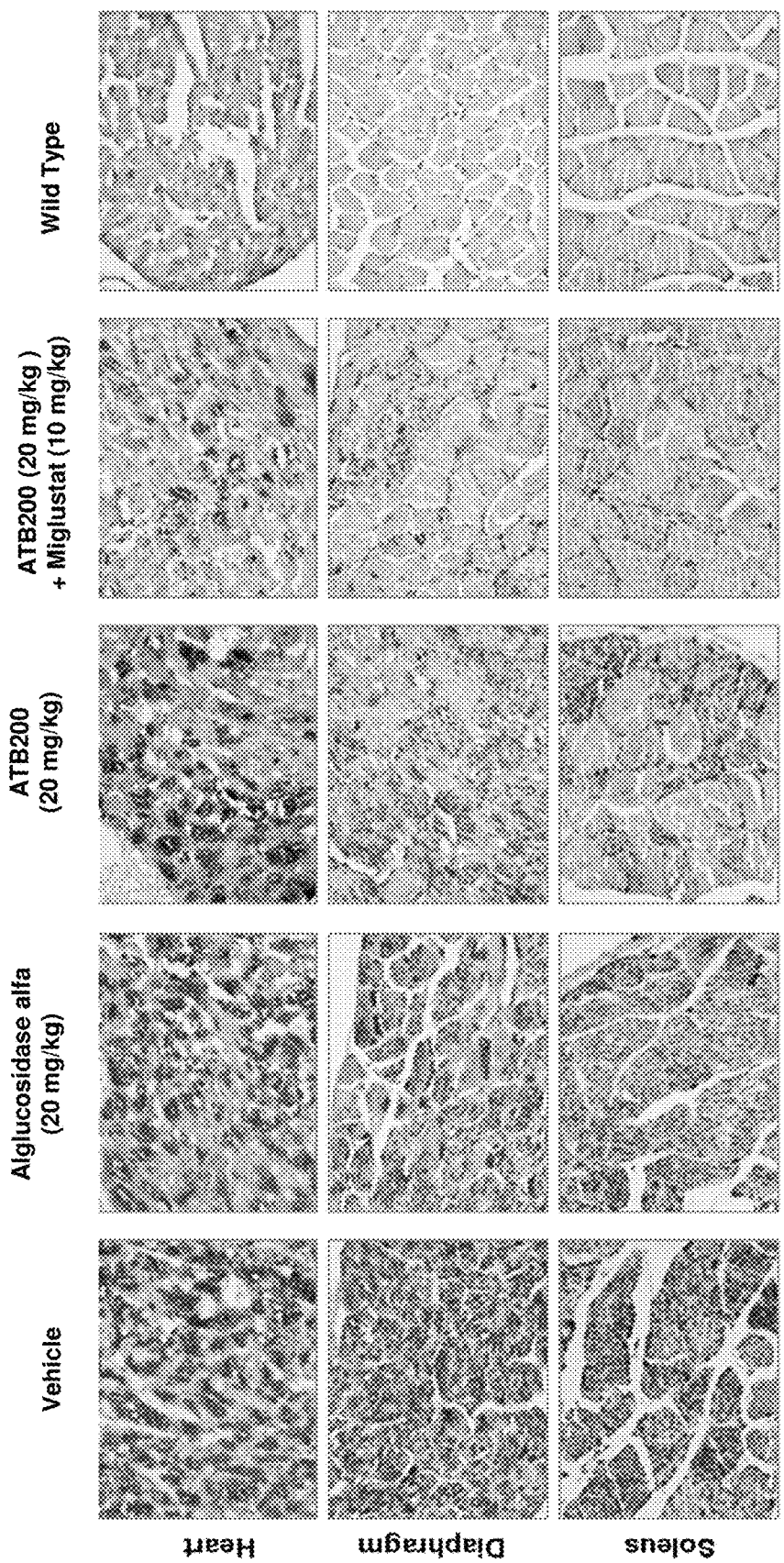
FIG. 16 is a series of electron micrographs of heart, diaphragm and soleus muscle from wild-type and Gaa-knockout mice treated with vehicle, alglucosidase alfa and ATB200 in the presence and absence of miglustat, showing levels of lysosome associated membrane protein (LAMP-1).

As seen in FIG. 16, administration of ATB200 showed a reduction in lysosome proliferation in heart, diaphragm and skeletal muscle (soleus) tissue compared to conventional treatment with alglucosidase alfa, and co-administration of miglustat with ATB200 showed a significant further reduction in lysosomal proliferation, approaching the levels seen in wild type (WT) mice. In addition, as seen in FIG. 17, administration of ATB200 showed a reduction in punctate glycogen levels in heart and skeletal muscle (soleus) tissue compared to conventional treatment with alglucosidase alfa, and co-administration of miglustat with ATB200 showed a significant further reduction, again approaching the levels seen in wild type (WT) mice.

Figures 17, 18:
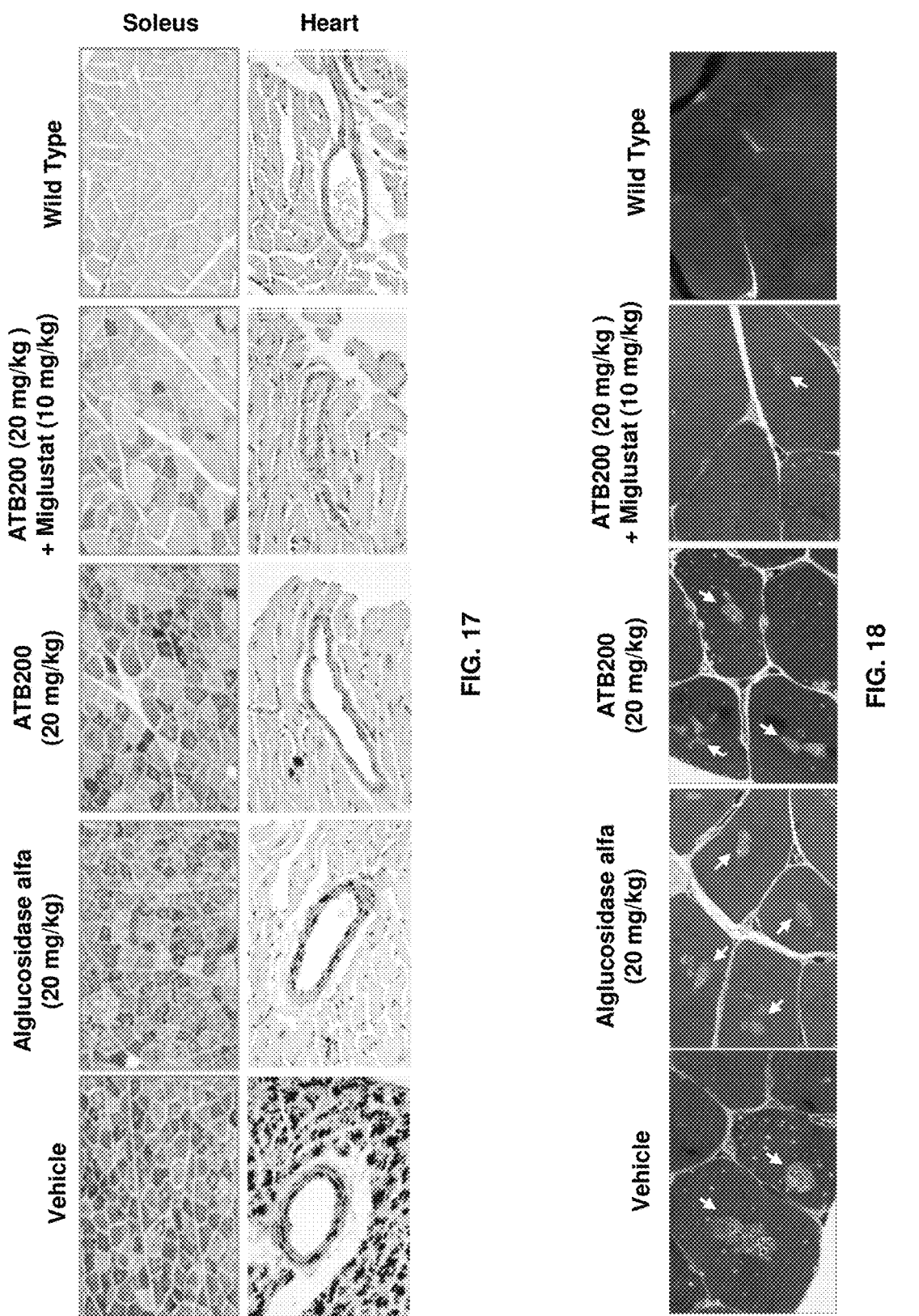
FIG. 17 is a series of electron micrographs of heart and soleus muscle from wild-type and Gaa-knockout mice treated with vehicle, alglucosidase alfa and ATB200 in the presence and absence of miglustat, showing glycogen levels by staining with periodic acid—Schiff reagent (PAS).
FIG. 18 is a series of electron micrographs (1000×) of quadriceps muscle from wild-type and Gaa-knockout mice treated with vehicle, alglucosidase alfa and ATB200 in the presence and absence of miglustat, stained with methylene blue to show vacuoles (indicated by arrows).
Figure 19:
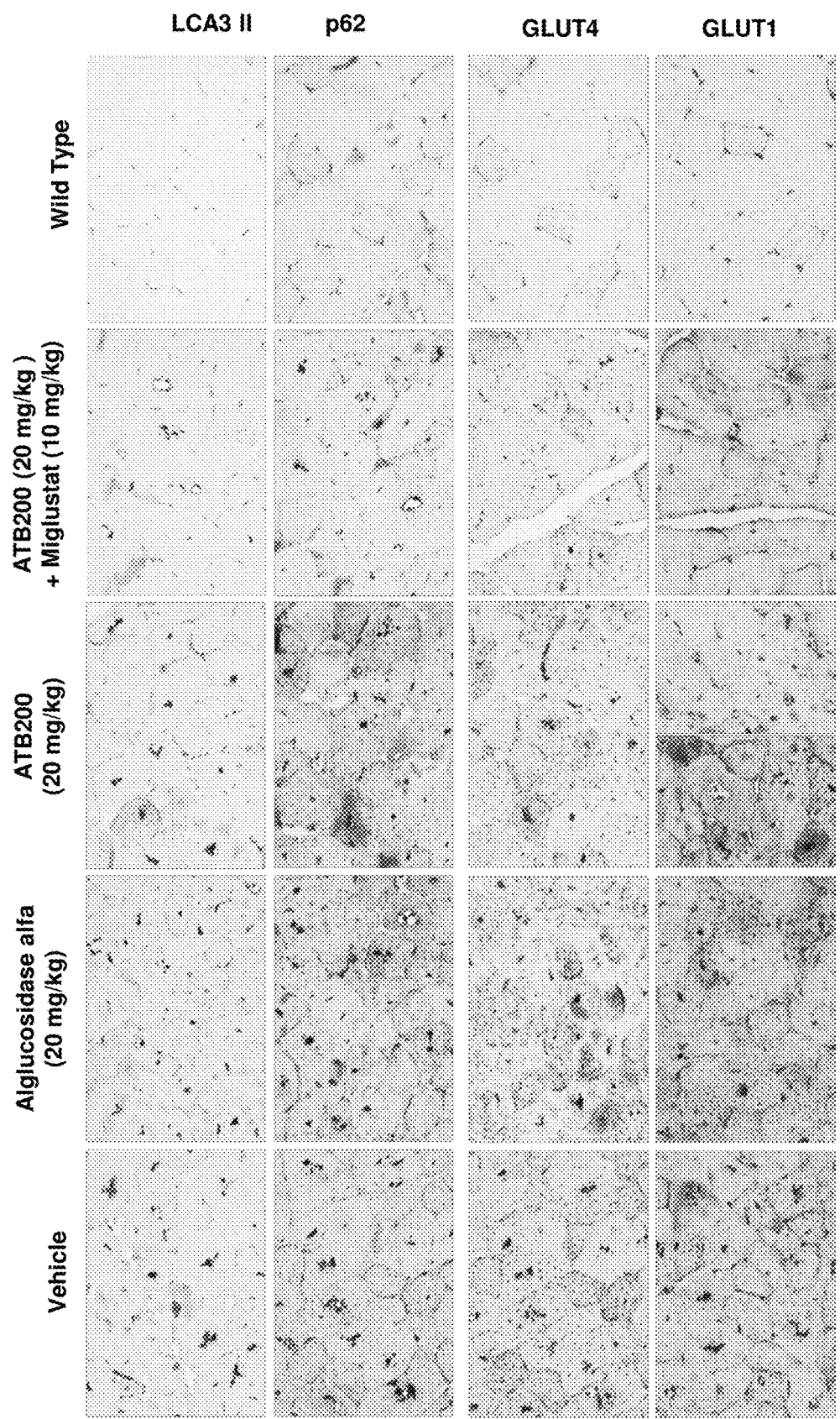
FIG. 19 is a series of electron micrographs (40×) of quadriceps muscle from wild-type and Gaa-knockout mice treated with vehicle, alglucosidase alfa and ATB200 in the presence and absence of miglustat, showing levels of the autophagy markers microtubule-associated protein 1A/1B-light chain 3 phosphatidylethanolamine conjugate (LC3A II) and p62, the insulin-dependent glucose transporter GLUT4 and the insulin-independent glucose transporter GLUT1.

As well, as seen in FIG. 18, co-administration of miglustat with ATB200 significantly reduced the number of vacuoles in muscle fiber in the quadriceps of Gaa knockout mice compared to untreated mice and mice treated with alglucosidase alfa. As seen in FIG. 19, levels of both LC3 II and p62 are increased in Gaa knockout mice compared to wild type mice, but are reduced significantly upon treatment with ATB200 and miglustat, indicating that the increase in autophagy associated with acid α-glucosidase deficiency is reduced upon co-administration of ATB200 and miglustat. In addition, levels of the insulin-dependent glucose transporter GLUT4 and the insulin-independent glucose transporter GLUT1 are increased in Gaa knockout mice compared to wild type mice, but again, are reduced significantly upon treatment with ATB200 and miglustat. The elevated GLUT4 and GLUT1 levels associated with acid α-glucosidase deficiency can contribute to increased glucose uptake into muscle fibers and increased glycogen synthesis both basally and after food intake. Thus, combination treatment with ATB200 and miglustat has been found to improve skeletal muscle morphology and physiology in a mouse model of Pompe disease.

Example 10: Muscle Function in Gaa-Knockout Mice

Figure 21A:
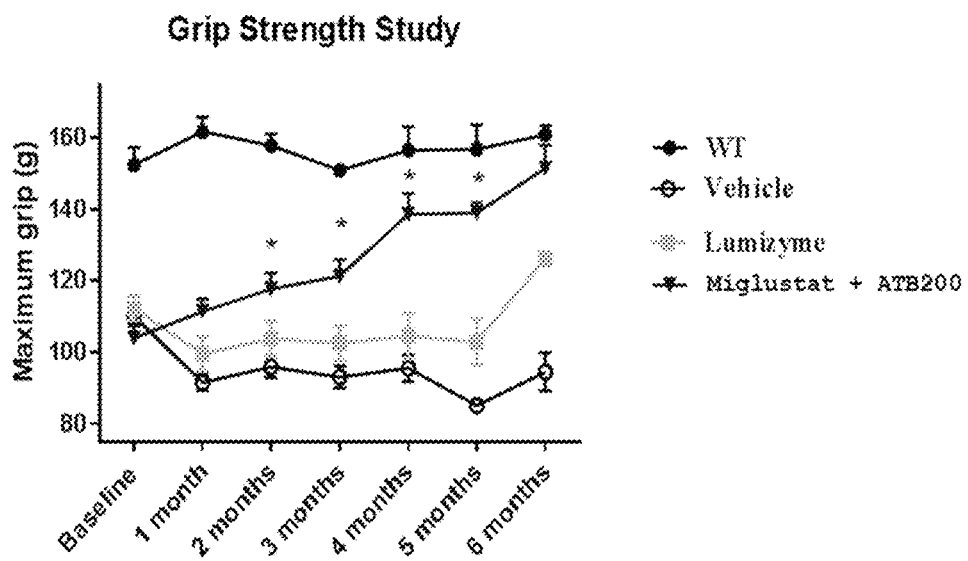
FIGS. 21A and 21B are graphs showing wire hand and grip strength muscle data for wild-type and Gaa-knockout mice treated with vehicle, alglucosidase alfa and ATB200 in the presence of miglustat.
Figure 21B:
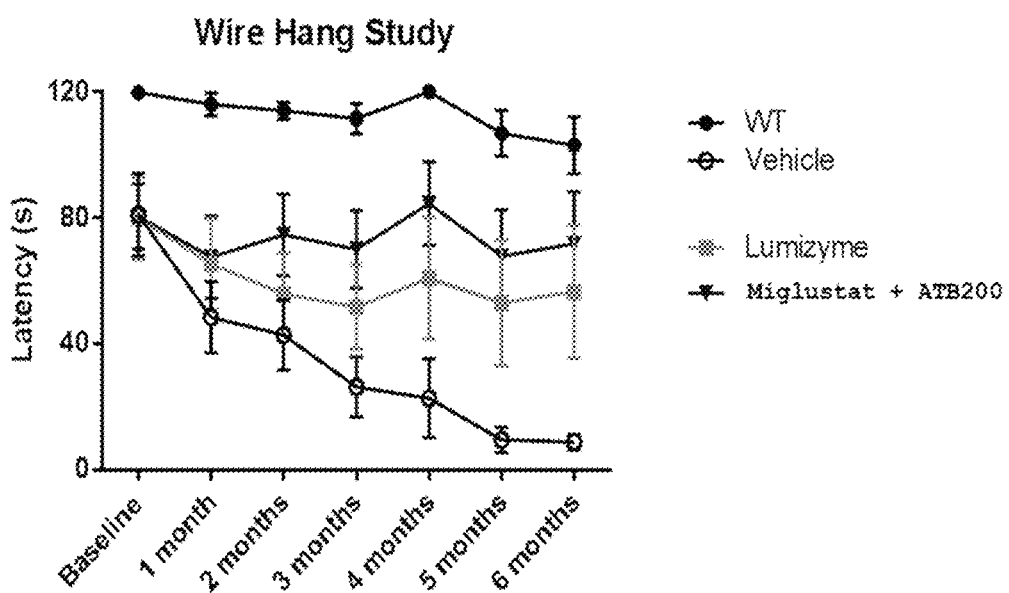
Figure 22A:
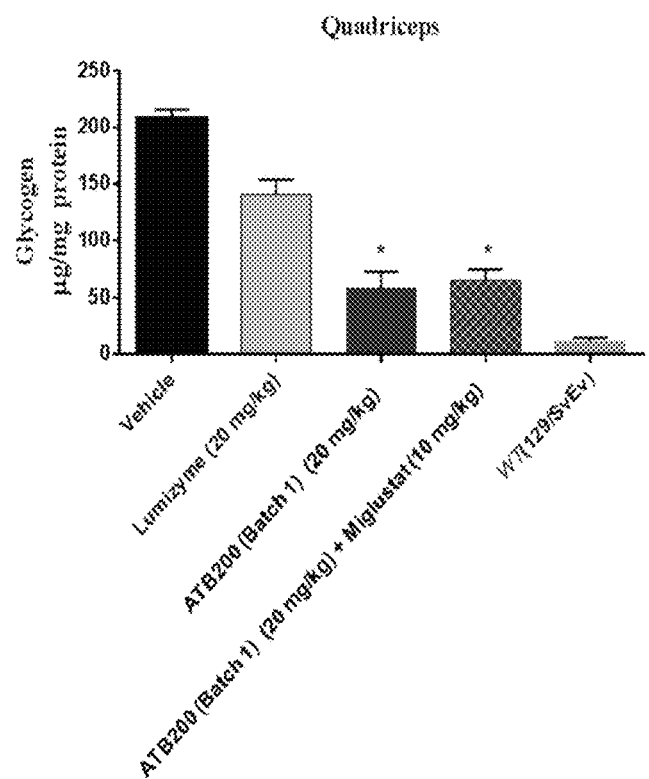
FIGS. 22A-22G are graphs showing glycogen levels in quadriceps, triceps and heart cells from wild-type and Gaa-knockout mice treated with vehicle, alglucosidase alfa and ATB200 in the presence and absence of miglustat.
Figure 22B:
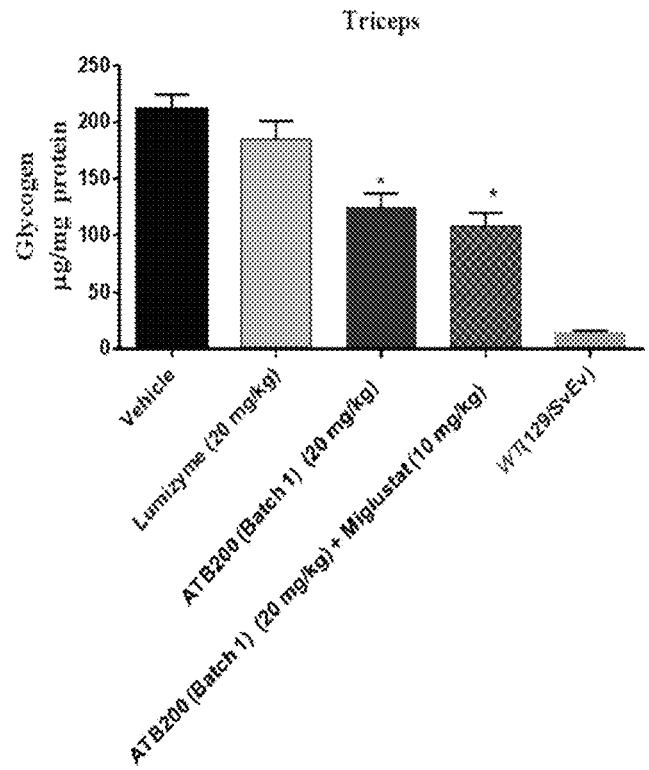
Figure 22C:
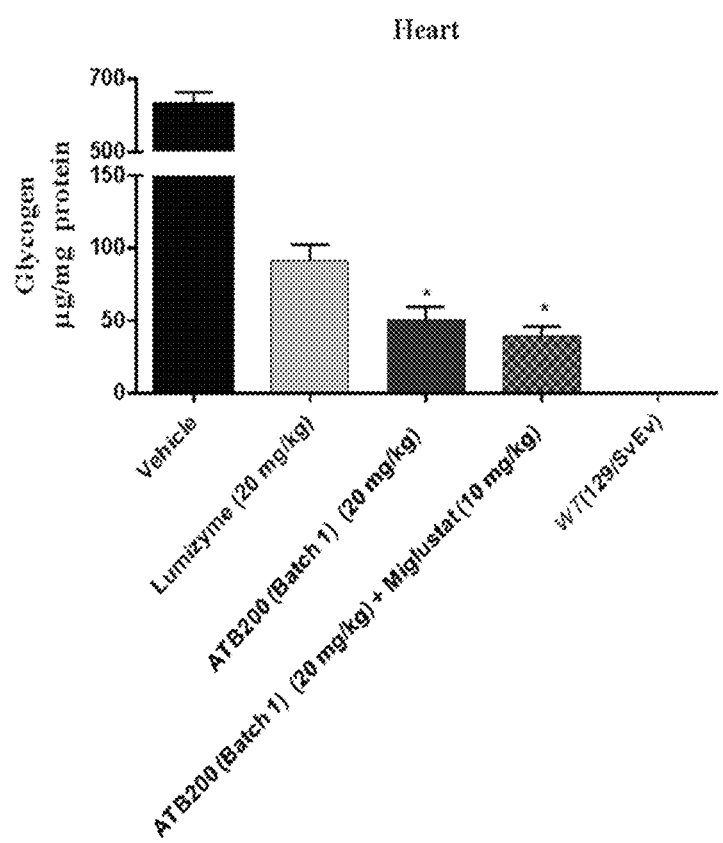
Figure 22D:
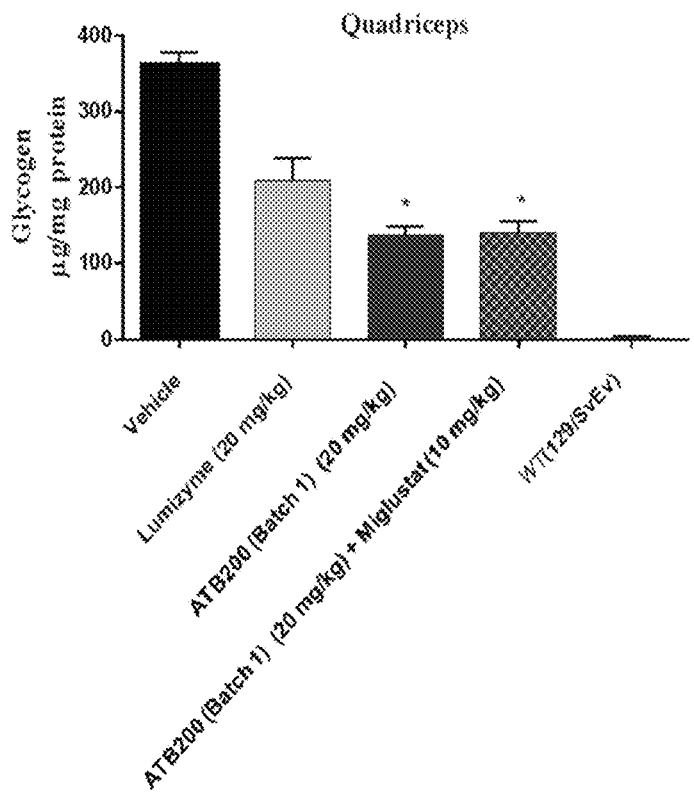
Figure 22E:
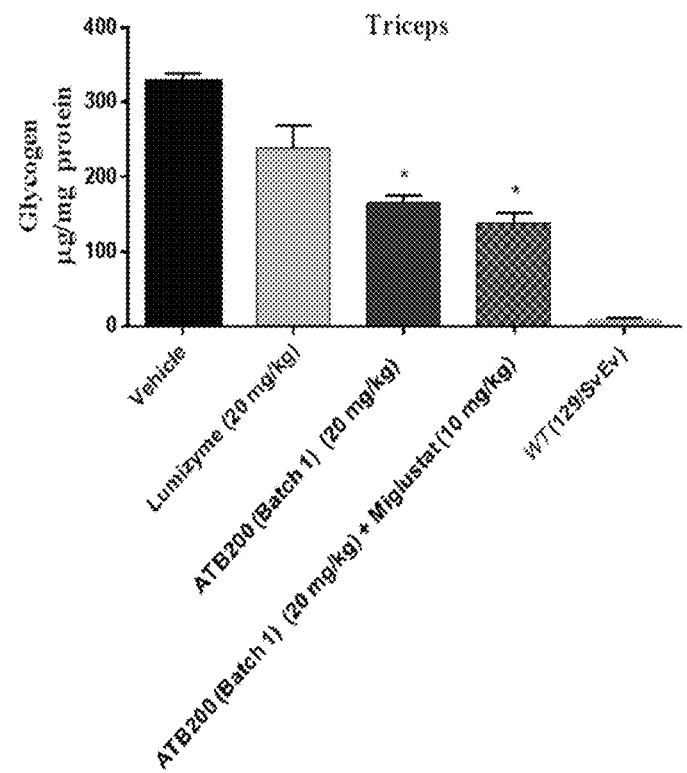
Figure 22F:
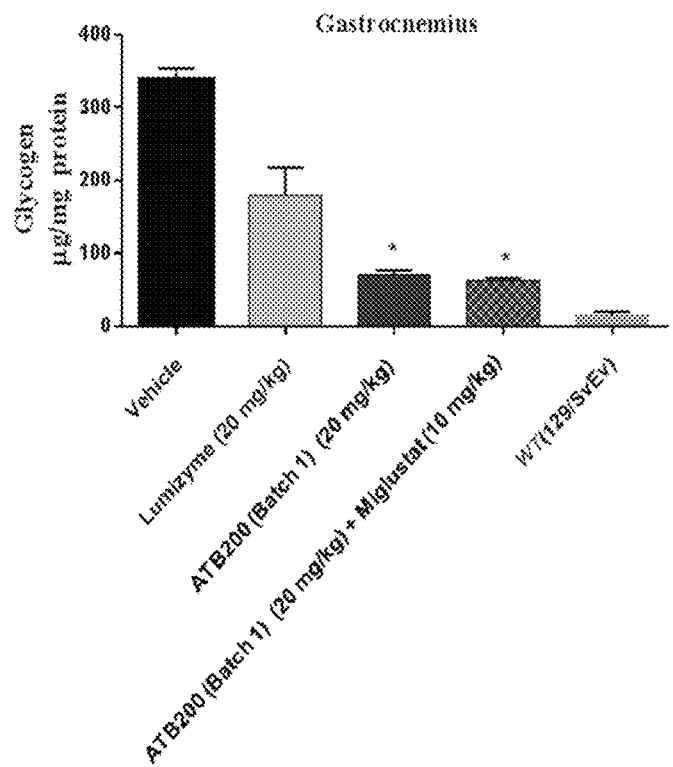
Figure 22G:
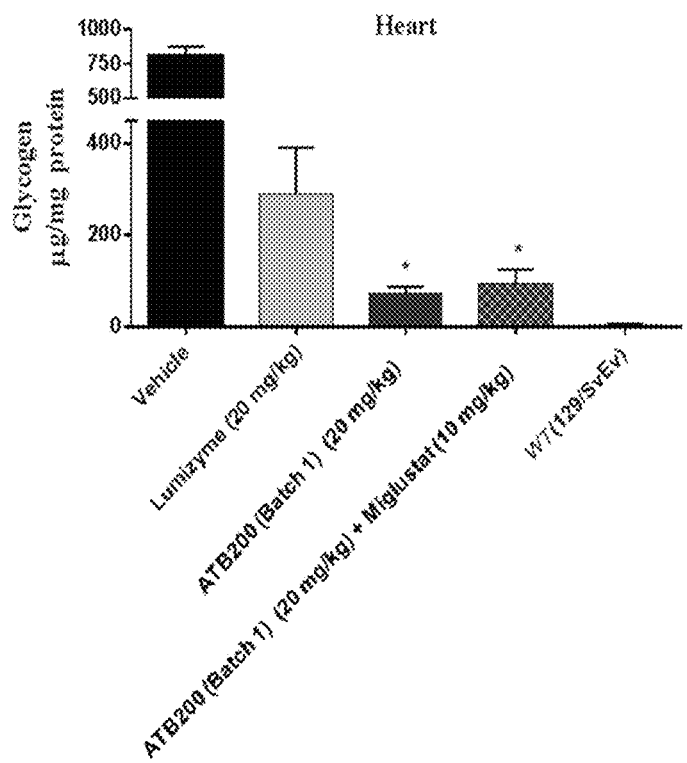

In longer-term studies of 12 biweekly administrations, 20 mg/kg ATB200 plus 10 mg/kg miglustat progressively increased functional muscle strength in Gaa KO mice from baseline as measured by both grip strength and wire hang tests (FIGS. 21A-21B). Alglucosidase alfa (Lumizyme®)-treated mice receiving the same ERT dose (20 mg/kg) were observed to decline under identical conditions throughout most of the study (FIGS. 21A-21B). As with the shorter-term study, ATB200/miglustat had substantially better glycogen clearance after 3 months (FIGS. 22A-22C) and 6 months (FIGS. 22D-22G) of treatment than alglucosidase alfa. ATB200/miglustat also reduced autophagy and intracellular accumulation of LAMP1 and dysferlin after 3 months of treatment (FIG. 23) compared to alglucosidase alfa. In FIG. 21A, * indicates statistically significant compared to Lumizyme® alone (p<0.05, 2-sided t-test). In FIGS. 22A-22G, * indicates statistically significant compared to Lumizyme® alone (p<0.05, multiple comparison using Dunnett's method under one-way ANOVA analysis).

Taken together, these data indicate that ATB200/miglustat was efficiently targeted to muscles to reverse cellular dysfunction and improve muscle function. Importantly, the apparent improvements in muscle architecture and reduced autophagy and intracellular accumulation of LAMP1 and dysferlin may be good surrogates for improved muscle physiology that correlate with improvements in functional muscle strength. These results suggest that monitoring autophagy and these key muscle proteins may be a rational, practical method to assess the effectiveness therapeutic treatments for Pompe disease in Gaa KO mice that may prove to be useful biomarkers from muscle biopsies in clinical studies.

Figure 23:
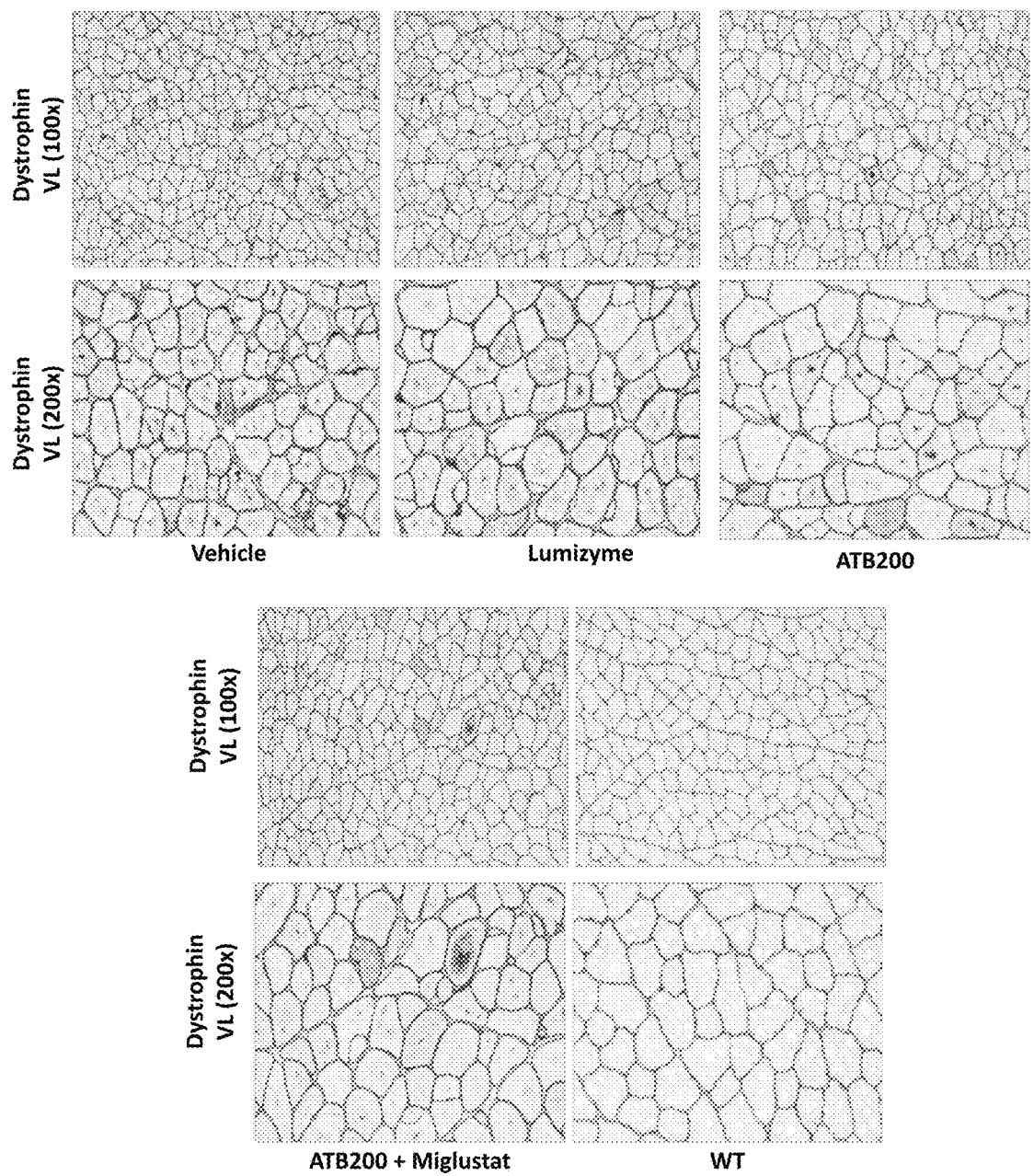
FIG. 23 is a series of photomicrographs (100× and 200×) of muscle fibers of vastus lateralis (VL) from wild-type and Gaa-knockout mice treated with vehicle, alglucosidase alfa and ATB200 in the presence and absence of miglustat, showing dystrophin signals.

FIG. 23 shows that 6 months of ATB200 administration with or without miglustat lowered intracellular accumulation of dystrophin in Gaa KO mice. There was a greater reduction for dystrophin accumulation for ATB200±miglustat than with Lumizyme®.

Example 11: Capturing of rhα-Gal A

The CIMPR binding profile of recombinant human α-galactosidase A (rhα-Gal A) in spent cell culture medium was measured before product capture using AEX chromatography (FIG. 20A) and after product capture using AEX chromatography (FIG. 20B). The dashed line in both graphs refers to the M6P elution gradient. Prior to AEX product capture, 80% of the rhα-Gal A is able to bind to the CIMPR. After AEX product capture, the total rhα-Gal A bound increases to 96%.

Example 12: Pharmacokinetic and Safety Data on Recombinant Acid α-Glucosidase ATB200 Co-Administered with Migluststat in ERT-Experienced and ERT-Naïve Patients with Pompe Disease This study was designed to primarily evaluate the safety, tolerability, and pharmacokinetics (PK) of ATB200 co-administered with miglustat. A PK/pharmacodynamic (PD) translational model from Gaa knockout mouse predicted that a combination of ATB200 20 mg/kg with a high dose (e.g. 260 mg) of miglustat in humans would provide optimal glycogen reduction.

In the description below, "high dose" of miglustat refers to a dose of about 260 mg and "low dose" of miglustat refers to a dose of about 130 mg.

The objective was to evaluate the preliminary total GAA protein, ATB200 and miglustat PK data, and safety markers from 10 patients in this of this phase 1/2 study.

Figure 24:
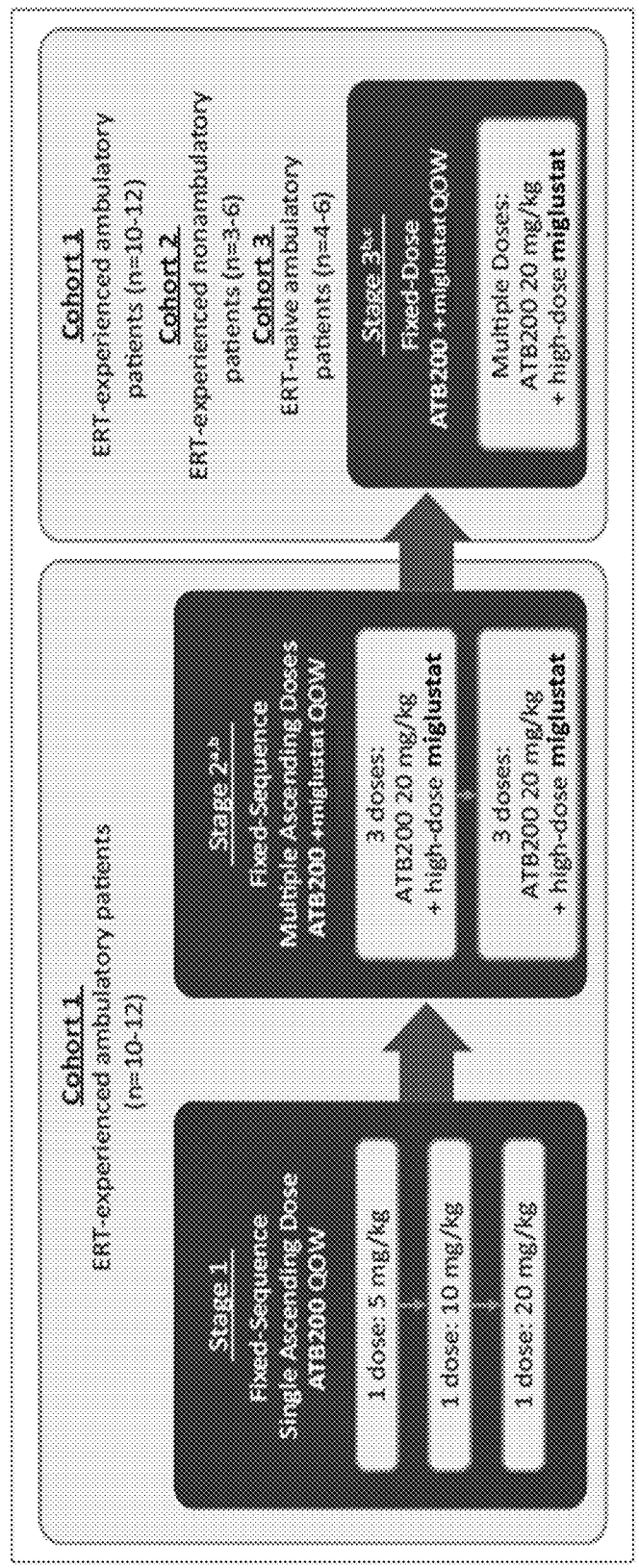
FIG. 24 shows the study design of an open-label, fixed-sequence, ascending-dose, first-in-human, phase 1/2 study to assess the safety, tolerability, PK, PD, and efficacy of intravenous infusions of ATB200 co-administered with oral miglustat in adults with Pompe disease.

This is an open-label, fixed-sequence, ascending-dose, first-in-human, phase 1/2 study to assess the safety, tolerability, PK, PD, and efficacy of intravenous infusions of ATB200 co-administered with oral miglustat in adults with Pompe disease (FIG. 24). Mean total GAA protein and miglustat PK results from the first 8 Cohort 1 patients through Visit 9 and the first 2 Cohort 3 patients were assessed.

[a]Safety data from 2 sentinel patients from Cohort 1 were reviewed at each dose level before dosing in Cohorts 2 and 3.

[b]During Stages 2 and 3, miglustat was orally administered prior to the start of ATB200 intravenous infusion. For all doses, ATB200 was intravenously infused for a 4-hour duration.

[c]The first 2 patients in Cohorts 2 and 3 served as sentinel patients for their respective cohorts.

Key Inclusion Criteria:
  Males and females aged 18-65 years who were diagnosed with Pompe disease based on documented deficiency of GAA enzyme activity or by GAA genotyping
  Received ERT with alglucosidase alfa for 2-6 years (or ≥2 years for Cohort 2) prior to trial initiation (Cohort 1)
  Currently receiving alglucosidase alfa at a frequency of every other week and completed the last 2 infusions without a drug-related adverse event resulting in dose interruption (Cohorts 1 and 2)
  Must be able to walk between 200 and 500 meters on the 6-Minute Walk Test (Cohorts 1 and 3)
  Upright forced vital capacity must be 30%-80% of predicted normal value (Cohorts 1 and 3)
  Must be wheelchair-bound and unable to walk unassisted (Cohort 2)

PK Analysis:
  Blood samples for plasma total GAA protein and activity concentration were collected
    Stage 1: prior to start of ATB200 infusion and 1, 2, 3, 3.5, 4, 4.5, 5, 6, 8, 10, 12, and 24 hour(s) post-start of infusion
    Stages 2 and 3: 1, 2, 3, 4, 4.5, 5, 6, 7, 9, 11, 13, and 25 hour(s) post-miglstat oral administration Blood samples for plasma miglustat concentrations were taken just prior to miglustat oral administration (time 0) and 1, 1.5, 2, 2.5, 3, 4, 5, 6, 9, 11, and 25 hour(s) after miglustat oral administration. Plasma miglustat is determined by a validated LC-MS/MS assay Total GAA protein concentrations in plasma for ATB200 5, 10, and 20 mg/kg were determined by a validated LC-MS/MS quantification of rhGAA-specific "signature" peptide(s)

A preliminary analysis was completed in 8 patients in Cohort 1 who completed Stages 1 and 2 and 2 patients in Cohort 3 who started Stage 3

Initial ERT-switch patients are representative of the Pompe disease population, with mean 5.02 years on ERT (Table 6)

TABLE 6

Baseline Characteristics

| Baseline Characteristics (N = 12[a]) | ERT-Experienced Ambulatory (n = 10) | Naïve (n = 2) |
|---|---|---|
| Time on ERT (Lumizyme ®/Myozyme ®), years, mean (STDV) | 5.02 (1.2) | N/A |
| Age, years, mean (range) | 47.7 (8.19) | 33.0 (12.73) |
| Sex, M/F, % | 80/20 | 0/100 |
| 6 MWT, meters, mean (STDV) | 398.4 (95.92) | 432.1 (67.81) |
| Upright FVC, mean %, predicted (STDV) | 51.9 (13.84) | 51.0 (26.87) |

6 MWT = 6-minute walk test; FVC = forced vital capacity; N/A = not available; STDV = standard deviation.
[a] n = 10 from Cohort 1 (ambulatory ERT-switch) through interim data analysis; n = 2 from Cohort 3 (naive).

Total GAA Protein

Figure 25A:
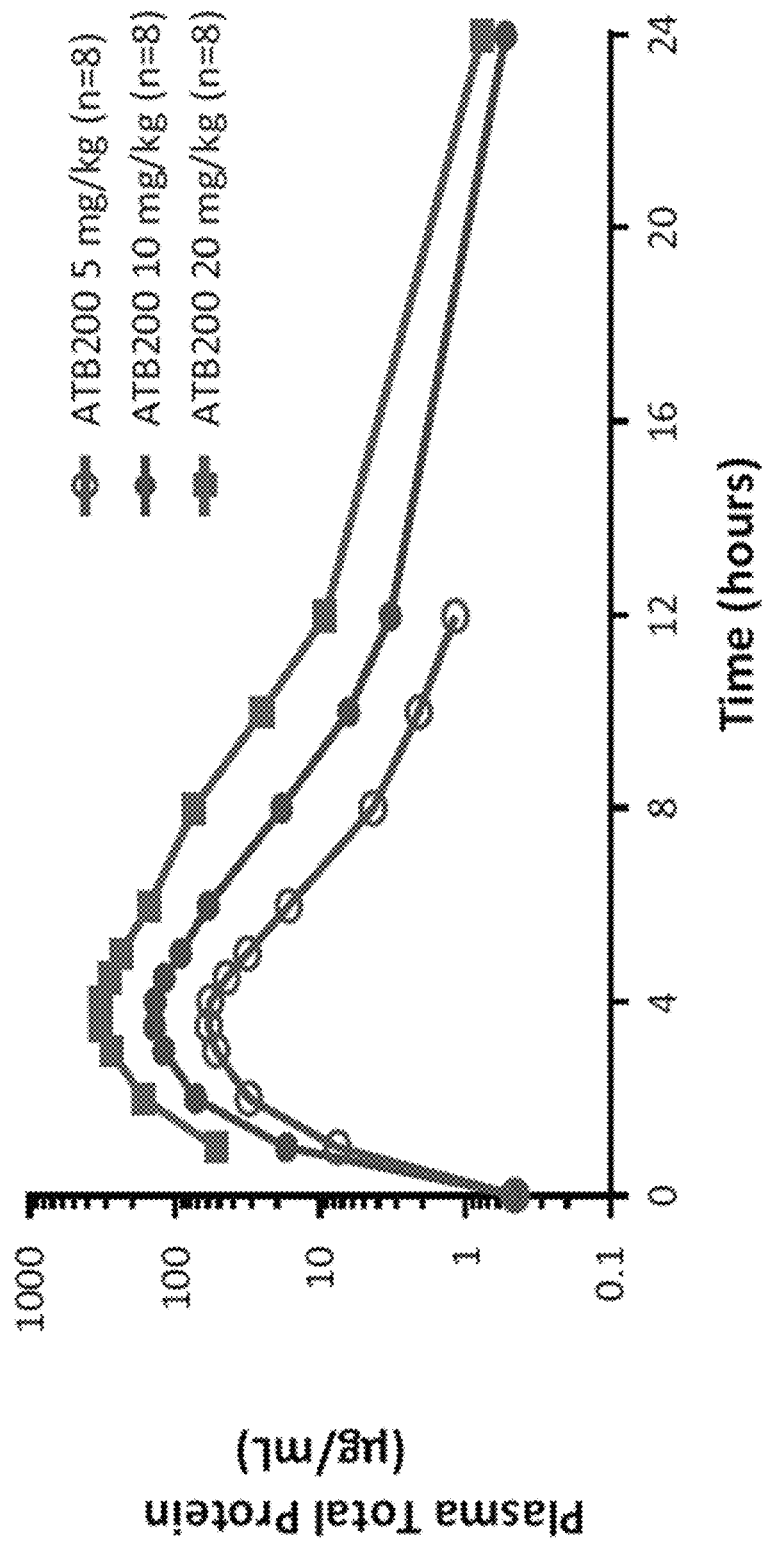
FIGS. 25A-25B are graphs showing the concentration-time profiles of GAA total protein in plasma in human subjects after dosing of 5, 10 or 20 mg/kg ATB200, 20 mg/kg ATB200 and 130 mg miglustat, or 20 mg/kg ATB200 and 260 mg miglustat.
Figure 25B:
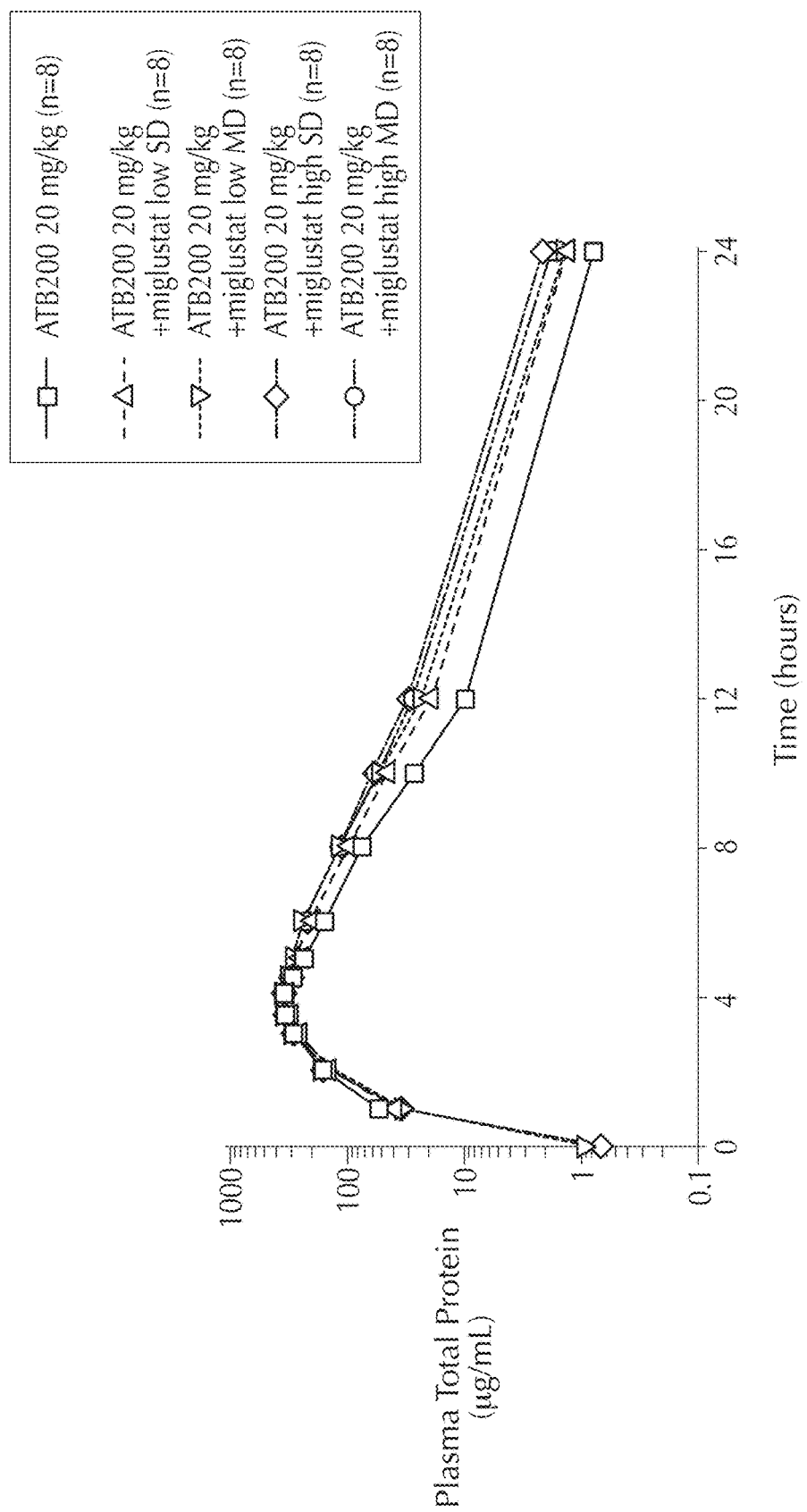
Figure 25C:
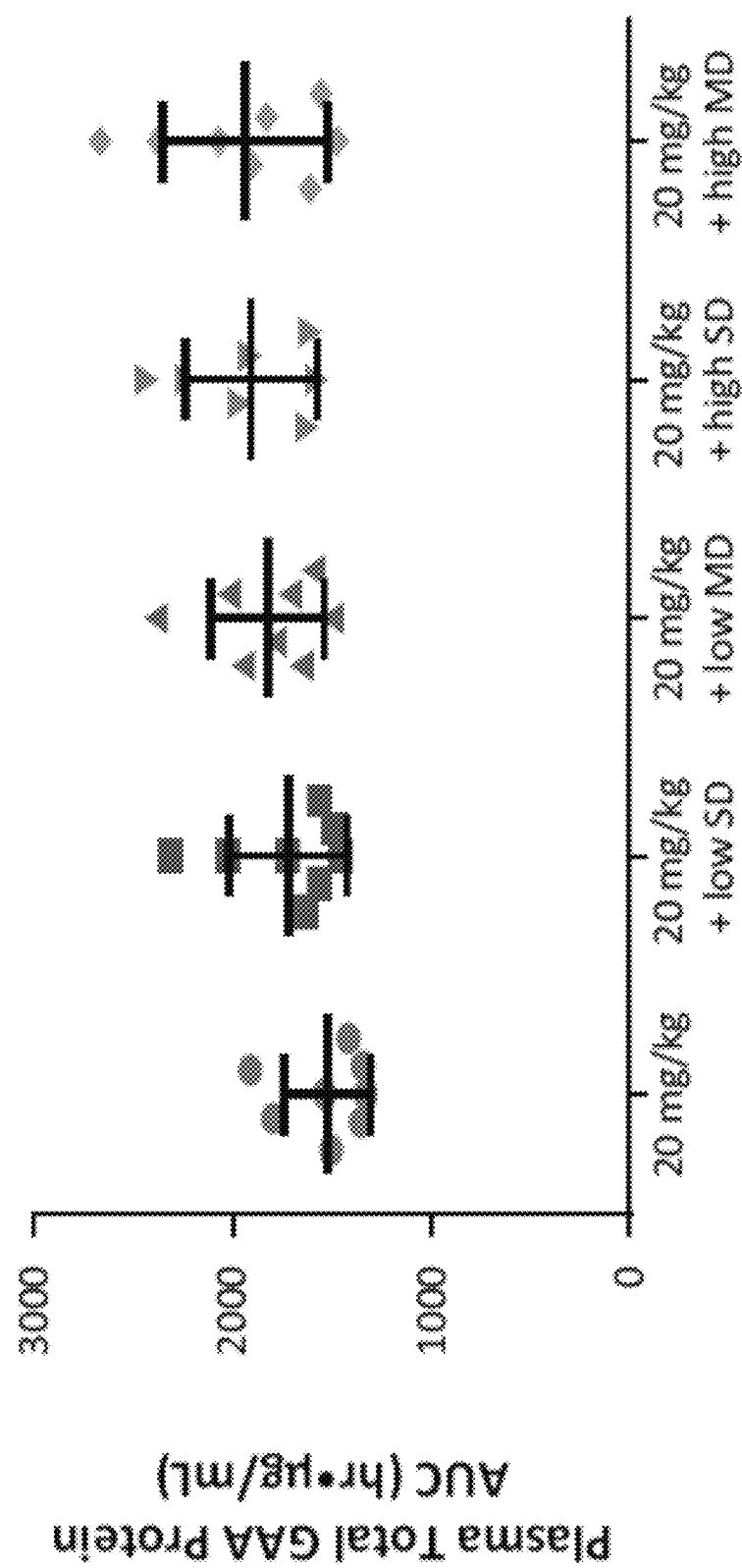
FIG. 25C is a graph showing the AUC of GAA total protein in plasma in human subjects after dosing of 20 mg/kg ATB200, 20 mg/kg ATB200 and 130 mg miglustat, or 20 mg/kg ATB200 and 260 mg miglustat.
Figure 25D:
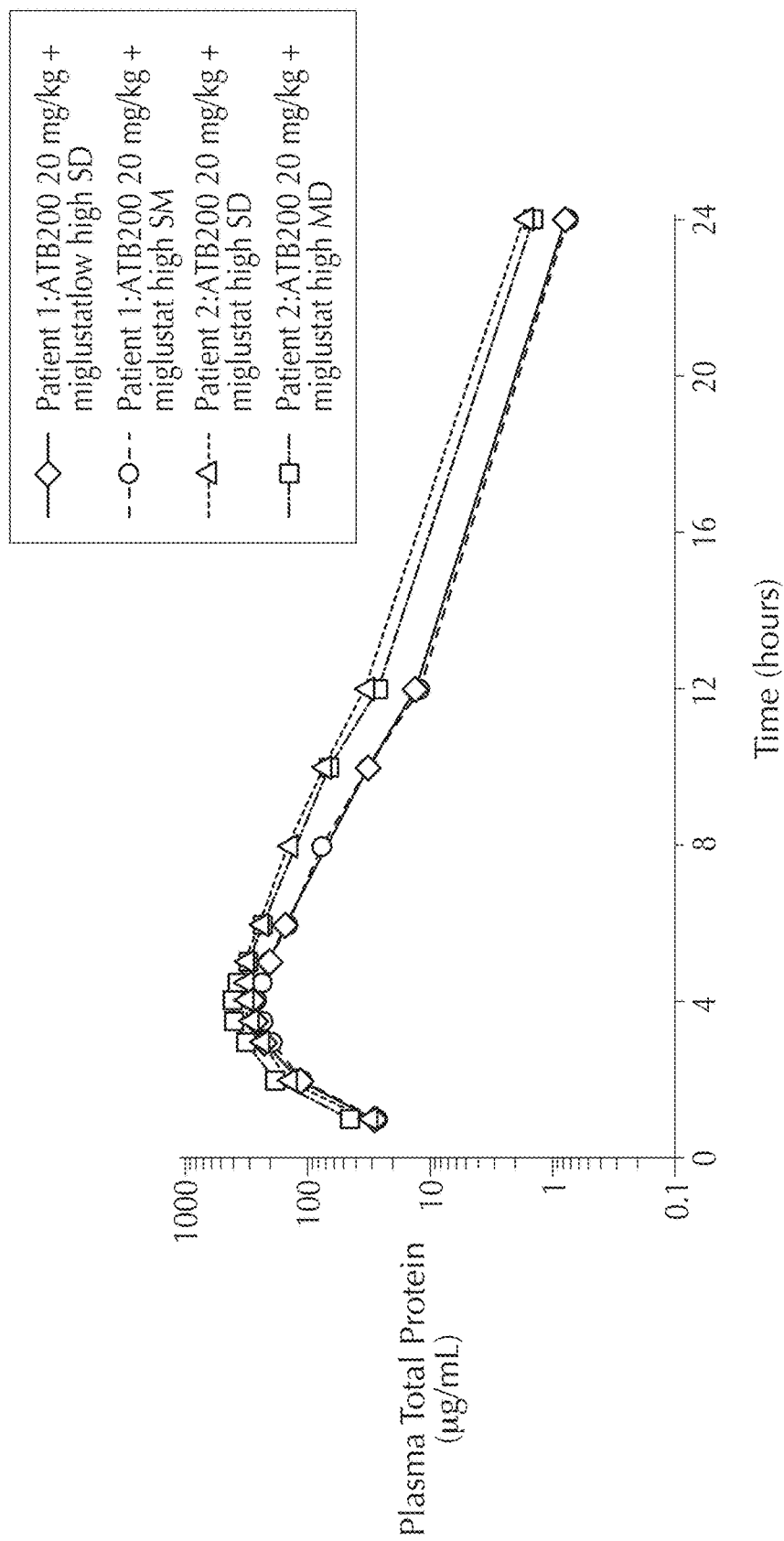
FIG. 25D is a graph showing the concentration-time profiles of GAA total protein in plasma in two individual human subjects after dosing of 20 mg/kg ATB200 and 260 mg miglustat.

When given alone, ATB200 increases in a slightly greater-than-dose-proportional manner (Table 7 and FIGS. 25A-25D). Variability appears to increase with miglustat dose (FIG. 25C). Co-administration of ATB200 20 mg/kg with the high dose of miglustat (260 mg) increased total GAA protein exposure (AUC) by approximately 25% relative to ATB200 alone at 20 mg/kg. The distribution half-life (α-phase) increased by 45%, suggesting that the high dose of miglustat stabilizes ATB200 in plasma. An increase in the distribution half-life is accompanied by an increase in AUC from time to maximum plasma concentration to approximately 12 hours post-dose. The increases in AUC and half-life can be observed on the log scale, during the terminal elimination phase (FIG. 25B). ATB200 demonstrated a relatively high volume of distribution. The disposition of plasma total GAA protein appears similar between ERT-naive (Cohort 3) and ERT-experienced patients (Cohort 1) (FIGS. 25A and 25D).

TABLE 7

Total GAA Protein

| Cohort | Treatment | $C_{max}$ (ng/mL)[a] | $t_{max}$ (hr)[b] | $AUC_{0-t}$ (ng * hr/mL)[a] | $AUC_{0-\infty}$ (ng * hr/mL)[a] | $\beta t_{1/2}$ (hr)[c] | $\alpha t_{1/2}$ (hr)[c] | $CL_T$ (L/hr)[c] | $V_{ss}$ (L)[c] |
|---|---|---|---|---|---|---|---|---|---|
| 1 | 5 mg/kg alone[d] | 61 (18.1) | 3.8 (3.0-4.0) | 215 (16.7) | 218 (16.4) | 1.9 (16.7) | 1.1 (10.2) | 2.1 (16.9) | 4.62 (12.7) |
| 1 | 10 mg/kg alone[d] | 144 (16.6) | 4.0 (3.5-4.0) | 578 (20.3) | 584 (20.4) | 1.6 (46.1) | 1.3 (10.5) | 1.59 (25.4) | 3.87 (16.5) |
| 1 | 20 mg/kg alone[d] | 345 (10.1) | 4.0 (3.5-4.0) | 1508 (14.5) | 1512 (14.4) | 2.1 (29.7) | 1.5 (6.5) | 1.22 (21.7) | 3.52 (12.4) |
| 1 | ATB200 20 mg/kg + miglustat low SD[d] | 334 (16.2) | 4.0 (3.5-4.0) | 1694 (17.7) | 1701 (17.5) | 2.4 (16.6) | 1.8 (10.2) | 1.09 (22.9) | 3.76 (13.3) |
| 1 | ATB200 20 mg/kg + miglustat low MD[d] | 353 (13.7) | 4.0 (3.5-5.0) | 1804 (15.7) | 1808 (15.8) | 2.5 (8.1) | 1.9 (21.8) | 1.02 (21.4) | 3.73 (12.3) |
| 1 | ATB200 20 mg/kg + miglustat high SD[e] | 349 (13.9) | 4.0 (3.5-4.0) | 1878 (17.5) | 1886 (17.5) | 2.7 (13.1) | 2.3 (18.9) | 0.98 (26.5) | 3.74 (12.3) |
| 1 | ATB200 20 mg/kg + miglustat high MD[d] | 356 (20.2) | 4.0 (3.5-4.0) | 1886 (21.3) | 1901 (21.7) | 2.5 (20.5) | 2.1 (16.1) | 0.98 (27.3) | 3.6 (18.7) |
| 3 | ATB200 20 mg/kg + miglustat high MD[f] | 291 (21.6) | 4.3 (4.0-4.5) | 1597 (34.8) | 1600 (34.9) | 2.4 (5.4) | 2 (14.5) | 0.69 (28.9) | 2.61 (17.3) |

TABLE 7-continued

| | | Total GAA Protein | | | | | | | |
|---|---|---|---|---|---|---|---|---|---|
| Cohort | Treatment | $C_{max}$ (ng/mL)[a] | $t_{max}$ (hr)[b] | $AUC_{0-t}$ (ng * hr/mL)[a] | $AUC_{0-\infty}$ (ng * hr/mL)[a] | $\beta t_{1/2}$ (hr)[c] | $\alpha t_{1/2}$ (hr)[c] | $CL_T$ (L/hr)[c] | $V_{ss}$ (L)[c] |
| 3 | ATB200 20 mg/kg + miglustat high MD[f] | 330 (27.5) | 4.0 (4.0-4.0) | 1672 (32.7) | 1676 (32.6) | 2.6 (8.7) | 1.9 (9.0) | 0.66 (26.6) | 2.33 (23.2) |

AUC = area under the curve;
$CL_T$ = total body clearance;
$C_{max}$ = maximum drug concentration;
CV = coefficient of variability;
MD = multiple doses;
SD = single dose;
$t_{1/2}$ = half-life;
tmax = time to maximum drug concentration;
$V_{ss}$ = apparent volume of distribution in steady state.
[a]Geometric mean (CV %).
[b]Median (min-max).
[c]Arithmetic mean (CV %.)
[d]n = 8.
[e]n = 7.
[f]n = 2.

Miglustat PK

Figure 26:
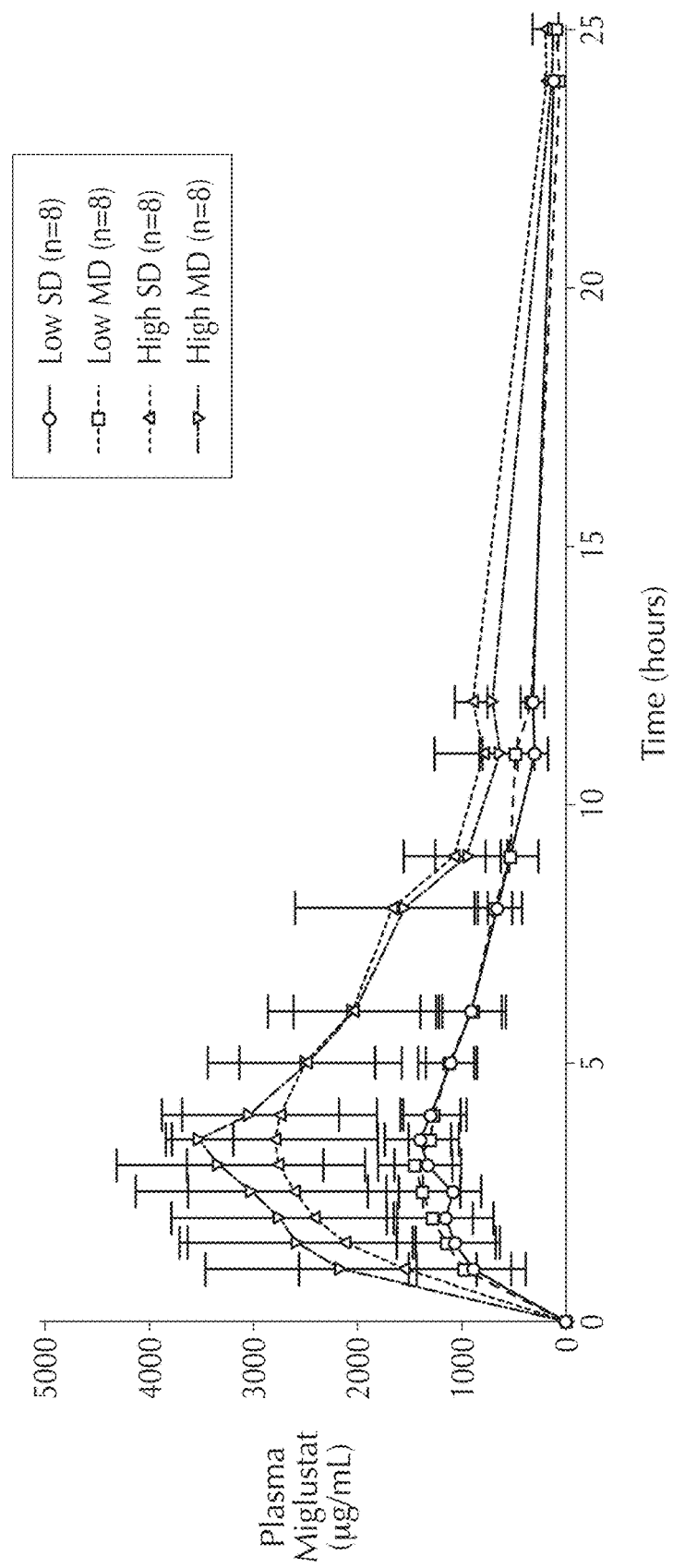
FIG. 26 is a graph showing the concentration-time profiles of miglustat in plasma in human subjects after dosing of 130 mg or 260 mg of miglustat.

Miglustat demonstrated dose-proportional kinetics (Table 8 and FIG. 26). Plasma miglustat appears similar between single and multiple doses.

TABLE 8

| | | | Miglustat PK Summary | | | | |
|---|---|---|---|---|---|---|---|
| Treatment | $C_{max}$ (ng/mL)[a] | $t_{max}$ (h)[b] | $AUC_{0-t}$ (ng * h/mL)[a] | $AUC_{0-\infty}$ (ng * h/mL)[a] | $t1_{/2}$ (h)[c] | CL/F (L/h)[c] | $V_z$/F (L)[c] |
| Low SD | 1486 (29.9) | 3.5 (1.5-3.5) | 11,807 (25.6) | 12,565 (26.8) | 5.6 (11.7) | 10.6 (23) | 85.8 (23.4) |
| Low MD | 1518 (27.6) | 3.0 (1.5-3.5) | 12,254 (26.4) | 13,094 (28.3) | 5.9 (32.1) | 10.2 (23.9) | 86.7 (43.9) |
| High SD | 3059 (36.1) | 3.5 (1.5-5) | 23,999 (35) | 25,859 (34.4) | 5.7 (29.9) | 10.6 (33) | 86.3 (45.7) |
| High MD | 3569 (25.5) | 3.0 (1.0-4.0) | 24,970 (24.1) | 25,972 (23) | 5.3 (15.6) | 10.3 (26.4) | 81 (41.8) |

$V_z$ = apparent volume of distribution in terminal state.
[a]Geometric mean (CV %).
[b]Median (min-max).
[c]Arithmetic mean (CV %).

Pharmacodynamics

Figure 27A:
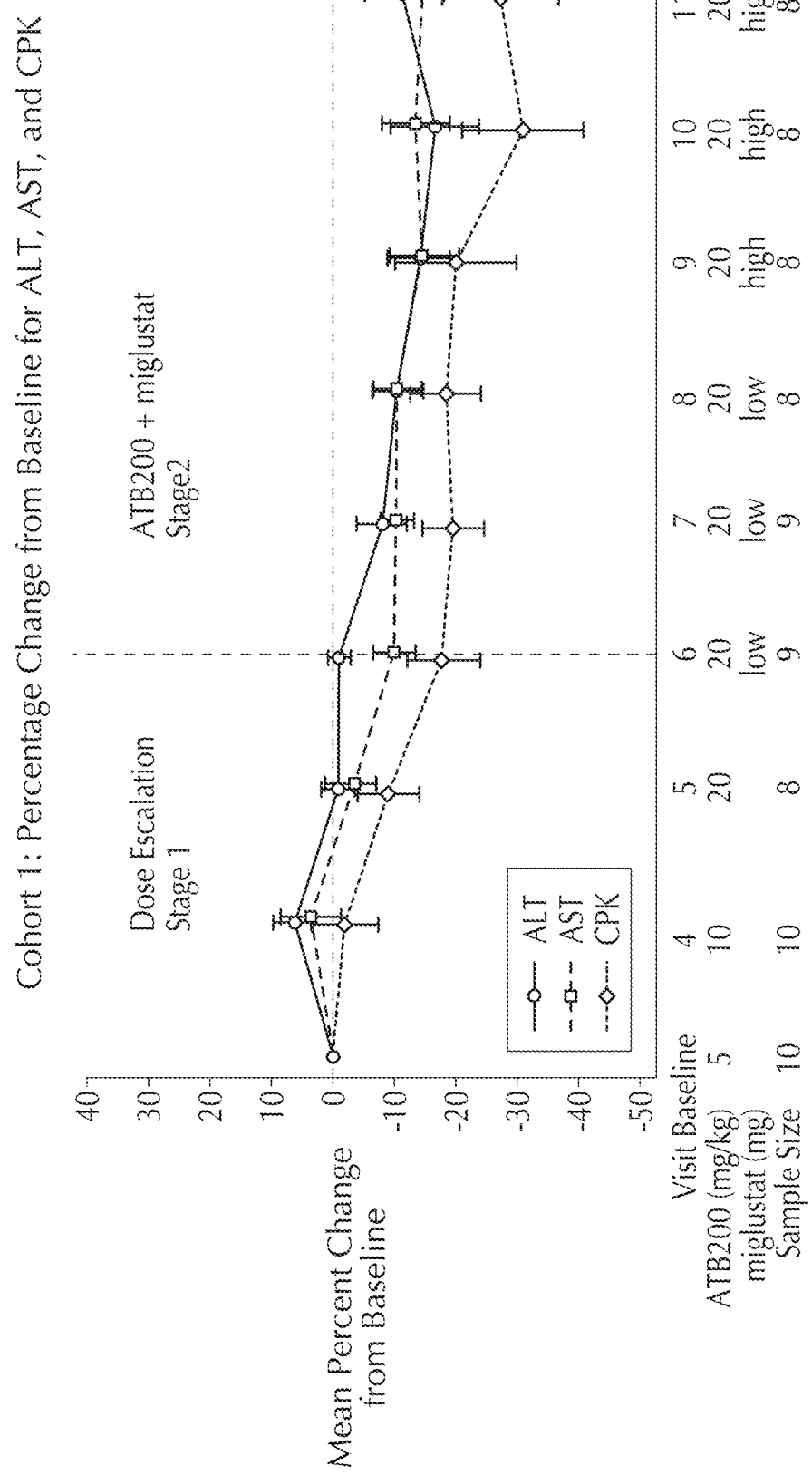
FIGS. 27A-27D are graphs showing changes in alanine aminotransferase (ALT), aspartate aminotransferase (AST), creatine phosphokinase (CPK) and hexose tetrasaccharide (Hex4) levels in human patients after administration of ascending doses of ATB200 (5, 10 and 20 mg/kg) followed by co-administration of ATB200 (20 mg/kg) and miglustat (130 and 260 mg).
Figure 27B:
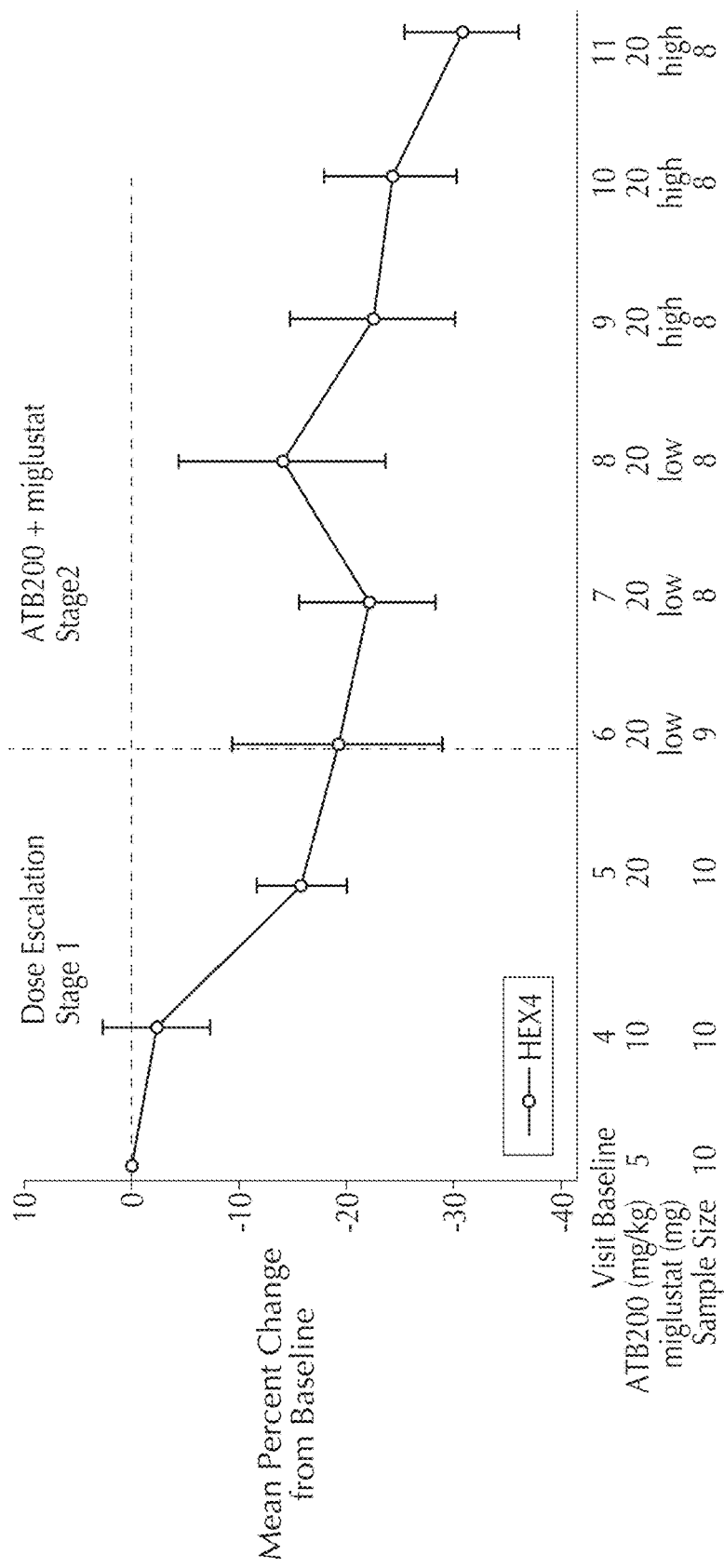
Figure 27C:
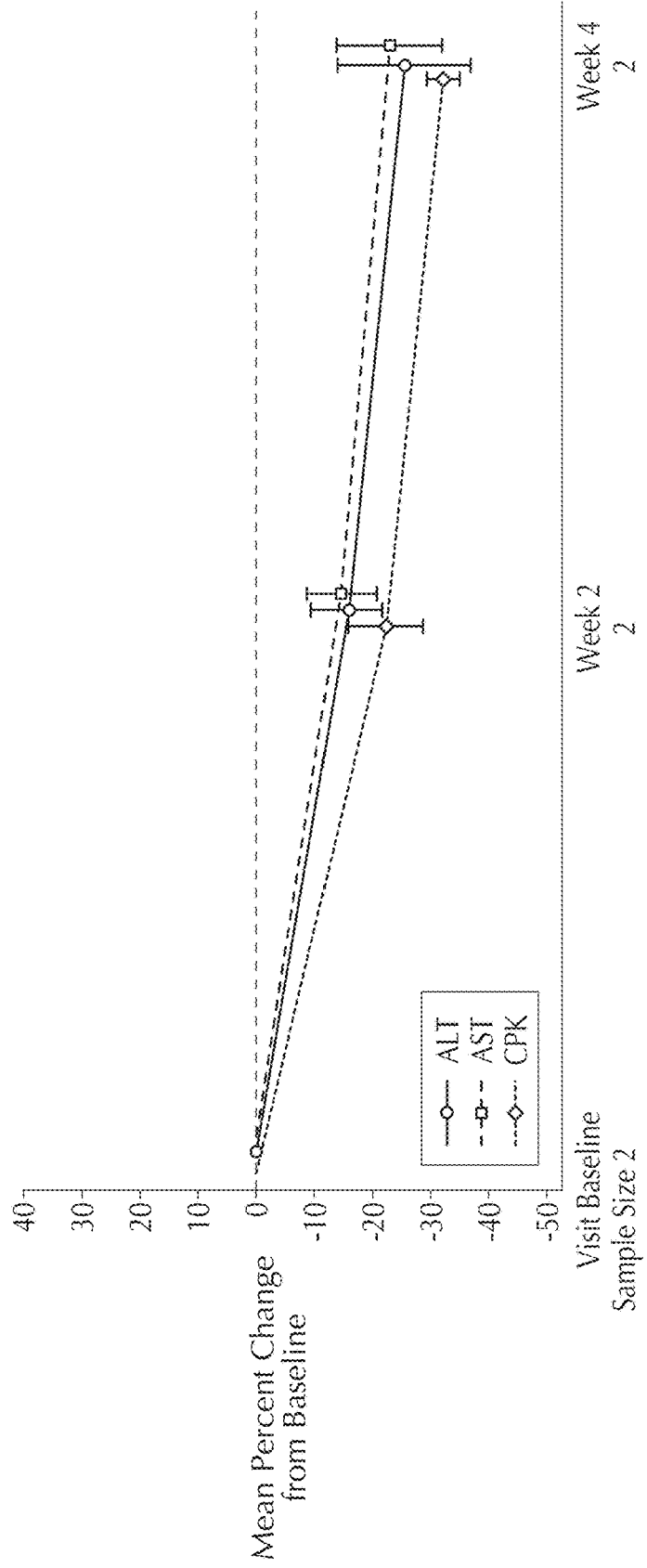
Figure 27D:
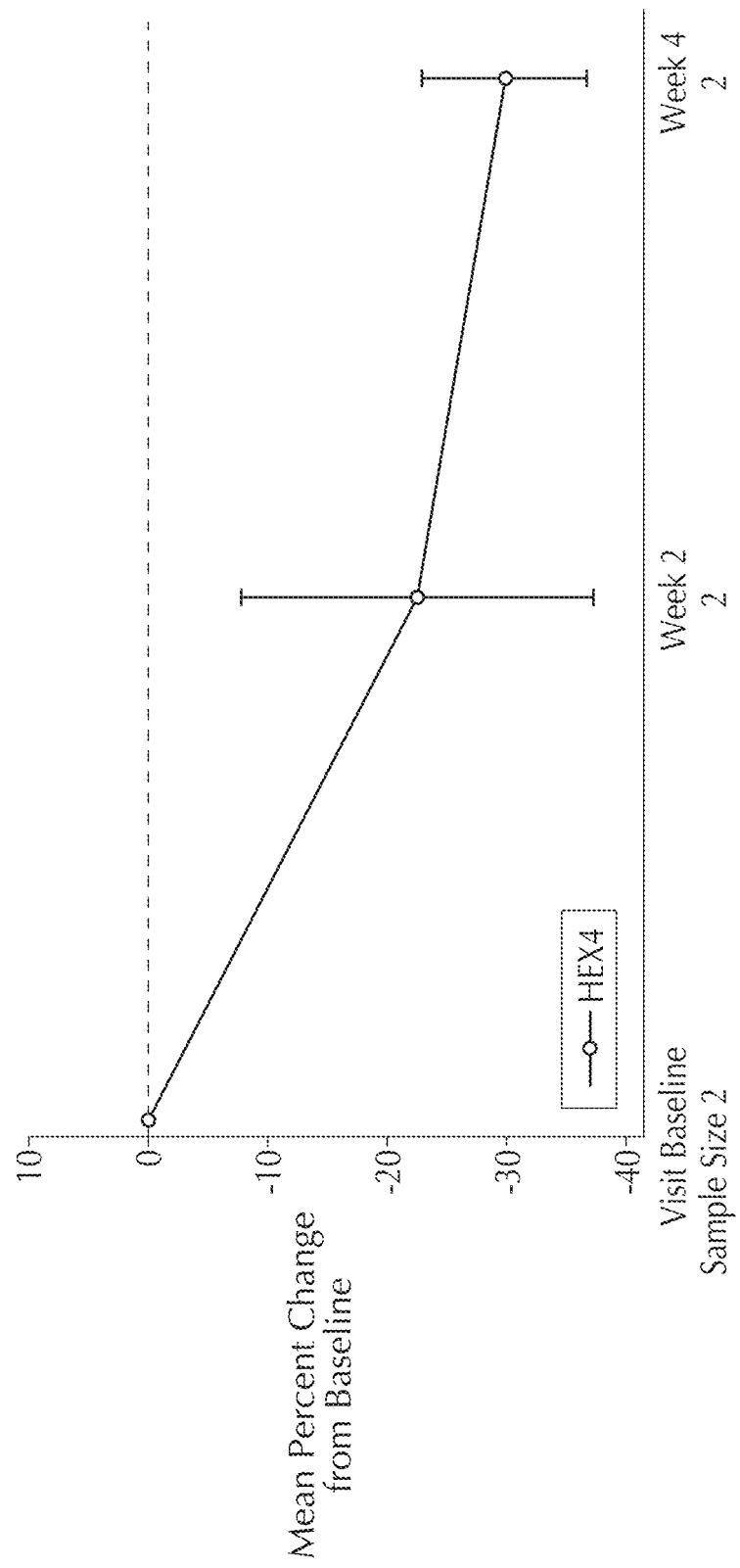

By the 11th visit in ERT-experienced patients from Cohort 1 (FIGS. 27A and 27B):
  Alanine aminotransferase (ALT) decreased in 5 of 8 patients; 4/4 patients with elevated baseline levels normalized
  Aspartate aminotransferase (AST) decreased in 6 of 8 patients; 3/4 patients with elevated baseline levels normalized
  Creatine phosphokinase (CPK) decreased in 6 of 8 patients; 2/6 patients with elevated baseline levels normalized
  Urine glucose tetrasaccharide (HEX4) levels decreased in 8 of 8 patients
By week 4, all 4 biomarker levels decreased in the 2 patients in the treatment-naive cohort (Cohort 3) (FIGS. 27C and 27D).
In FIGS. 27A-27D, data are represented as mean±standard error.

Safety

No serious adverse events (AEs) or infusion-associated reactions were reported after 155+ total infusions in all patients
Treatment-emergent AEs, reported in 11/13 (84%) patients, were generally mild and transient.
Treatment-related AEs reported in 7/13 (53%) patients: nausea (n=1), fatigue (n=1), headache (n=1), tremor (n=2), acne (n=1), tachycardia (n=1), and hypotension (n=1).

CONCLUSIONS

ATB200 alone and in combination with miglustat has been safe and well tolerated, with no infusion-associated reactions to date.
ATB200 alone showed greater-than-dose-proportional increases in exposure, which was further enhanced with miglustat, suggesting a stabilizing effect of chaperone on ATB200.
After switching from standard of care to ATB200/miglustat, patients generally showed an improvement in biomarkers of muscle damage, with many patients demonstrating normalization by week 18.
The initial 2 treatment-naive patients treated with ATB200/miglustat demonstrated robust reduction in all biomarkers of muscle damage The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

Patents, patent applications, publications, product descriptions, GenBank Accession Numbers, and protocols are cited throughout this application, the disclosures of which are incorporated herein by reference in their entireties for all purposes.

What is claimed is:

1. A method for producing purified recombinant human acid alpha-glucosidase (rhGAA), wherein the purified rhGAA comprises an amino acid sequence that is at least 98% identical to SEQ ID NO: 2, the method comprising:
   in a bioreactor, culturing host cells that secrete the rhGAA;
   removing media from the bioreactor;
   filtering the media to provide a filtrate;
   loading the filtrate onto an anion exchange chromatography (AEX) column to capture the rhGAA;
   eluting the rhGAA from the AEX column;
   loading the rhGAA eluted from the AEX column onto an immobilized metal affinity chromatography (IMAC) column; and
   eluting the rhGAA from the IMAC column.

2. The method of claim 1, wherein the purified rhGAA comprises a first potential N-glycosylation site, a second potential N-glycosylation site, a third potential N-glycosylation site, a fourth potential N-glycosylation site, a fifth potential N-glycosylation site, a sixth potential N-glycosylation site, and a seventh potential N-glycosylation site.

3. The method of claim 1, further comprising:
   loading the rhGAA eluted from the IMAC column onto a third chromatography column; and eluting the rhGAA from the third chromatography column.

4. The method of claim 3, wherein the third chromatography column is selected from a cation exchange chromatography (CEX) column and a size exclusion chromatography (SEC) column.

5. The method of claim 3, wherein filtering the media is selected from alternating tangential flow filtration (ATF) and tangential flow filtration (TFF).

6. The method of claim 3, further comprising inactivating viruses in one or more of the rhGAA eluted from the AEX column, the rhGAA eluted from the IMAC column, and the rhGAA eluted from the third chromatography column.

7. The method of claim 3, further comprising filtering the rhGAA eluted from the IMAC column or the rhGAA eluted from the third chromatography column to provide a filtered product and filling a vial with the filtered product.

8. The method of claim 7, further comprising lyophilizing the filtered product.

9. The method of claim 1, wherein the host cells comprise Chinese hamster ovary (CHO) cells.

10. The method of claim 1, wherein:
(i) at least 90% of the purified rhGAA binds to cation-independent mannose-6-phosphate receptor (CIMPR); or
(ii) at least 90% of the purified rhGAA comprises an N-glycan carrying mono-mannose-6-phosphate (mono-M6P) or bis-mannose-6-phosphate (bis-M6P).

* * * * *